United States Patent
Hu

(10) Patent No.: US 11,883,383 B2
(45) Date of Patent: Jan. 30, 2024

(54) PHARMACEUTICALLY ACCEPTABLE SALTS OF [3-(4-{2-BUTYL-1-[4-(4-CHLORO-PHENOXY)-PHENYL]-1H-IMIDAZOL-4-YL}-PHENOXY)-PROPYL]-DIETHYL-AMINE

(71) Applicant: vTv Therapeutics LLC, High Point, NC (US)

(72) Inventor: Juan Hu, Suzhou (CN)

(73) Assignee: VTV THERAPEUTICS LLC, High Point, NC (US)

( * ) Notice: Subject to any disclaimer, the term of this patent is extended or adjusted under 35 U.S.C. 154(b) by 0 days.

(21) Appl. No.: 17/030,611

(22) Filed: Sep. 24, 2020

(65) Prior Publication Data

US 2021/0059988 A1   Mar. 4, 2021

Related U.S. Application Data

(63) Continuation of application No. PCT/US2019/022933, filed on Mar. 19, 2019.

(60) Provisional application No. 62/649,173, filed on Mar. 28, 2018.

(51) Int. Cl.
*A61K 31/4164* (2006.01)

(52) U.S. Cl.
CPC ................ *A61K 31/4164* (2013.01)

(58) Field of Classification Search
CPC .................................. A61K 31/4164
See application file for complete search history.

(56) References Cited

U.S. PATENT DOCUMENTS

| | | |
|---|---|---|
| 4,265,874 A | 5/1981 | Bonsen et al. |
| 4,356,108 A | 10/1982 | Schwab et al. |
| 5,011,849 A | 4/1991 | Gassner et al. |
| 5,166,214 A | 11/1992 | Billheimer et al. |
| 5,550,833 A | 8/1996 | Fujisawa |
| 5,585,344 A | 12/1996 | Vlassara et al. |
| 5,817,826 A | 10/1998 | Ohtani et al. |
| 5,840,294 A | 11/1998 | Kisilevsky et al. |
| 5,864,018 A | 1/1999 | Morser et al. |
| 5,922,770 A | 7/1999 | Peschke et al. |
| 5,939,526 A | 8/1999 | Gaugler et al. |
| 5,962,535 A | 10/1999 | Miyamoto et al. |
| 6,221,887 B1 | 4/2001 | Asghar et al. |
| 6,268,479 B1 | 7/2001 | Stern et al. |
| 6,323,218 B1 | 11/2001 | Bush et al. |
| 6,441,049 B2 | 8/2002 | Reitz et al. |
| 6,613,801 B2 | 9/2003 | Mjalli et al. |
| 6,677,299 B2 | 1/2004 | Stern et al. |
| 6,825,184 B2 | 11/2004 | Cirillo et al. |
| 7,067,554 B2 | 6/2006 | Mjalli et al. |
| 7,087,832 B2 | 8/2006 | Scher et al. |
| 7,329,884 B2 | 2/2008 | Kondo et al. |
| 7,361,678 B2 | 4/2008 | Mjalli et al. |
| 7,381,678 B2 | 6/2008 | Filimonov et al. |
| 7,421,177 B2 | 9/2008 | Schmid et al. |
| 7,423,177 B2 | 9/2008 | Mjalli et al. |
| 7,714,013 B2 | 5/2010 | Mjalli et al. |
| 7,737,285 B2 | 6/2010 | Mjalli et al. |
| 7,776,919 B2 | 8/2010 | Mjalli et al. |
| 7,884,219 B2 | 2/2011 | Hari |
| 8,274,815 B2 | 9/2012 | Ichihara et al. |
| 8,372,988 B2 | 2/2013 | Hari |
| 8,472,145 B2 | 6/2013 | Ho et al. |
| 9,717,710 B2 | 8/2017 | Orlandi et al. |
| 11,420,942 B2 | 8/2022 | Wu |
| 2001/0039256 A1 | 11/2001 | Stern et al. |
| 2002/0006957 A1 | 1/2002 | Mjalli et al. |
| 2002/0118725 A1 | 8/2002 | Mollenkopf |
| 2002/0122799 A1 | 9/2002 | Stern et al. |
| 2002/0193432 A1 | 12/2002 | Mjalli et al. |
| 2003/0032663 A1 | 2/2003 | M. Mjalli et al. |
| 2004/0063770 A1 | 4/2004 | Ahn et al. |
| 2004/0082542 A1 | 4/2004 | Mjalli et al. |
| 2004/0097407 A1 | 5/2004 | Mjalli et al. |
| 2005/0026811 A1 | 2/2005 | Mjalli et al. |
| 2006/0020042 A1 | 1/2006 | Mcdonald et al. |
| 2006/0247253 A1 | 11/2006 | Leban et al. |
| 2007/0021386 A1 | 1/2007 | Mjalli et al. |
| 2007/0135437 A1 | 6/2007 | Benjamin et al. |
| 2009/0035302 A1* | 2/2009 | Mjalli ............... A61P 43/00 514/400 |
| 2010/0048726 A1 | 2/2010 | McDonald et al. |
| 2010/0256119 A1 | 10/2010 | Mjalli et al. |
| 2012/0088778 A1 | 4/2012 | Mjalli et al. |
| 2014/0039025 A1 | 2/2014 | Jones et al. |
| 2017/0326113 A1 | 11/2017 | Orlandi et al. |

(Continued)

FOREIGN PATENT DOCUMENTS

| | | |
|---|---|---|
| WO | WO-9509838 A1 | 4/1995 |
| WO | WO-9728913 A1 | 8/1997 |
| WO | WO-9739121 A1 | 10/1997 |

(Continued)

OTHER PUBLICATIONS

Gupta, Molecules 2018, 23, 1719.*
Banerjee, Crystal Growth & Design, vol. 5, No. 6, 2005, 2229-2309.*
Amendment No. 6 to Form S-1 Registration Statement for vTv Therapeutics Inc .. Jul. 24, 2015. pp. 2-3, 84, 96-99.
ARICEPTO package insert, Feb. 2012.
Barile et al. The RAGE Axis in Early Diabetic Retinopathy. Investigative Opththmology & Visual Science 46(8):2916-2924 (2005).
Basta et al. Advanced glycation end products and vascular inflammation: implications for accelerated atherosclerosis in diabetes. Cardiovascular Research 63:582-592 (2004).

(Continued)

*Primary Examiner* — Nizal S Chandrakumar
(74) *Attorney, Agent, or Firm* — WILSON SONSINI GOODRICH & ROSATI

(57) ABSTRACT

The present invention relates to pharmaceutically acceptable salts of [3-(4-{2-butyl-1-[4-(4-chloro-phenoxy)-phenyl]-1H-imidazol-4-yl}-phenoxy)-propyl]-diethylamine ("COMPOUND I") useful in the treatment of RAGE mediated diseases.

8 Claims, 69 Drawing Sheets

(56) References Cited

U.S. PATENT DOCUMENTS

| | | |
|---|---|---|
| 2019/0142803 A1 | 5/2019 | Orlandi et al. |
| 2022/0298117 A1 | 9/2022 | Wu |

FOREIGN PATENT DOCUMENTS

| | | | | |
|---|---|---|---|---|
| WO | WO-9739125 A1 | 10/1997 | | |
| WO | WO-9822138 A1 | 5/1998 | | |
| WO | WO-9904485 A1 | 1/1999 | | |
| WO | WO-9907402 A1 | 2/1999 | | |
| WO | WO-9918987 A1 | 4/1999 | | |
| WO | WO-0019994 A1 | 4/2000 | | |
| WO | WO-0020458 A1 | 4/2000 | | |
| WO | WO-0020821 A1 | 4/2000 | | |
| WO | WO-0112598 A2 | 2/2001 | | |
| WO | WO-0192210 A1 | 12/2001 | | |
| WO | WO-02070473 A2 | 9/2002 | | |
| WO | WO-02089965 A1 | 11/2002 | | |
| WO | WO-03075921 A2 | 9/2003 | | |
| WO | WO-2004087653 A2 | 10/2004 | | |
| WO | WO-2004110350 A2 | 12/2004 | | |
| WO | WO-2005000295 A1 | 1/2005 | | |
| WO | WO-2006124897 A2 | 11/2006 | | |
| WO | WO-2008067121 A2 | 6/2008 | | |
| WO | WO-2008123914 A1 | 10/2008 | | |
| WO | WO-2008153957 A1 | 12/2008 | | |
| WO | WO-2009107401 A1 | 9/2009 | | |
| WO | WO-2010126745 A1 | 11/2010 | | |
| WO | WO 2011041198 | * | 4/2011 | ........... C07D 233/60 |
| WO | WO-2011041198 A1 | 4/2011 | | |
| WO | WO-2011103091 A1 | 8/2011 | | |
| WO | WO 2014055588 | * | 4/2014 | ........... C07D 233/60 |
| WO | WO-2014055588 A1 | 4/2014 | | |
| WO | WO-2016201368 A1 | 12/2016 | | |
| WO | WO-2018058296 A1 | 4/2018 | | |
| WO | WO-2019190822 A1 | 10/2019 | | |
| WO | WO-2019190823 A1 | 10/2019 | | |

OTHER PUBLICATIONS

Behl et al. Amyloid beta peptide induces necrosis rather than apoptosis. Brain Research 645:253-264 (1994).
Behl et al. Hydrogen Peroxide Mediates Amyloid beta Protein Toxicity. Cell 77:817-827 (1994).
Berge et al. Pharmaceutical Salts. Journal of Pharmaceutical Sciences 66(1):1-19 (Jan. 1977).
Bernstein. Crystal Structure Prediction and Polymorphism. ACA Transactions 39:14-23 (2004).
Bierhaus et al. Advanced Glycation End Product (AGE)-Mediated Induction of Tissue Factor in Cultured Endothelial Cells Is Dependent on RAGE. Circulation 96:2262-2271 (1997).
Bishop et al. Neural mechanisms of ageing and cognitive decline. Nature 464:529-535 (2010).
Blacker et al. Reliability and Validity of NINCDS-ADRDA Criteria for Alzheimer's Disease. Arch. Neur. 51:1198-1204 (1994).
Bonetta. Door Slams on RAGE Alzheimer Research Forum Print News. Available at http://www.alzforum.org/new/detailprint.asp?id=2960 (Nov. 9, 2011).
Bonnardel-Phu et al. Acute Modulation of Albumin Microvascular Leakage by Advanced Glycation End Products in Microcirculation of Diabetic Rats In Vivo. Diabetes 48:2052-2058 (1999).
Burstein et al. Effect of TTP488 in patients with mild to moderate Alzheimer's disease. BMC Neurology 14:12 (2014).
Burstein et al. Development of Azeliragon, an Oral Small Molecule Antagonist of the Receptor for Advanced Glycation Endproducts, for the Potential Slowing of Loss of Cognition in Mild Alzheimer's Disease. J Prev Alzheimers Dis 5(2):149-154 (2018).
Burstein et al. Evaluation of the relationship between TTP488 plasma concentration and changes in ADAS-cog relative to placebo. Poster session presented at: the Alzheimer's Association International Conference. Jul. 13-18, 2013. Boston, Massachusetts.
Byrn et al. Pharmaceutical Solids: A Strategic Approach to Regulatory Considerations. Pharmaceutical Research 12(7):945-954 (1995).
Caira. Crystalline Polymorphism of Organic Compounds. Topics in Current Chemistry. 198:163-208 (Jan. 1998).
Chartier-Harlin et al. Early-onset Alzheimer's disease caused by mutations at codon 717 of the beta-amyloid precursor protein gene. Nature 353:844-846 (1991).
Checler. Processing of the beta-Amyloid Precursor Protein and Its Regulation in Alzheimer's Disease. J Neurochemistry 65(4):1431-1444 (1995).
Chitaley et al. Antagonism of Rho-kinase stimulates rat penile erection via a nitric oxide-independent pathway. Nature Medicine 7(1):119-122 (2001).
Crall et al. The Extramural and Intramural Corollary Arteries in Juvenile Diabetes Mellitus. Am J Med 64:221-230 (1978).
Deane et al. RAGE mediates amyloid-beta peptide transport across the blood-brain barrier and accumulation in brain. Nature Medicine 9:907-913 (2003).
Degenhardt et al. Chemical modification of proteins by methylglyoxal. Cell Mol. Biol. 44:1139-1145 (1998).
Donahue et al. RAGE, LRP-1, and amyloid-beta protein in Alzheimer's disease. Ada Neuropathol 112:405-415 (2006).
Dyer et al. Accumulation of Maillard reaction products in skin collagen in diabetes and aging. J. Clin. Invest. 91:2463-2469 (1993).
Dyer et al. Formation of pentosidine during nonenzymatic browning of proteins by glucose. Identification of glucose and other carbohydrates as possible precursors of pentosidine in vivo. J. Biol. Chem. 266:11654-11660 (1991).
Fang et al. RAGE-dependent signing in microglia contributes to neuroinflammation, A-beta accumulation, and impaired teaming/memory in a mouse model of Alzheimer's disease. The FASEB J 24:1043-1055 (2010).
Galasko et al. Clinical-Neuropathologic Correlations in Alzheimer's Disease and Related Dementia. Arch. Neur. 51:888-895 (1994).
Galasko et al. A clinic trial of an inhibitor of RAGE-A-beta interactions in Alzheimer's disease. RI clinic trial manuscript. Aug. 8, 2012.
Galasko et al. Clinical trial of an inhibitor of RAGE-A-beta interactions in Alzheimer disease. Neurology 82:1536-1542 (2014).
Gavezzotti. "Are Crystal Structures Predictable?" Accounts of Chemical Research 27:309-314 (1994).
Girouard et al. Neurovascular coupling in the normal brain and in hypertension, stroke, and Alzheimer disease. J. Appl. Physiol. 100:328-335 (2006).
Golub et al. Molecular Classification of Cancer: Class Discovery and Class Prediction by Gene Expression Monitoring. Science 286:531-537 (1999).
Goova et al. Blockade of Receptor for Advanced Glycation End-Products Restores Effective Wound Healing in Diabetic Mice. Am J Pathol 159:513-525 (2001).
Haass et al. Cellular Processing of beta-Amyloid Precursor Protein and the Genesis of Amyloid beta-Peptide. Cell 75:1039-1042 (1993).
Hambly et al. Reappraisal of the role of the diabetic state in coronary artery disease. Chest 70(2):251-257 (1976).
Hammes et al. Diabetic retinopathy risk correlates with intracellular concentrations of the glycoxidation product Nepsilon-(carboxymethyl) lysine independently of glycohaemoglobin concentrations. Diabetologia 42:603-607 (1999).
Hofmann et al. RAGE mediates a novel proinflammatory axis: a central cell surface receptor for S100/calgranulin polypeptides. Cell 97:889-901 (1999).
Hori et al. The receptor for advanced glycation end products (RAGE) is a cellular binding site for amphoterin. Mediation of neurite outgrowth and co-expression of rage and amphoterin in the developing nervous system. J. Biol. Chem. 270:25752-761 (1995).
Huttunen et al. Receptor for Advanced Glycation End Products (RAGE)-mediated Neurite Outgrowth and Activation of NF-kB Require the Cytoplasmic Domain of the Receptor but Different Downstream Signing Pathways. J Biol Chem 274(28):19919-19924 (1999).
Japanese Journal of Geriatrics 49(4):419-424 (2012).
Johnson et al. MDL 29311: Antioxidant With Marked Lipid- and Glucose-Lowering Activity in Diabetic Rats and Mice. Diabetes 42:1179-1186 (1993).

(56) References Cited

OTHER PUBLICATIONS

Kamboh. Molecular Genetics of Late-Onset Alzheimer's Disease. Annals of Human Genetics 68:381-404 (2004).
Kannel et al. Diabetes and Glucose Tolerance as Risk Factors for Cardiovascular Disease: The Framingham Study. Diabetes Care 2(2):120-126 (1979).
Kannel et al. Diabetes and Cardiovascular Disease: The Framingham Study. JAMA 241(19):2035-2038 (1979).
Kennedy et al. Familial Alzheimer's disease. Brain 116:309-324 (1993).
Kislinger et al. Receptor for Advanced Glycation End Products Mediates Inflammation and Enhanced Expression of Tissue Factor in Vasculature of Diabetic Apolipoprotein E-Null Mice. Arterioscler Thromb Vasc Biol. 21:905-910 (2001).
Kostura et al. Efficacy of RAGE antagonist in murine model of Alzheimer's disease. Poster session presented at: the Alzheimer's Association International Congress: Jul. 13-18, 2014: Cophenhagen, Denmark.
Kostura et al. Novel Bach1 Modulators Increase HM0X1 and Suppress Hypertension in the Goldblatt Model of Renovascular Hypertension, American Heart Association Scientific Sessions, Nov. 2013, Poster.
Kumar et al. RAGE at the Blood-Brain Barrier Mediates Neurovascular Dysfunction Caused by Amyloid-bet-40 Peptide. Neurosci. Program, p141 #275.19 (2000).
Lander et al. Activation of the Receptor for Advanced Glycation End Products Triggers a p21 (ras)-dependent Mitogen-activated Protein Kinase Pathway Regulated by Oxidant Stress. J Biol Chem 272(28):17810-17814 (1997).
Levy-Lahad et al. Candidate Gene for the Chromosome 1 Familial Alzheimer's Disease Locus, Science. New Series 269(5226):973-977 (1995).
Li et al. Characterization and functional analysis of the promoter of RAGE, the receptor for advanced glycation end products. J. Biol. Chem. 272:16498-16506 (1997).
Li et al. Sp1-binding elements in the promoter of RAGE are essential for amphoterin-mediated gene expression in cultured neuroblastoma cells. J. Biol. Chem. 273:30870-30878 (1998).
Mackic et al. Human blood-brain barrier receptors for Alzheimer's amyloid-beta 1-40. Asymmetrical binding, endocytosis, and transcytosis at the apical side of brain microvascular endothelial cell monolayer. J. Clin. Invest. 102:734-743 (1998).
Mangialasche. Alzheimer's disease: clinic tris and drug development. The LANCET Neurology 9(7):702-716 (2010).
McKhann et al.:Clinical diagnosis of Alzheimer's disease: report of the NINCDS-ADRDA Work Group under the auspices of Department of Health and Human Services Task Force on Alzheimer's Disease. Neurology 34(7):939-944 (1984).
Miyata et al. beta 2-Microglobulin modified with advanced glycation end products is a major component of hemodialysis-associated amyloidosis. J. Clin. Invest. 92:1243-1252 (1993).
Miyata et al. The receptor for advanced glycation end products (RAGE) is a central mediator of the interaction of AGE-beta2microglobulin with human mononuclear phagocytes via an oxidant-sensitive pathway. Implications for the pathogenesis of dialysis-related amyloidosis J. Clin. Invest. 98:1088-1094 (1996).
Morcos et al. Activation of Tubular Epithelial Cells in Diabetic Nephropathy. Diabetes 51:3532-3544 (2002).
Morris et al. Place navigation impaired in rats with hippocampal lesions. Nature 297:681-683 (1982).
Namenda® package insert. 2007 Jan. 2011.
Neeper et al. Cloning and expression of a cell surface receptor for advanced glycosylation end products of proteins. J. Biol. Chem. 267:14998-15004 (1992).
Ohkubo et al. Studies on Cerebral Protective Agents. VII. Synthesis of Novel 4-Arylazole Derivatives with Anti-anoxic Activity, Chem. Pharm. Bull. 43(6):947-954 (1995).

Oldfield et al. Advanced glycation end products cause epithelial-myofibroblast transdifferentiation via the receptor for advanced glycation end products (RAGE). J Clin Invest 108(12):1853-1863 (2001).
Pappolla et al. The Heat Shock/Oxidative Stress Connection: Relevance to Alzheimer Disease. Mol Chem Neropathol 28:21-24 (1996).
Park et al. Suppression of accelerated diabetic atherosclerosis by the soluble receptor for advanced glycation endproducts. Nature Medicine 4(9):1025-1031 (1998).
Parkkinen et al. Amphoterin, the 30-kDa protein in a family of HMG1-type polypeptides. Enhanced expression in transformed cells, leading edge localization, and interactions with plasminogen activation. J. Biol. Chem. 268:19726-19738 (1993).
Pastor et al. Molecular Genetics of Alzheimer's Disease. Current Psychiatry Reports 6:125-133 (2004).
PCT/US2008/00325 International Search Report and Written Opinion dated Jun. 30, 2008.
PCT/US2019/022932 International Search Report and Written Opinion dated May 28, 2019.
PCT/US2019/022933 International Search Report and Written Opinion dated May 29, 2019.
Perrone et al. The Complexity of Sporadic Alzheimer's Disease Pathogenesis: The Role of RAGE as Therapeutic Target to Promote Neuroprotection by Inhibiting Neurovascular Dysfunction. Int J Alzheimer's Dis 2012:734956 (2012).
Pike et al. Neurodegeneration Induced by beta-Amyloid Peptides in vitro: The Role of Peptide Assembly State. J Neurosciences 13(4):1676-1687 (1993).
Porretta et al. Chemotherapeutic agents with an imidazole moiety. III. Synthesis and microbiologic activity of new 1,4-diaryllimidazole and 1,4-pyrrolimidazolephenylene derivatives. Il Farmaco 46(7,8):913-924 (1991).
Pyorala et al. Diabetes and Atherosclerosis: An Epidemiologic View. Diabetes/Metabolism Reviews 3(2):463-524 (1987).
Ramasamy et al. Advanced glycation end products and RAGE: a common thread in aging, diabetes, neurodegeneration, and inflammation. Glycobiology 15:16R-18R (2005).
Rammes et al. Myeloid-related protein (MRP) 8 and MRP14, calcium-binding proteins of the S100 family, are secreted by activated monocytes via a novel, tubulin-dependent pathway. J. Biol. Chem. 272:9496-9502 (1997).
Ranginwala et al. Clinic Criteria for the Diagnosis of Alzheimer Disease: Still Good After I These Years. Am. J. Geriatr. Psychiatry 16(5):384-388 (2008).
Rauvala et al. Isolation and some characteristics of an adhesive factor of brain that enhances neurite outgrowth in central neurons. J. Biol. Chem. 262:16625-16635 (1987).
Reddy et al. N epsilon-(carboxymethyl) lysine is a dominant advanced glycation end product (AGE) antigen in tissue proteins. Biochem. 34:10872-10878 (1995).
Ritthaler et al. Expression of Receptors for Advanced Glycation End Products in Peripheral Occlusive Vascular Disease. Am J Pathol 146(3):688-694 (1995).
Robertson et al. Atherosclerosis in persons with Hypertension and Diabetes Mellitus. Laboratory investigation 18(5):538-551 (1968).
Rogaev et al. Familial Alzheimer's disease in kindreds with missense mutations in a gene on chromosome 1 related to the Alzheimer's disease type 3 gene. Nature 376:775-778 (1995).
Sabbagh et al. Abstract TTP488: From Futile to Fast Track. Presented at the 2015 Alzheimer's Association International Conference. Washington, DC, Jul. 2015.
Sabbagh et al. Abstract TTP488 Path to Registration: Leveraging Enrichment Strategies. Presented at the 2015 Alzheimer's Association International Conference. Washington. DC, Jul. 2015.
Sabbagh et al. PF-04494700, an Oral Inhibitor of Receptor for Advanced Glycation End Products (RAGE), in Alzheimer Disease. Alzheimer Dis Assoc Disord 25(3):206-12 (2011).
Sabbagh et al. Safety and efficacy results from the phase 3. multicenter, 18-month STEADFAST tri of azeliragon in participants with mild Alzheimer's disease. Presented at 2018 CTAD. Oct. 26, 2018. Barcelona, Spain.

(56) References Cited

OTHER PUBLICATIONS

Sabbagh et al. TTP488 Path to Registration: Leveraging Enrichment Strategies. Presented at the 2015 Alzheimer's Association International Conference. Washington, DC, Jul. 2015.
Schafer et al. The S100 family of EF-hand calcium-binding proteins: functions and pathology. Trends Biochem Sci 21:134-140 (1996).
Schleicher et al. Increased accumulation of the glycoxidation product N(epsilon)-(carboxymethyl)lysine in human tissues in diabetes and aging. J. Clin. Invest. 99 (3):457-468 (1997).
Schmidt et al. Advanced Glycation Endproducts Interacting with Their Endothelial Receptor Induce Expression of Vascular Cell Adhesion Molecule-1 (VCAM-1) in Cultured Human Endothelial Cells and in Mice. J. Clin. Invest 96:1395-1403 (1995).
Schmidt et al. Receptor for advanced glycation end products (AGEs) has a central role in vessel wall interactions and gene activation in response to circulating AGE proteins. PNAS USA 91:8807-8811 (1994).
Schmidt et al. The V-Domain of Receptor for Advanced Glycation Endproducts (RAGE) Mediates Binding of Ages: A Novel Target for Therapy of Diabetic Complications. Supplement to Circulation 96(8):Abstract No. 194 (1997).
Schmidt et al. Isolation and Characterization of Two Binding Proteins for Advanced Glycosylation End Products from Bovine Lung Which Are Present on the Endothelial Cell Surface. J Biol Chem 267(21):14987-14977 (1992).
Schmidt et al. The dark side of glucose. Nature Med. 1:1002-1004 (1995).
Selkoe. Normal and Abnormal Biology of the beta-Amyloid Precursor Protein. Annu Review of Neuroscience 17:489-517 (1994).
Selkoe. The Molecular Pathology of Alzheimer's Disease. Neuron 6:487-498 (1991).
Selkoe. Translating cell biology into therapeutic advances in Alzheimer's disease. Nature 399:A23-31 (1999).
Semprini et al. Evidence for differential S100 gene over-expression in psoriatic patients from genetically heterogeneous pedigrees. Hum. Genet. 111(4-5):310-3 (2002).
Sherrington et al. Cloning of a gene beating missense mutations in early-onset familial Alzheimer's disease. Nature 375:754-760 (1995).
Sims et al. HMGB1 and RAGE in inflammation and cancer. Annual Review of Immunology 28:367-368 (2010).
Snowdon. Healthy Aging and Dementia: Findings from the Nun Study. Annals of Intern Medicine 139(5):450-454 (2003).
Sousa et al. Interaction of the Receptor for Advanced Glycation End Products (RAGE) with Transthyretin Triggers Nuclear Transcription Factor Kb (NF-kb) Activation. Laboratory Investigation 80(7):1101-1110 (2000).
Spite et al. Novel Lipid Mediators Promote Resolution of Acute Inflammation: Impact of Aspirin and Statins. Circulation Research 107:1170-1184 (2010).
Strittmatter et al. Apolipoprotein E: High-avidity binding to beta-amyloid and increased frequency of type 4 allele in late-onset familial Alzheimer disease. PNAS USA 90:1977-1981 (1993).
Taguchi et al. Blockade of RAGE-amphoterin signalling suppresses tumour growth and metastases. Nature 405:354-360 (2000).
Takuma et al. RAGE-mediated signing contributes to intraneuronal transport of amyloid-beta and neuron dysfunction, PNAS 106(47):20021-20026 (2009).
Tanaka et al. The receptor for advanced glycation end products is induced by the glycation products themselves and tumor necrosis factor-alpha through nuclear factor-kappa B, and by 17beta-estradiol through Sp-1 in human vascular endothelial cells. J. Biol. Chem. 275:25781-25790 (2000).
Teillet et al. Food restriction prevents advanced glycation end product accumulation and retards kidney aging in lean rats. J. Am. Soc. Nephrol 11:1488-1497 (2000).
Thompson et al. Protein Conformation Misfolding and Amyloid Formation: Characteristics of a New Class of Disorders that Include Alzheimer's and Prion Diseases. Current Medicinal Chemistry 9:1751-1762 (2002).
Vellas et al. Long-term changes in ADAS-cog: What is clinically relevant for disease modifying trails in Alzheimer? J Nutr Health Aging 11(4):338-341 (2007).
Vlassara et al. Advanced Glycation End-products and Atherosclerosis. Ann. Med. 28:419-426 (1996).
VTv Therapeutics LLC. vTv Therapeutics Announces Topline Results from Part B of Phase 3 STEADFAST Study (Jun. 12, 2018) [Press Release].
VTv Therapeutics LLC. vTv Therapeutics Announces Topline Results from the First STEADFAST Phase 3 Study Evaluating Azeliragon in People with Mild Alzheimer's Disease (Apr. 9, 2018). [Press Release].
Waller et al. Status of the coronary arteries at necropsy in diabetes mellitus with onset after age 30 years. Analysis of 229 diabetic patients with and without clinical evidence of coronary heart disease and comparison to 183 control subjects. Am J Med 69:498-506 (1980).
Wang et al. The Profile of Soluble Amyloid beta Protein in Cultured Cell Media: Detection and Quantification of Amyloid beta Protein and Variants by immunoprecipitation—Mass Spectrometry. J Biol Chem 271(50):31894-31902 (1996).
Wautier et al. Advanced glycation end products (AGES) on the surface of diabetic erythrocytes bind to the vessel wall via a specific receptor inducing oxidant stress in the vasculature: A link between surface-associated AGEs and diabetic complications. PNAS USA 91:7742-7746 (1994).
Wautier et al. Receptor-mediated endothelial cell dysfunction in diabetic vasculopathy. Soluble receptor for advanced glycation end products blocks hyperpermeability in diabetic rats. J. Clin. Invest. 97:238-243 (1995.
Wisniewski et al. Apolipoprotein E: a pathologic chaperone protein in patients with cerebral and systemic amyloid. Neuroscience Letters 135:235-238 (1992).
Yan et al. Enhanced Cellular Oxidant Stress by the Interaction of Advanced Glycation End Products with Their Receptors/Binding Proteins. J Biol Chem 269(13):9889-9897 (1994).
Yan et al. RAGE and Alzheimer's Disease: A Progression Factor for Amyloid-beta-induced Cellular Perturbation? J Alzheimer's Dis 16:833-843 (2009).
Yan et al. Amyloid-beta peptide-receptor for advanced glycation endproduct interaction elicits neuronal expression of macrophage-colony stimulating factor: a proinflammatory pathway in Alzheimer disease. PNAS USA 94:5296-5301 (1997).
Yan et al. An intracellular protein that binds amyloid-beta peptide and mediates neurotoxicity in Alzheimer's disease. Nature 389:689-695 (1997).
Yan et al. RAGE and amyloid-beta peptide neurotoxicity in Alzheimer's disease. Nature 382:685-691 (1996).
Yan et al. Receptor-dependent cell stress and amyloid accumulation in systemic amyloidosis. Nat. Med. 6:643-651 (2000).
Yankner et al. Neurotrophic and Neurotoxic Effects of Amyloid beta Protein: Revers by Tachykinin Neuropeptides. Science 250(4978):279-282 (1990).
Yeh et al. Requirement for p38 and p44/p42 Mitogen-Activated Protein Kinases in RAGE-Mediated Nuclear Factor-kB Transcription Activation and Cytokine Secretion. Diabetes 50:1495-1504 (2001).
Zimmer et al. The S100 protein family: history, function, and expression. Brain Res. Bull. 37:417-429 (1995).

\* cited by examiner

PHARMACEUTICALLY ACCEPTABLE SALTS OF [3-(4-{2-BUTYL-1-[4-(4-CHLORO-PHENOXY)-PHENYL]-1H-IMIDAZOL-4-YL}-PHENOXY)-PROPYL]-DIETHYL-AMINE

FIELD OF THE INVENTION

This application is a continuation of International Application No. PCT/US2019/22933, filed March 19, 2019, which claims the benefit of U.S. Provisional Application No. 62/649,173, filed March 28, 2018, each of which is incorporated herein by reference in their entirety for all purposes.

BACKGROUND OF THE INVENTION

The Receptor for Advanced Glycation Endproducts (RAGE) is a member of the immunoglobulin super family of cell surface molecules. Activation of RAGE in different tissues and organs leads to a number of pathophysiological consequences. RAGE has been implicated in a variety of conditions including: acute and chronic inflammation (Hofmann et al., Cell 97:889-901 (1999)), the development of diabetic late complications such as increased vascular permeability (Wautier et al., J. Clin. Invest. 97:238-243 (1995)), nephropathy (Teillet et al., J. Am. Soc. Nephrol. 11: 1488-1497 (2000)), atherosclerosis (Vlassara et. al., The Finnish Medical Society DUODECIM, Ann. Med. 28:419-426 (1996)), and retinopathy (Hammes et al., Diabetologia 42:603-607 (1999)). RAGE has also been implicated in Alzheimer's disease (Yan et al., Nature 382: 685-691, (1996)), erectile dysfunction, and in tumor invasion and metastasis (Taguchi et al., Nature 405: 354-357, (2000)).

Binding of ligands such as advanced glycation endproducts (AGEs), S100/calgranulin/EN-RAGE, β-amyloid, CML (N-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21ras.

MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Antagonizing binding of physiological ligands to RAGE, therefore, is our target, for down-regulation of the pathophysiological changes brought about by excessive concentrations of AGEs and other ligands for RAGE.

Pharmaceutically acceptable salts of a given compound may differ from each other with respect to one or more physical properties, such as solubility and dissociation, true density, melting point, crystal shape, compaction behavior, flow properties, and/or solid state stability. These differences affect practical parameters such as storage stability, compressibility and density (important in formulation and product manufacturing), and dissolution rates (an important factor in determining bio-availability). Although U.S. Pat. No. 7,884,219 discloses Form I and Form II of COMPOUND I as a free base, there is a need for additional drug forms that are useful for inhibiting RAGE activity in vitro and in vivo, and have properties suitable for large-scale manufacturing and formulation. Provided herein are new pharmaceutically acceptable salt forms of COMPOUND I, as well as methods of producing the pharmaceutically acceptable salt forms of COMPOUND I.

SUMMARY OF THE INVENTION

The preparation of [3-(4-{2-butyl-1-[4-(4-chloro-phenoxy)-phenyl]-1H-imidazol-4-yl}-phenoxy)-propyl]-diethyl-amine ("COMPOUND I") and the use thereof, such as an antagonist of the receptor for advanced glycation endproducts (RAGE) and in the treatment of various medical conditions, are described in US Patent Publication No. 2004-0082542 and in US Patent Publication No. 2005-0026811. Such diseases or disease states may include, but are not limited to, acute and chronic inflammation, amyloidosis, Alzheimer's disease, cancer, tumor invasion and metastasis, kidney failure, or inflammation associated with autoimmunity, inflammatory bowel disease, rheumatoid arthritis, psoriasis, multiple sclerosis, hypoxia, stroke, heart attack, hemorrhagic shock, sepsis, organ transplantation, the development of diabetic late complications such as increased vascular permeability, diabetic nephropathy, diabetic retinopathy, a diabetic foot ulcer, a cardiovascular complication, diabetic neuropathy, impaired wound healing, erectile dysfunction, and osteoporosis. COMPOUND I and a method for its preparation are exemplified in US Patent Publication No. 2004-0082542 in Example 406.

In one aspect, the present invention provides pharmaceutically acceptable salt forms of COMPOUND I. In one embodiment, the present invention provides a crystalline or amorphous pharmaceutically acceptable salt of COMPOUND I. In one aspect, the pharmaceutically acceptable salt of COMPOUND I is anhydrous, a hydrate, or a solvate.

In another aspect, the present invention provides a pharmaceutical composition comprising one or more of the pharmaceutically acceptable salt forms of COMPOUND I.

In another aspect, the present invention provides a method of producing a pharmaceutical composition comprising one or more pharmaceutically acceptable salt forms of COMPOUND I.

In another aspect, the present invention provides a method of treating one or more RAGE mediated diseases comprising administering one or more pharmaceutically acceptable salts COMPOUND I to a subject in need thereof. Embodiments of the method of treatment of the present invention may comprise administering a pharmaceutical composition comprising a therapeutically effective amount of one or more pharmaceutically acceptable salts of COMPOUND I These and other embodiments of the present invention are described in greater detail in the detailed description of the invention which follows.

DETAILED DESCRIPTION

Figure 1:
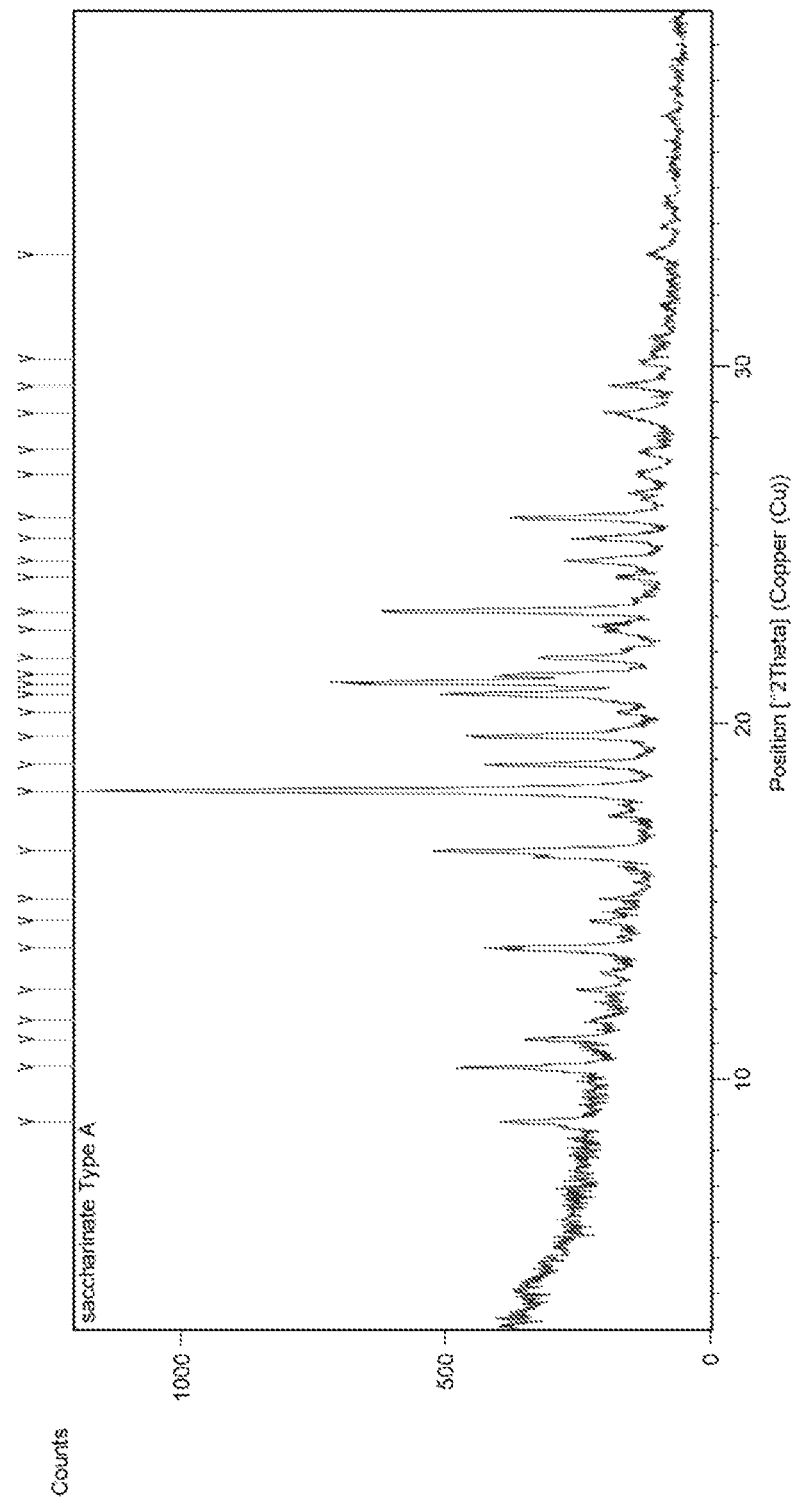
FIG. 1 is a Powder X-ray Powder Diffraction (XRPD) Pattern of saccharinate Type A.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

By percent by weight it is meant that a particular weight of one ingredient in a composition is divided by the total weight of all of the ingredients in that composition. Percent by weight may be used interchangeably and means approximately the same as weight/weight percent or % (weight/weight) or percent by mass or mass percent. When a liquid solute is used, it is often more practical to use volume/volume percent or % (vol/vol) or percent by volume, which are all considered to be synonymous. Ppm (parts per million), ppb (parts per billion), pph (parts per hundred) are often used to indicate a percentage based on quantity and not on mass (i.e., the quantity of a given type of atom or a given type of molecule in a composition with more atoms or molecules (be it gas, liquid or solid) is divided by the total quantity of atoms or molecules in the total composition). Other terms that are used are molarity, which is the number of moles of solute per liters of solution, and molality, which is the number of moles of solution per kilograms of solution. Another concentration unit is the mole fraction, which is the moles of a given component divided by the total moles of all solution components. Mole percent is related to the mole fraction and is the mole fraction multiplied by 100.

It is further noted that, as used in this specification, the singular forms "a," "an," and "the" include plural referents unless expressly and unequivocally limited to one referent.

The term "RAGE mediated disease" is used herein to refer to one or more conditions, diseases or disease states including, but not limited to, acute or chronic inflammation including skin inflammation such as psoriasis, rheumatoid arthritis, atopic dermatitis and lung inflammation including, asthma and chronic obstructive pulmonary disease, diabetes, diabetes related complications, renal failure, hyperlipidemic atherosclerosis associated with diabetes, neuronal cytotoxicity, restenosis, Down's syndrome, dementia associated with head trauma, amyotrophic lateral sclerosis, multiple sclerosis, amyloidosis, an autoimmune disease including inflammation associated with autoimmunity or organ, tissue, or cell transplant, impaired wound healing, periodontal disease, neuropathy, neuronal degeneration, vascular permeability, nephropathy, atherosclerosis, retinopathy, Alzheimer's disease, erectile dysfunction, tumor invasion and/or metastasis, osteoporosis, and the development of diabetic late complications such as increased vascular permeability, nephropathy, retinopathy, and neuropathy. The pharmaceutical compositions comprising a pharmaceutically acceptable salt of COMPOUND I also may be used to antagonize RAGE in a subject.

The term "therapeutically effective amount" is used herein to denote the amount of the pharmaceutically acceptable salt COMPOUND I that will elicit the therapeutic response of a subject that is being sought. In an embodiment, the therapeutic response may be antagonizing RAGE.

Embodiments of the invention are directed to pharmaceutically acceptable salts of COMPOUND I, wherein the particular pharmaceutically acceptable salt (e.g., HCl, HBr) has at least a particular percentage of purity. In some embodiments of the invention, the pharmaceutically acceptable salt of COMPOUND I (e.g., HCl, HBr) is at least 80% pure. In some embodiments of the invention, the pharmaceutically acceptable salt of COMPOUND I (e.g., HCl, HBr) is at least 85% pure. In some embodiments of the invention, the pharmaceutically acceptable salt of COMPOUND I (e.g., HCl, HBr) is at least 90% pure. In some embodiments of the invention, the pharmaceutically acceptable salt of COMPOUND I (e.g., HCl, HBr) is at least 95% pure. In some embodiments of the invention, the pharmaceutically acceptable salt of COMPOUND I is in crystalline (e.g., HCl Type A or HCl Type B) or amorphous form and is substantially free of other polymorphic forms. As used herein, a first polymorphic form that is "substantially pure" of another polymorphic form includes the complete absence of the second form or an amount of the second form that is not readily detectable by ordinary analytical methods. Such ordinary analytical methods include DSC, solid state $^{13}$C NMR, Raman, X-ray powder diffraction, mid-IR (such as FT-IR) and near-IR. In an embodiment, an amount of a polymorphic form that is not readily detectable by one or more ordinary analytical methods is less than 5 percent by weight. In another embodiment, the amount of a polymorphic form that is not readily detectable by one or more ordinary analytical methods is less than 3 percent by weight. In another embodiment, the amount of a polymorphic form that is not readily detectable by one or more ordinary analytical methods is less than 2 percent by weight. In another embodiment, the amount of a polymorphic form that is not readily detectable by one or more ordinary analytical methods is less than 1 percent by weight. In another embodiment, the amount of a polymorphic form that is not readily detectable by one or more ordinary analytical methods is less than 0.5 percent by weight.

In another embodiment, the dosage or blood level of COMPOUND I and administration may be sufficient for inhibition of the biological function of RAGE at a sufficient level for sufficient time to reverse amyloidosis.

A therapeutically effective amount may be achieved in a subject by administering a dosage level of less 100 mg of compound per day. In another embodiment, the dosage level of administration is greater than 1 mg of compound per day. In another embodiment, the dosage level of administration is 5, 10 or 20 mg of compound per day.

The term "treatment" as used herein, refers to the full spectrum of treatments for a given condition or disorder from which a subject is suffering, including alleviation or amelioration of one or more of the symptoms resulting from that disorder, to the delaying of the onset or progression of the disorder.

In one aspect, the present invention provides a pharmaceutically acceptable salt of COMPOUND I. In one embodiment, the present invention is a pharmaceutically acceptable salt is formed between [3-(4-{2-butyl-1-[4-(4-chlorophenoxy)phenyl]-1H-imidazol-4-yl}phenoxy)-propyl]-diethylamine and a pharmaceutically acceptable acid. In one embodiment, the pharmaceutically acceptable acid is selected from the group consisting of 1-hydroxy-2-naphthoic acid, 4-aminosalicylic acid, adipic acid, L-aspartic acid, benzene sulfonic acid, benzoic acid, trans-cinnamic acid, citric acid, fumaric acid, galactaric acid, gentisic acid, gluconic acid, glutamic acid, glutaric acid, hexanoic acid, hippuric acid, hydrobromic acid, hydrochloric acid, L-lactic acid, maleic acid, L-malic acid, malonic acid, R-mandelic acid, methane sulfonic acid, naphthalene sulfonic acid, nicotinic acid, oxalic acid, palmitic acid, phosphoric acid, propionic acid, saccharin, salicyclic acid, stearic acid, succinic acid, sulfuric acid, L-tartaric acid, vanillic acid, and vanillin. In one embodiment, the pharmaceutically acceptable acid is selected from the group consisting of 4-aminosalicylic acid, fumaric acid, galactaric acid, gentisic acid, hippuric acid, hydrobromic acid, hydrochloric acid, L-lactic acid, maleic acid, L-malic acid, oxalic acid, phosphoric acid, saccharin, salicyclic acid, L-tartaric acid, and vanillin.

In one embodiment, the pharmaceutically acceptable salt of COMPOUND I is in a crystalline form. In one embodiment, the pharmaceutically acceptable salt of COMPOUND I is amorphous. In one embodiment, the pharmaceutically acceptable salt of COMPOUND I is anhydrous, a hydrate, or a solvate.

For all embodiments disclosed herein, a peak positional reproducibility is associated with the values of degree-2θ (XRPD), ppm (NMR), and cm$^{-1}$ (IR and Raman). Accordingly, it will be understood that all peaks disclosed herein have the value disclosed±the peak positional reproducibility associated with each analytical technique. The XRPD peak positional reproducibility is ±0.2 expressed in degree-2θ. The $^{13}$C NMR peak positional reproducibility is ±0.2 ppm. The IR peak positional reproducibility is ±2 cm$^{-1}$. The Raman peak positional reproducibility is ±2 cm$^{-1}$.

Pharmaceutically Acceptable Salts of Compound I

Saccharinate

In one aspect of the invention, the pharmaceutically acceptable salt of COMPOUND I is a saccharinate. In one embodiment, the saccharinate is crystalline. In one embodiment, the saccharinate is crystalline and is characterized by an XRPD pattern having peaks at 2θ angles of 18.1°, 21.1°, and 25.7±0.2°. In one embodiment, the saccharinate is crystalline and is characterized by an XRPD pattern having peaks at 2θ angles of 18.1°, 18.8°, 19.6°, 21.1°, 21.4°, and 23.1°±0.2°. In one embodiment, the saccharinate is crystalline and is characterized by an XRPD pattern as shown in FIG. 1. In one embodiment, the saccharinate is crystalline and is characterized by a $^1$H-NMR substantially similar to FIG. 2.

Figure 3:
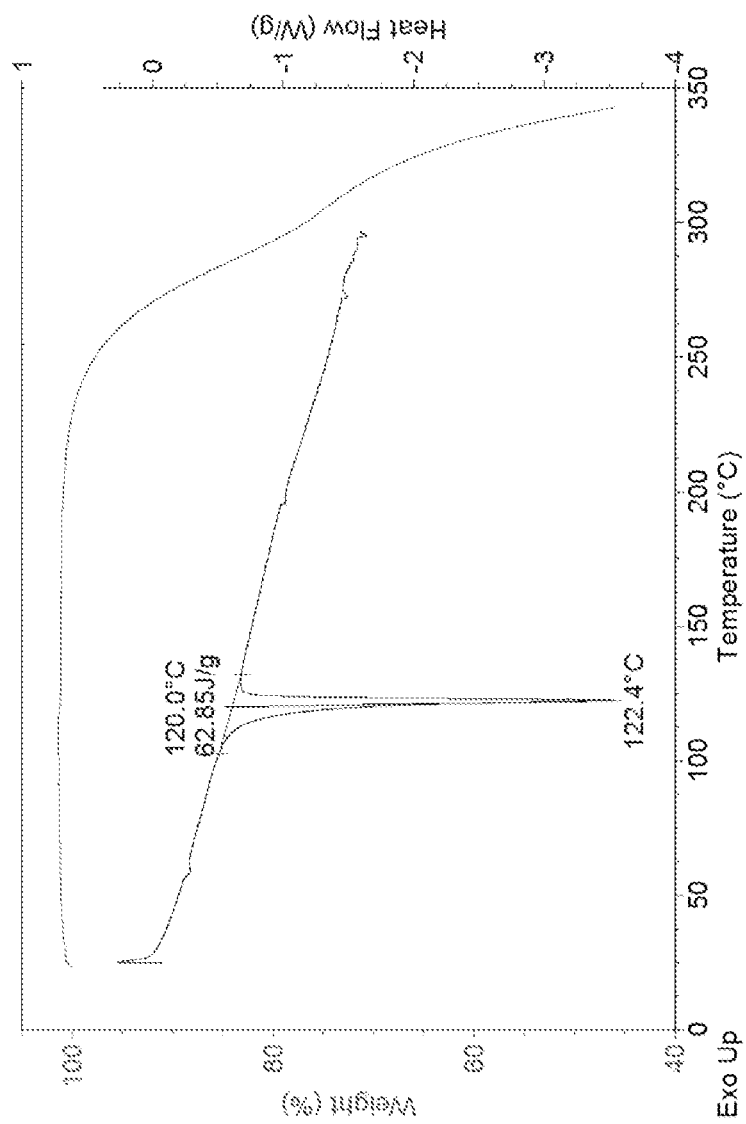
FIG. 3 is a Differential Scanning Calorimetry (DSC) profile and a Thermogravimetric Analysis (TGA) of saccharinate Type A.

In one embodiment, the saccharinate is crystalline and is characterized by an endothermic peak at about 122° C. as determined by DSC. In one embodiment, the saccharinate is crystalline and is characterized by a DSC profile as shown in FIG. 3. In one embodiment, the saccharinate is crystalline and is characterized by a TGA profile as shown in FIG. 3. In one embodiment, the saccharinate is crystalline and is characterized by at least two of the following features (I-i)-(I-iv):

(I-i) an XRPD pattern having peaks at 2θ angles of 18.1, 21.1, and 25.7°±0.2°;
(I-i) a 1H-NMR substantially similar to FIG. 2;
(I-iii) a DSC profile as shown in FIG. 3; or
(I-iv) a TGA profile as shown in FIG. 3.

In one embodiment, the saccharinate is crystalline and is saccharinate Type A.

Saccharinate Type A is characterized by the following XRPD pattern expressed in terms of the degree 2θ and relative intensities:

| Angle (Degree 2θ) | Relative Intensity* % |
|---|---|
| 8.8 | 15.5 |
| 10.3 | 25.7 |
| 11.1 | 14.3 |
| 11.7 | 3.37 |

| Angle (Degree 2θ) | Relative Intensity* % |
|---|---|
| 12.5 | 7.39 |
| 13.7 | 23.82 |
| 14.4 | 6.82 |
| 15.1 | 4.91 |
| 16.4 | 34.84 |
| 18.1 | 100.0 |
| 18.8 | 28.98 |
| 19.6 | 29.87 |
| 20.3 | 5.04 |
| 20.8 | 36.70 |
| 21.1 | 49.86 |
| 21.4 | 26.04 |
| 21.8 | 19.65 |
| 22.6 | 7.80 |
| 23.1 | 45.73 |
| 24.1 | 6.17 |
| 24.5 | 15.48 |
| 25.2 | 14.07 |
| 25.8 | 24.65 |
| 27.0 | 3.75 |
| 27.7 | 3.13 |
| 28.7 | 9.19 |
| 29.4 | 9.74 |
| 30.2 | 2.97 |
| 33.1 | 3.22 |

*The relative intensities may change depending on the crystal size and morphology.

Figure 53:
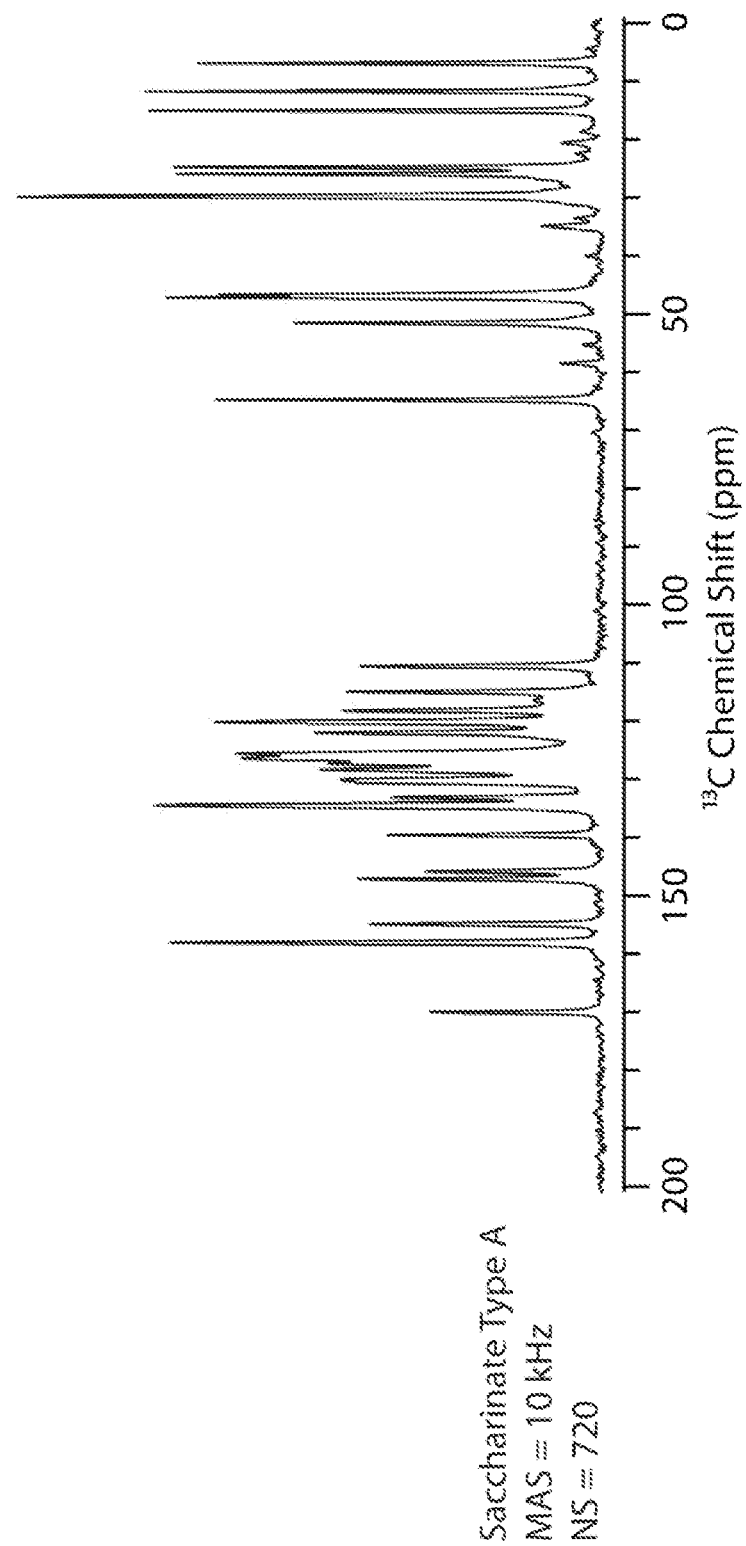
FIG. 53 is a $^{13}$C Solid-state Nuclear Resonance Spectroscopy (SSNMR) spectrum of Saccharinate Type A.

In one embodiment, saccharinate Type A is characterized by the SSNMR of FIG. 53. In one embodiment, saccharinate Type is characterized by the following $^{13}C$ Solid State NMR shifts.

| v(F1) [ppm] | Intensity [abs] |
|---|---|
| 169.99 | 348476560 |
| 158.04 | 882187640 |
| 154.81 | 471063592 |
| 147.08 | 497006496 |
| 145.85 | 356972988 |
| 139.54 | 434512856 |
| 134.41 | 914373752 |
| 133.09 | 428331484 |
| 130.00 | 533065204 |
| 128.28 | 575535956 |
| 127.26 | 556512708 |
| 126.41 | 734651768 |
| 125.56 | 745240568 |
| 121.97 | 584658680 |
| 120.09 | 789557672 |
| 118.17 | 529319796 |
| 116.30 | 135318568 |
| 114.90 | 518273760 |
| 110.56 | 491842772 |
| 64.72 | 787873000 |
| 58.43 | 80322688 |
| 55.23 | 33582176 |
| 51.49 | 627633488 |
| 47.11 | 888065944 |
| 46.63 | 780622880 |
| 40.00 | 30170972 |
| 34.86 | 119540948 |
| 33.51 | 52442604 |
| 29.80 | 1194411844 |
| 27.71 | 83078132 |
| 25.88 | 867195988 |
| 24.72 | 873598400 |
| 22.93 | 35566280 |
| 22.43 | 50581924 |
| 20.52 | 77779132 |
| 18.61 | 39138544 |
| 15.01 | 924607872 |
| 13.63 | 29518844 |
| 11.67 | 931443940 |
| 8.31 | 25583048 |
| 6.84 | 824064900 |
| 4.26 | 28968036 |

Representative $^{13}C$ NMR chemical shifts for saccharinate Type A are 158.04, 134.41, 126.41, and 29.80 ppm. Representative $^{13}C$ NMR chemical shifts for saccharinate Type A are also 158.04, 134.41, and 126.41 ppm.

Vanillate

Figure 4:
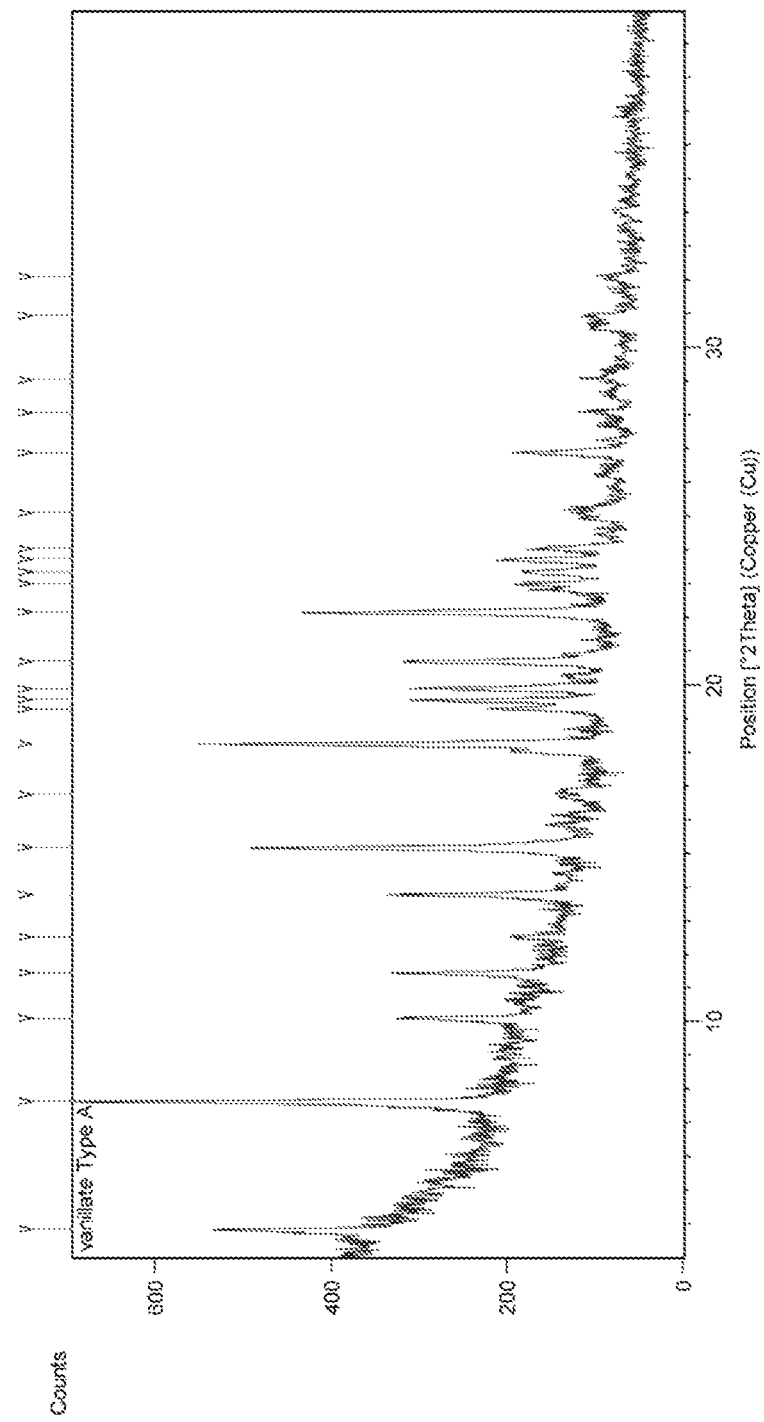
FIG. 4 is a XRPD Pattern of vanillate Type A.
Figure 5:
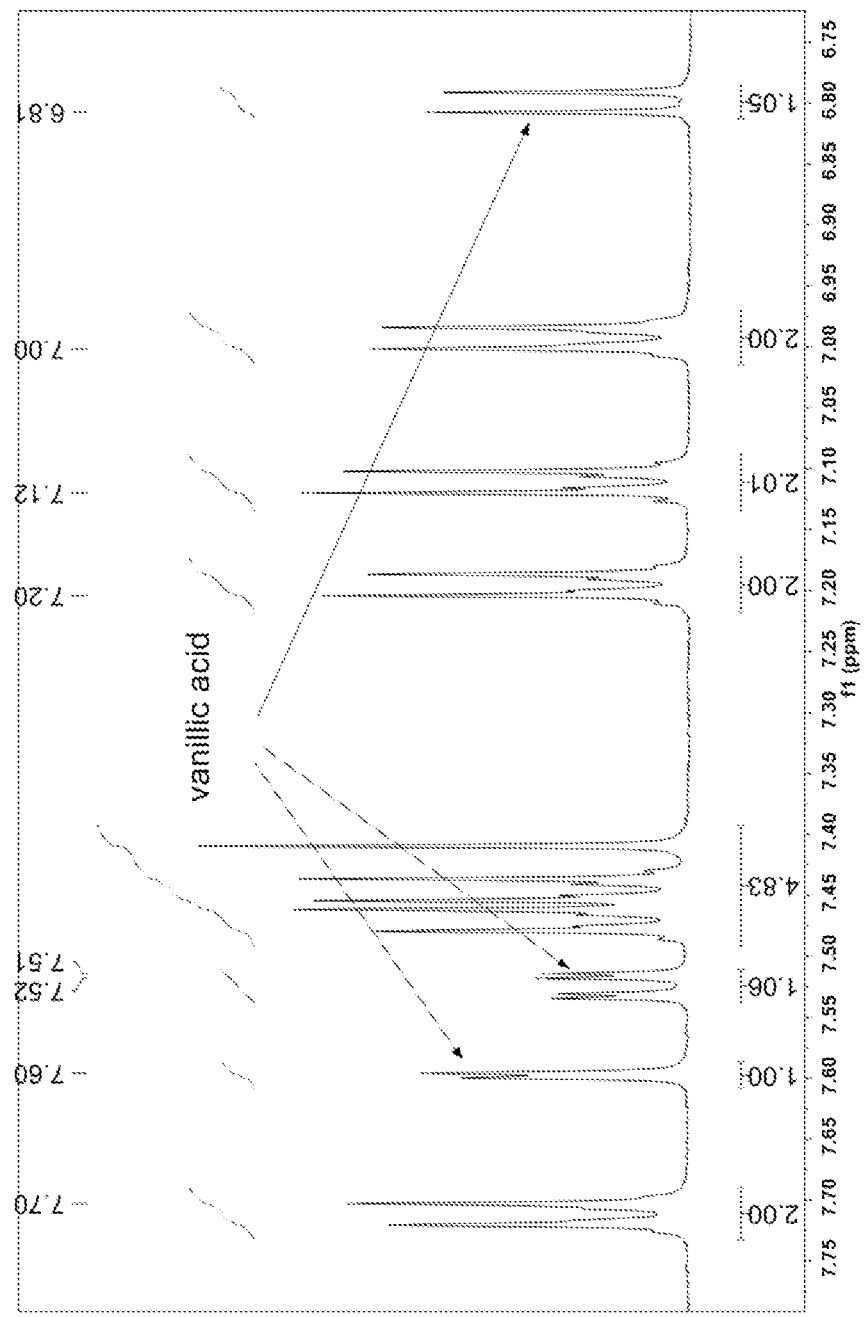
FIG. 5 is a $^1$H NMR spectrum of vanillate Type A.
Figure 6:
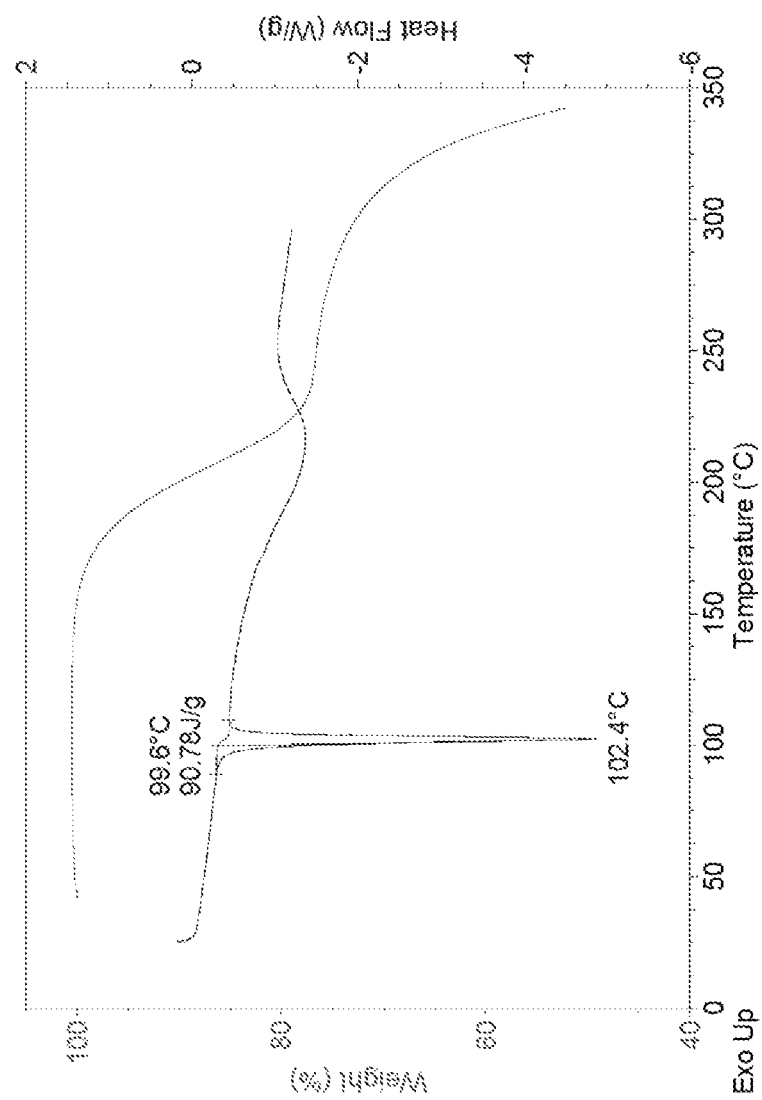
FIG. 6 is a DSC profile and a TGA of vanillate Type A.

In one aspect of the invention, the pharmaceutically acceptable salt of COMPOUND I is a vanillate. In one embodiment, the vanillate is crystalline. In one embodiment, the vanillate is crystalline and is characterized by an XRPD pattern having peaks at 2θ angles of 7.6°, 15.2°, and 18.2±0.2°. In one embodiment, the vanillate is crystalline and is characterized by an XRPD pattern having peaks at 2θ angles of 7.6°, 15.2°, 18.2°, 19.5°, and 22.1°±0.2°. In one embodiment, the vanillate is crystalline and is characterized by an XRPD pattern as shown in FIG. 4. In one embodiment, the vanillate is crystalline and is characterized by a $^1$H-NMR substantially similar to FIG. 5. In one embodiment, the vanillate is crystalline and is characterized by an endothermic peak at about 102° C. as determined by DSC. In one embodiment, the vanillate is crystalline and is characterized by a DSC profile as shown in FIG. 6. In one embodiment, the vanillate is crystalline and is characterized by a TGA profile as shown in FIG. 6. In one embodiment, the vanillate is crystalline and is characterized by at least two of the following features (I-i)-(I-iv):

(I-i) an XRPD pattern having peaks at 2θ angles of 7.6°, 15.2°, and 18.2°±0.2;
(I-i) a $^1$H-NMR substantially similar to FIG. 5;
(I-iii) a DSC profile as shown in FIG. 6; or
(I-iv) a TGA profile as shown in FIG. 6.

In one embodiment, the vanillate is crystalline and is vanillate Type A.

Vanillate Type A is characterized by the following XRPD pattern expressed in terms of the degree 2θ and relative intensities:

| Angle (Degree 2θ) | Relative Intensity* % |
|---|---|
| 3.8 | 55.81 |
| 7.6 | 100.0 |
| 10.1 | 27.15 |
| 11.4 | 34.78 |
| 12.5 | 10.28 |
| 13.8 | 35.17 |
| 15.2 | 75.86 |
| 16.7 | 5.98 |
| 18.2 | 92.26 |
| 19.3 | 26.57 |
| 19.5 | 41.91 |
| 19.9 | 42.60 |
| 20.7 | 46.33 |
| 22.1 | 72.93 |
| 23.0 | 18.87 |
| 23.3 | 21.12 |
| 23.7 | 25.69 |
| 24.0 | 16.07 |
| 25.1 | 7.33 |
| 26.9 | 24.16 |
| 28.1 | 7.10 |
| 29.0 | 3.58 |

-continued

| Angle (Degree 2θ) | Relative Intensity* % |
|---|---|
| 30.9 | 9.64 |
| 32.1 | 5.49 |

*The relative intensities may change depending on the crystal size and morphology.

Figure 54:
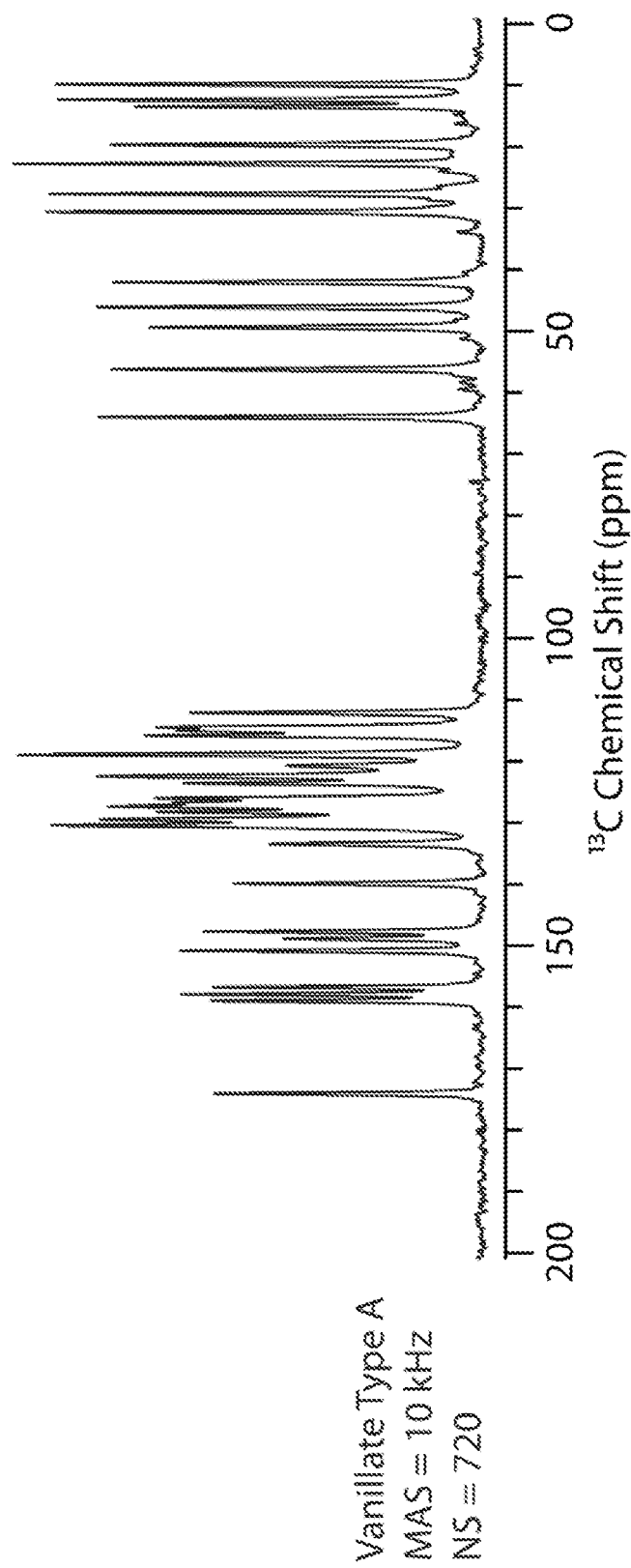
FIG. 54 is a $^{13}$C SSNMR spectrum of vanillate Type A.

In one embodiment, vanillate Type A is characterized by the SSNMR of FIG. 54. In one embodiment, vanillate Type A is characterized by the following $^{13}$C Solid State NMR shifts.

| ν(F1) [ppm] | Intensity [abs] |
|---|---|
| 173.98 | 518764942 |
| 158.90 | 523701406 |
| 157.82 | 581163758 |
| 156.66 | 520695138 |
| 150.75 | 583602098 |
| 148.77 | 383137046 |
| 147.63 | 537285852 |
| 139.80 | 479295068 |
| 133.36 | 409455758 |
| 130.34 | 834300332 |
| 129.37 | 738492624 |
| 128.15 | 628316020 |
| 127.25 | 722442494 |
| 126.68 | 597689492 |
| 125.91 | 632181896 |
| 123.50 | 576233614 |
| 122.37 | 746457612 |
| 120.63 | 377266908 |
| 118.84 | 899379890 |
| 115.73 | 651416188 |
| 114.89 | 590719488 |
| 114.38 | 629966434 |
| 112.02 | 565673488 |
| 74.41 | 22926046 |
| 63.90 | 742342396 |
| 59.36 | 42932124 |
| 58.23 | 40969420 |
| 56.12 | 717241560 |
| 51.19 | 39782202 |
| 49.28 | 642477890 |
| 48.09 | 52455602 |
| 46.01 | 744612974 |
| 43.27 | 26325990 |
| 41.94 | 713626906 |
| 40.30 | 35094498 |
| 33.78 | 47123722 |
| 30.51 | 846036976 |
| 28.55 | 103027634 |
| 27.61 | 836816524 |
| 26.34 | 84758562 |
| 23.94 | 80577642 |
| 21.02 | 59026588 |
| 19.57 | 718445114 |
| 18.34 | 40213720 |
| 16.17 | 49762848 |
| 14.71 | 52960880 |
| 13.38 | 670003710 |
| 12.26 | 820796130 |
| 9.76 | 824675266 |

Representative $^{13}$C NMR chemical shifts for vanillate Type A are 130.34, 118.84, 30.51, and 9.76 ppm. Representative $^{13}$C NMR chemical shifts for vanillate Type A are also 130.34, and 118.84 ppm.

Hydrochloride

Figure 7:
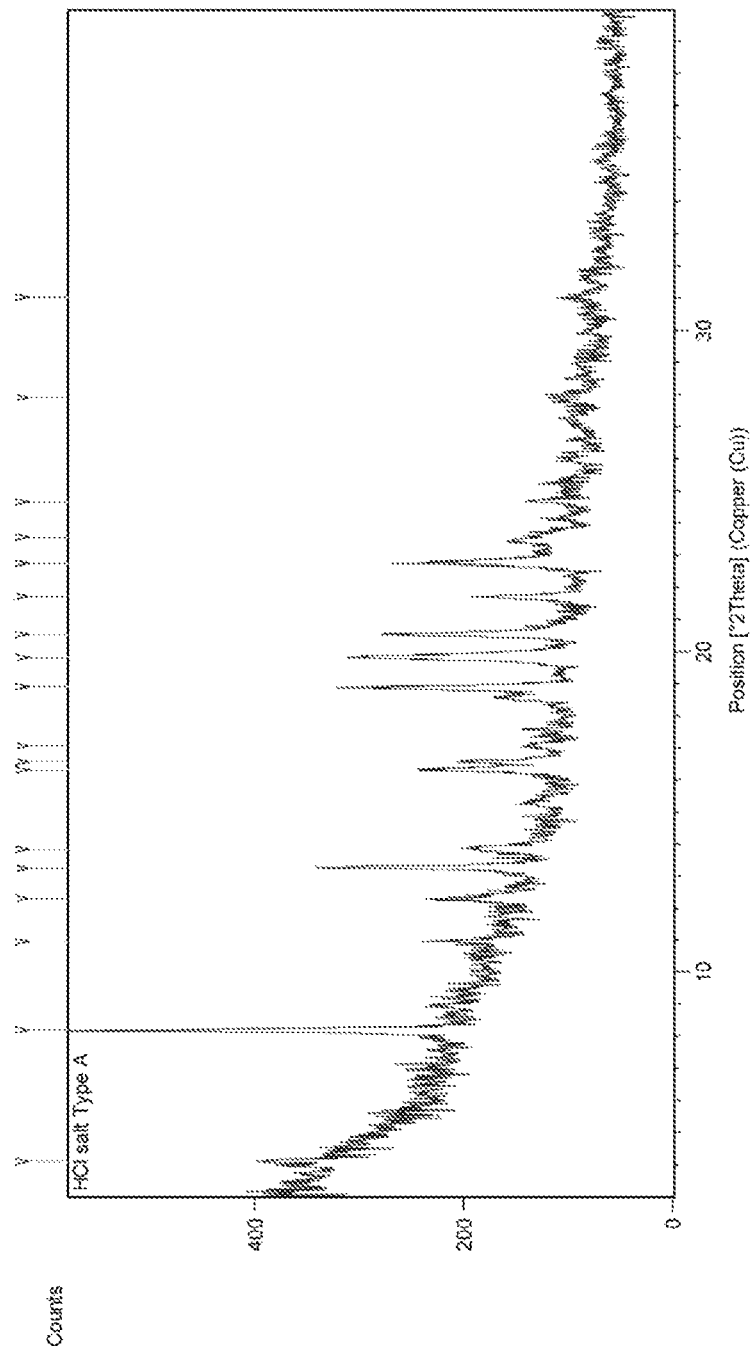
FIG. 7 is a XRPD Pattern of HCl Type A.
Figure 8:
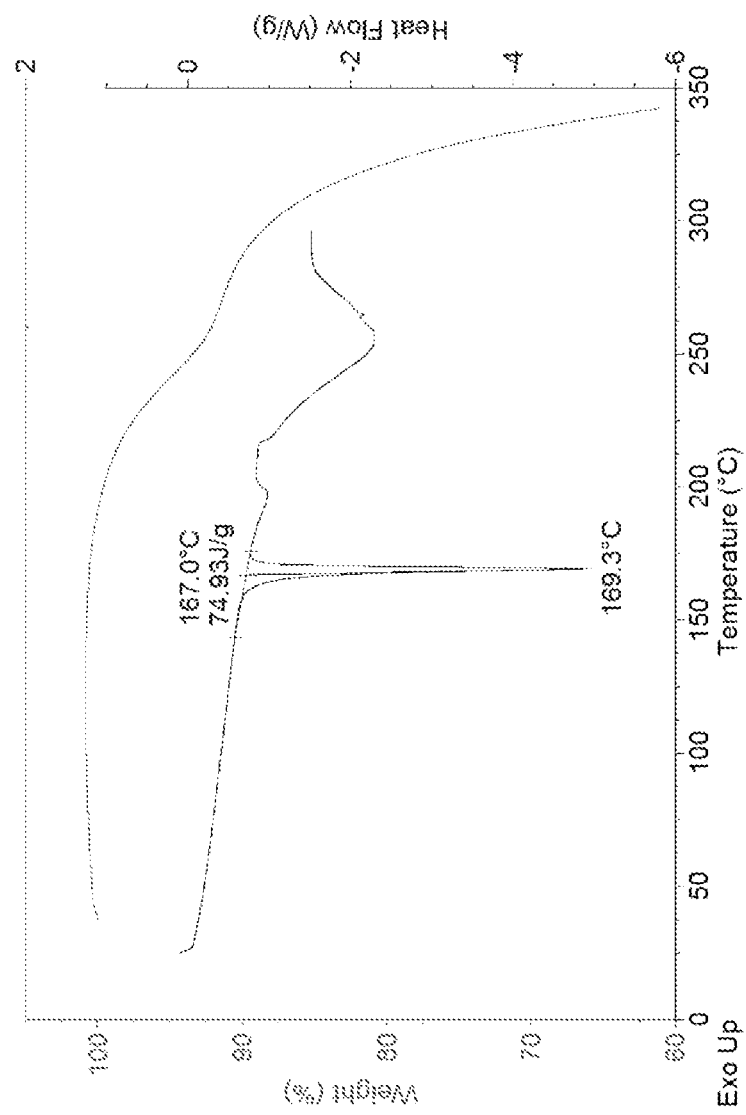
FIG. 8 is a DSC profile and a TGA of HCl Type A.

In one aspect of the invention, the pharmaceutically acceptable salt of COMPOUND I is a hydrochloride. In one embodiment, the pharmaceutically acceptable salt of COMPOUND I is a mono-hydrochloride. In one embodiment, the hydrochloride is crystalline. In one embodiment, the hydrochloride is crystalline and is characterized by an XRPD pattern having peaks at 2θ angles of 8.2°, 13.2°, and 19.8±0.2°. In one embodiment, the hydrochloride is crystalline and is characterized by an XRPD pattern having peaks at 2θ angles of 8.2°, 13.2°, 18.9°, 19.8°, and 22.8±0.2°. In one embodiment, the hydrochloride is crystalline and is characterized by an XRPD pattern as shown in FIG. 7. In one embodiment, the hydrochloride is crystalline and is characterized by an endothermic peak at about 169° C. as determined by DSC. In one embodiment, the hydrochloride is crystalline and is characterized by a DSC profile as shown in FIG. 8. In one embodiment, the hydrochloride is crystalline and is characterized by a TGA profile as shown in FIG. 8. In one embodiment, the hydrochloride is crystalline and is characterized by at least two of the following features (I-i)-(I-ii):

(I-i) an XRPD pattern having peaks at 2θ angles of 8.2°, 13.2°, and 19.8±0.2°;
(I-i) a DSC profile as shown in FIG. 8; or
(I-iii) a TGA profile as shown in FIG. 8.

In one embodiment, the hydrochloride is crystalline and is hydrochloride Type A.

Hydrochloride Type A is characterized by the following XRPD pattern expressed in terms of the degree 2θ and relative intensities:

| Angle (Degree 2θ) | Relative Intensity* % |
|---|---|
| 4.1 | 34.39 |
| 8.2 | 100.00 |
| 11.0 | 12.55 |
| 12.3 | 17.46 |
| 13.2 | 50.57 |
| 13.8 | 17.16 |
| 16.3 | 33.44 |
| 16.6 | 24.68 |
| 17.1 | 8.10 |
| 18.9 | 49.53 |
| 19.8 | 55.12 |
| 20.5 | 47.14 |
| 21.7 | 23.67 |
| 22.8 | 40.18 |
| 23.5 | 13.03 |
| 24.7 | 13.17 |
| 27.9 | 8.85 |
| 31.0 | 6.39 |

*The relative intensities may change depending on the crystal size and morphology.

Figure 55:
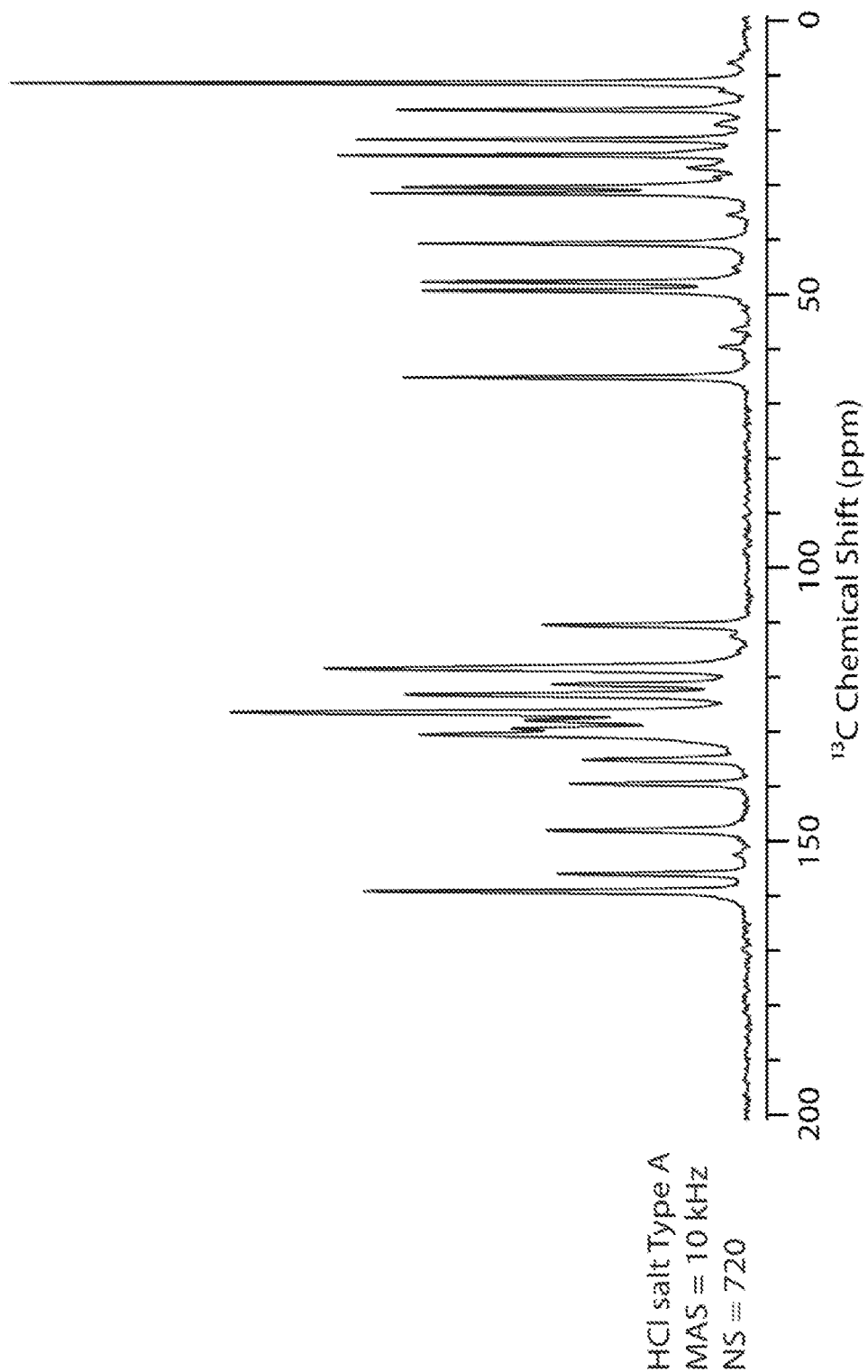
FIG. 55 is a $^{13}$C SSNMR spectrum of HCl Type A.

In one embodiment, hydrochloride Type A is characterized by the SSNMR of FIG. 55. In one embodiment, hydrochloride Type A is characterized by the following $^{13}$C Solid State NMR shifts.

| ν(F1) [ppm] | Intensity [abs] |
|---|---|
| 159.10 | 953088232 |
| 155.95 | 470291704 |
| 152.44 | 33462884 |
| 147.99 | 499499732 |
| 139.45 | 439571752 |
| 135.05 | 408089084 |
| 130.45 | 814303348 |
| 129.36 | 583614576 |
| 127.85 | 551091828 |
| 126.39 | 1286412804 |
| 123.15 | 851423168 |
| 121.28 | 483568508 |
| 118.41 | 1053112964 |
| 112.55 | 39828532 |
| 110.40 | 508450580 |

| v(F1) [ppm] | Intensity [abs] |
|---|---|
| 65.15 | 854300372 |
| 59.54 | 66691716 |
| 56.39 | 36621016 |
| 49.29 | 808691936 |
| 47.68 | 810682860 |
| 45.58 | 25808700 |
| 45.06 | 35072884 |
| 42.05 | 30969996 |
| 40.66 | 816438388 |
| 35.45 | 47738516 |
| 31.49 | 934947908 |
| 30.34 | 858474040 |
| 28.53 | 82699612 |
| 26.83 | 148201316 |
| 24.52 | 1018830360 |
| 21.63 | 971729684 |
| 18.99 | 80030488 |
| 16.21 | 870673752 |
| 12.83 | 68406912 |
| 11.30 | 1837080152 |
| 7.69 | 45668424 |

Representative $^{13}$C NMR chemical shifts for hydrochloride Type A are 126.39, 118.41, 31.49, and 11.30 ppm. Representative $^{13}$C NMR chemical shifts for hydrochloride Type A are also 126.39 and 118.41 ppm.

Figure 10:
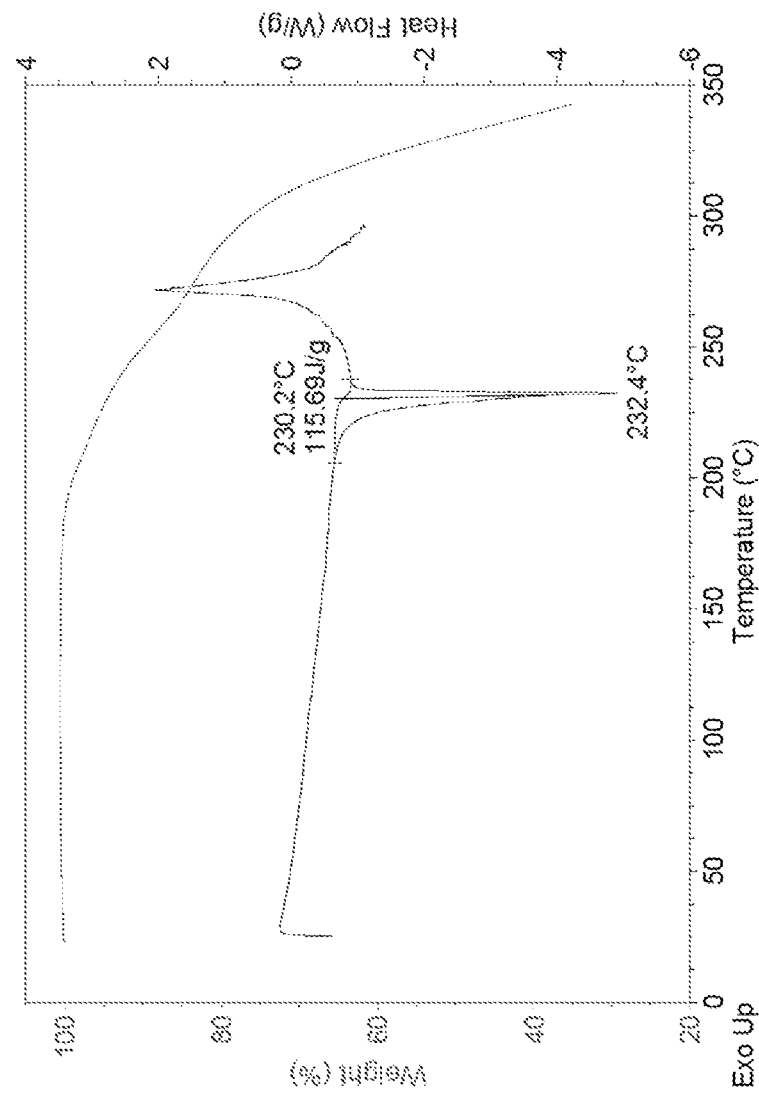
FIG. 10 is a DSC profile and a TGA of HCl Type B.

In one embodiment, the pharmaceutically acceptable salt of COMPOUND I is a dihydrochloride. In one embodiment, the hydrochloride is crystalline and is characterized by an XRPD pattern having peaks at 2θ angles of 9.1°, 14.1°, and 20.9±0.2°. In one embodiment, the hydrochloride is crystalline and is characterized by an XRPD pattern having peaks at 2θ angles of 9.1°, 14.1°, 18.4°, 20.9°, and 24.9±0.2°. In one embodiment, the hydrochloride is crystalline and is characterized by an XRPD pattern as shown in FIG. 8. In one embodiment, the hydrochloride is crystalline and is characterized by an endothermic peak at about 232° C. as determined by DSC. In one embodiment, the hydrochloride is crystalline and is characterized by a DSC profile as shown in FIG. 10. In one embodiment, the hydrochloride is crystalline and is characterized by a TGA profile as shown in FIG. 10. In one embodiment, the hydrochloride is crystalline and is characterized by at least two of the following features (I-i)-(I-ii):

(I-i) an XRPD pattern having peaks at 2θ angles of 9.1°, 14.1°, and 20.9±0.2°;
(I-i) a DSC profile as shown in FIG. 10; or
(I-iii) a TGA profile as shown in FIG. 10.

In one embodiment, the hydrochloride is crystalline and is hydrochloride Type B.

Hydrochloride Type B is characterized by the following XRPD pattern expressed in terms of the degree 2θ and relative intensities:

| Angle (Degree 2θ) | Relative Intensity* % |
|---|---|
| 7.3 | 13.98 |
| 9.1 | 51.22 |
| 10.6 | 33.70 |
| 12.5 | 34.00 |
| 14.1 | 100.00 |
| 15.5 | 24.94 |
| 16.3 | 14.38 |
| 17.1 | 10.39 |
| 18.4 | 44.36 |
| 19.7 | 20.58 |
| 20.5 | 43.45 |
| 20.8 | 56.05 |
| 22.1 | 11.12 |
| 22.6 | 27.31 |
| 23.0 | 33.90 |
| 23.3 | 37.34 |
| 24.9 | 48.11 |
| 25.6 | 9.27 |
| 26.5 | 14.44 |
| 27.4 | 29.41 |
| 28.1 | 9.66 |
| 31.2 | 7.92 |

*The relative intensities may change depending on the crystal size and morphology.

Figure 56:
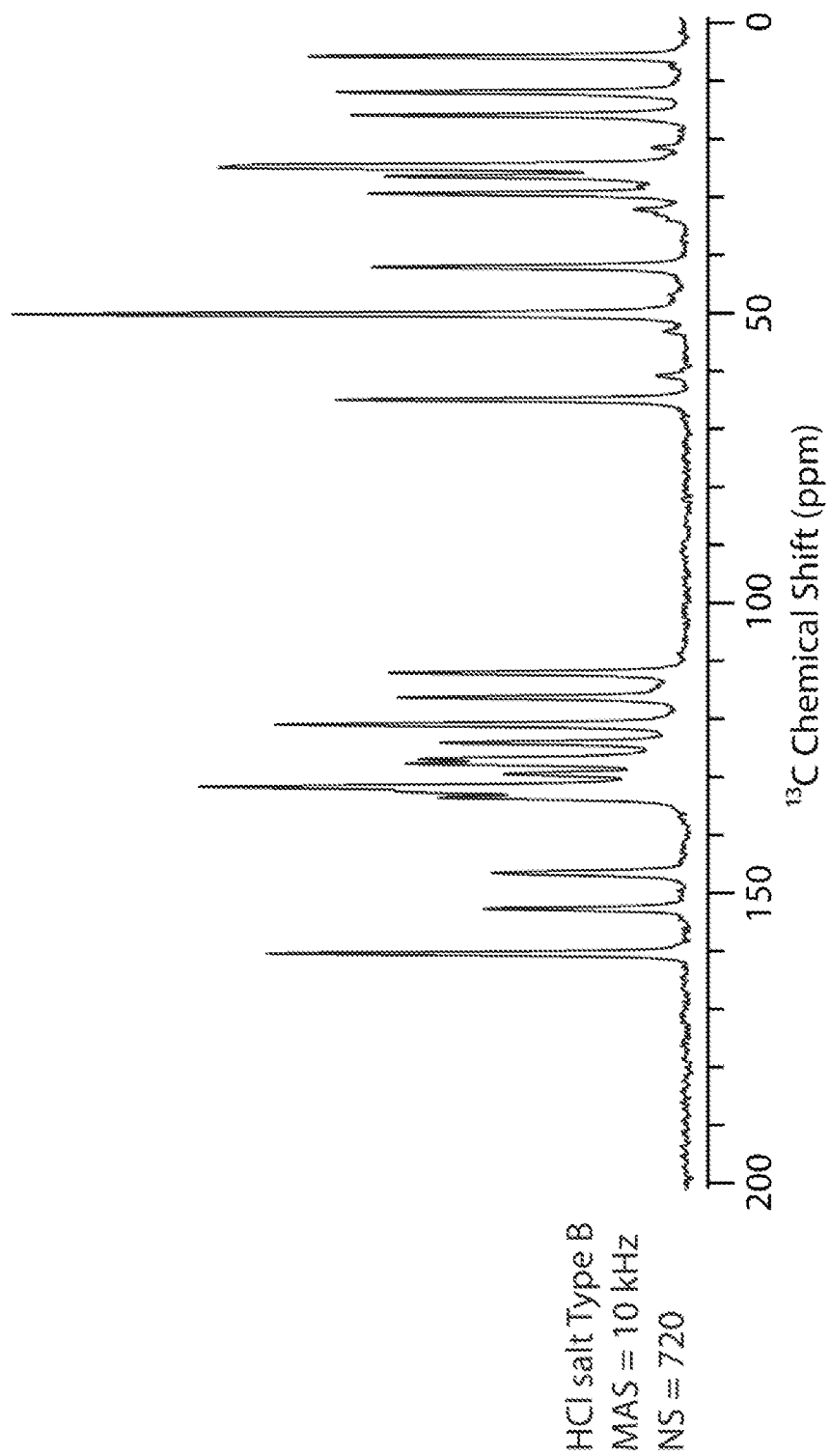
FIG. 56 is a $^{13}$C SSNMR spectrum of HCl Type B.

In one embodiment, hydrochloride Type B is characterized by the SSNMR of FIG. 56. In one embodiment, hydrochloride Type B is characterized by the following $^{13}$C Solid State NMR shifts.

| v(F1) [ppm] | Intensity [abs] |
|---|---|
| 160.38 | 862337248 |
| 152.68 | 415541376 |
| 146.50 | 398229180 |
| 133.48 | 509664308 |
| 131.64 | 1002500776 |
| 129.44 | 375056764 |
| 127.61 | 577710608 |
| 126.83 | 549811320 |
| 124.05 | 506963980 |
| 120.91 | 845008256 |
| 116.23 | 593691116 |
| 114.08 | 60401440 |
| 112.00 | 611713568 |
| 64.90 | 719229808 |
| 60.85 | 60487620 |
| 53.08 | 45413648 |
| 50.16 | 1388490728 |
| 42.00 | 646152528 |
| 33.90 | 39139876 |
| 32.84 | 63679432 |
| 32.10 | 107556548 |
| 29.35 | 653618160 |
| 28.09 | 99347784 |
| 26.38 | 618979488 |
| 24.89 | 963423320 |
| 24.53 | 937008992 |
| 21.46 | 68970164 |
| 15.84 | 691234676 |
| 11.85 | 719533460 |
| 5.71 | 777140968 |

Representative $^{13}$C NMR chemical shifts for hydrochloride Type B are 131.64, 120.91, 50.16, and 24.89 ppm. Representative $^{13}$C NMR chemical shifts for hydrochloride Type B are also 131.64 and 120.91 ppm.

Fumarate

Figure 11:
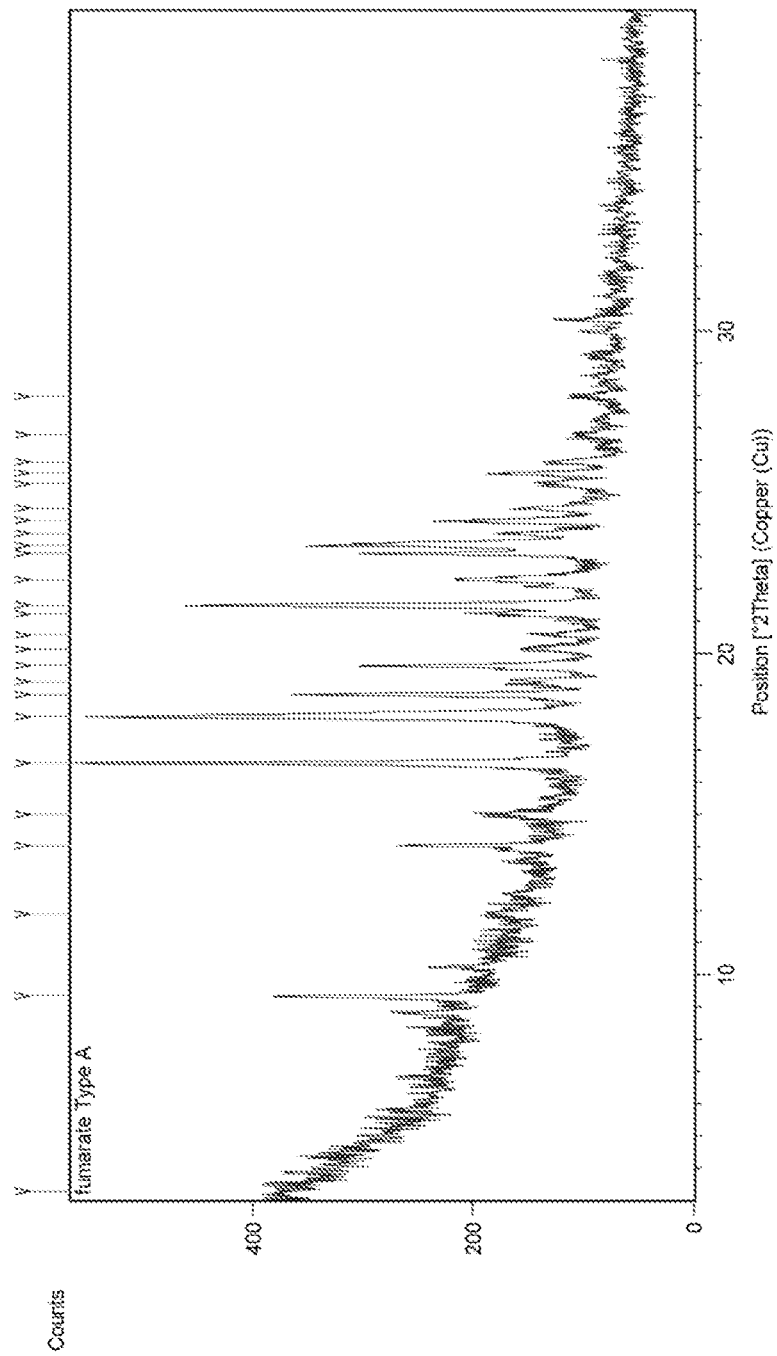
FIG. 11 is a XRPD Pattern of fumarate Type A.
Figure 12:
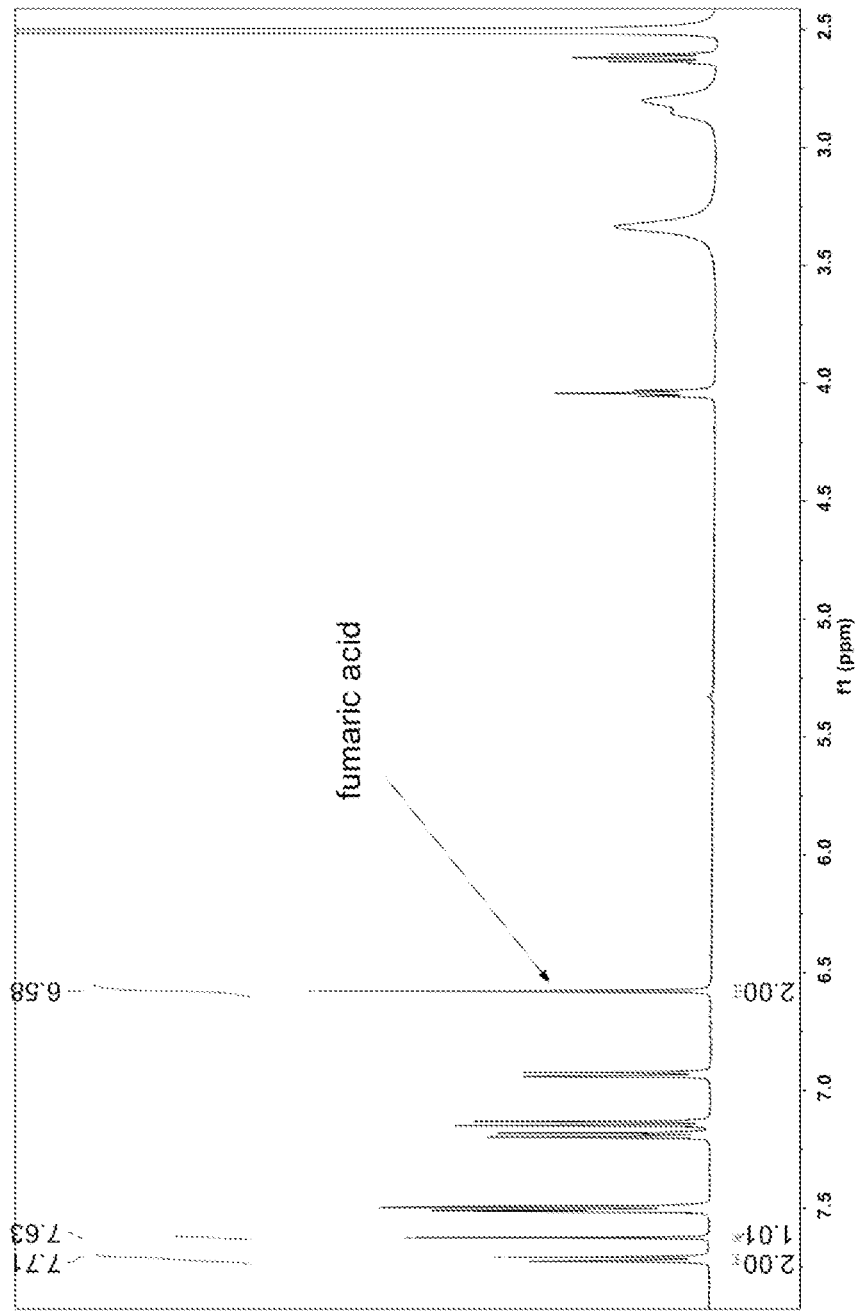
FIG. 12 is a $^1$H NMR spectrum of fumarate Type A.
Figure 13:
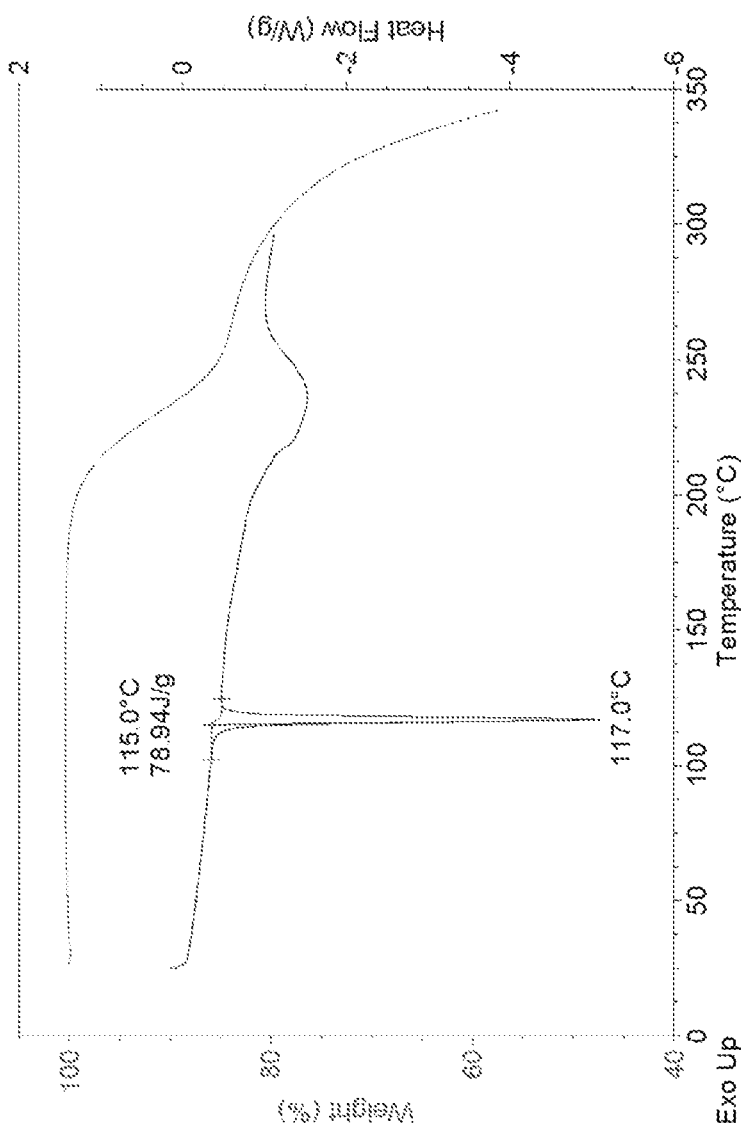
FIG. 13 is a DSC profile and a TGA of fumarate Type A.

In one aspect of the invention, the pharmaceutically acceptable salt of COMPOUND I is a fumarate. In one embodiment, the pharmaceutically acceptable salt of COMPOUND I is a monofumarate. In one embodiment, the fumarate is crystalline. In one embodiment, the fumarate is crystalline and is characterized by an XRPD pattern having peaks at 2θ angles of 16.6°, 18.0°, and 21.5±0.2°. In one embodiment, the fumarate is crystalline and is characterized by an XRPD pattern having peaks at 2θ angles of 9.4°, 16.6°, 18.0°, 18.7°, and 21.5±0.2°. In one embodiment, the fumarate is crystalline and is characterized by an XRPD pattern as shown in FIG. 11. In one embodiment, the fumarate is crystalline and is characterized by a $^1$H-NMR substantially similar to FIG. 12. In one embodiment, the fumarate is crystalline and is characterized by an endothermic peak at about 117° C. as determined by DSC. In one embodiment, the fumarate is crystalline and is characterized by a DSC profile as shown in FIG. 13. In one embodiment, the fumarate is crystalline and is characterized by a TGA profile as shown in FIG. 13. In one embodiment, the fumarate is crystalline and is characterized by at least two of the following features (I-i)-(I-iv):

(I-i) an XRPD pattern having peaks at 2θ angles of 16.6°, 18.0°, and 21.5±0.2°;
(I-i) a $^1$H-NMR substantially similar to FIG. 12;
(I-iii) a DSC profile as shown in FIG. 13; or
(I-iv) a TGA profile as shown in FIG. 13.

In one embodiment, the fumarate is crystalline and is fumarate Type A.

Fumarate Type A is characterized by the following XRPD pattern expressed in terms of the degree 2θ and relative intensities:

| Angle (Degree 2θ) | Relative Intensity* % |
|---|---|
| 3.3 | 19.86 |
| 9.4 | 40.40 |
| 11.9 | 5.53 |
| 14.0 | 29.68 |
| 15.0 | 10.67 |
| 16.6 | 100.00 |
| 18.0 | 98.18 |
| 18.7 | 57.31 |
| 19.1 | 10.05 |
| 19.6 | 44.12 |
| 20.1 | 11.84 |
| 20.6 | 8.06 |
| 21.2 | 20.89 |
| 21.5 | 73.12 |
| 22.3 | 27.71 |
| 23.1 | 45.65 |
| 23.3 | 58.90 |
| 23.7 | 19.73 |
| 24.1 | 26.80 |
| 24.5 | 16.11 |
| 25.3 | 11.25 |
| 25.6 | 20.62 |
| 26.0 | 11.36 |
| 26.8 | 5.52 |
| 28.0 | 6.17 |

*The relative intensities may change depending on the crystal size and morphology.

Figure 57:
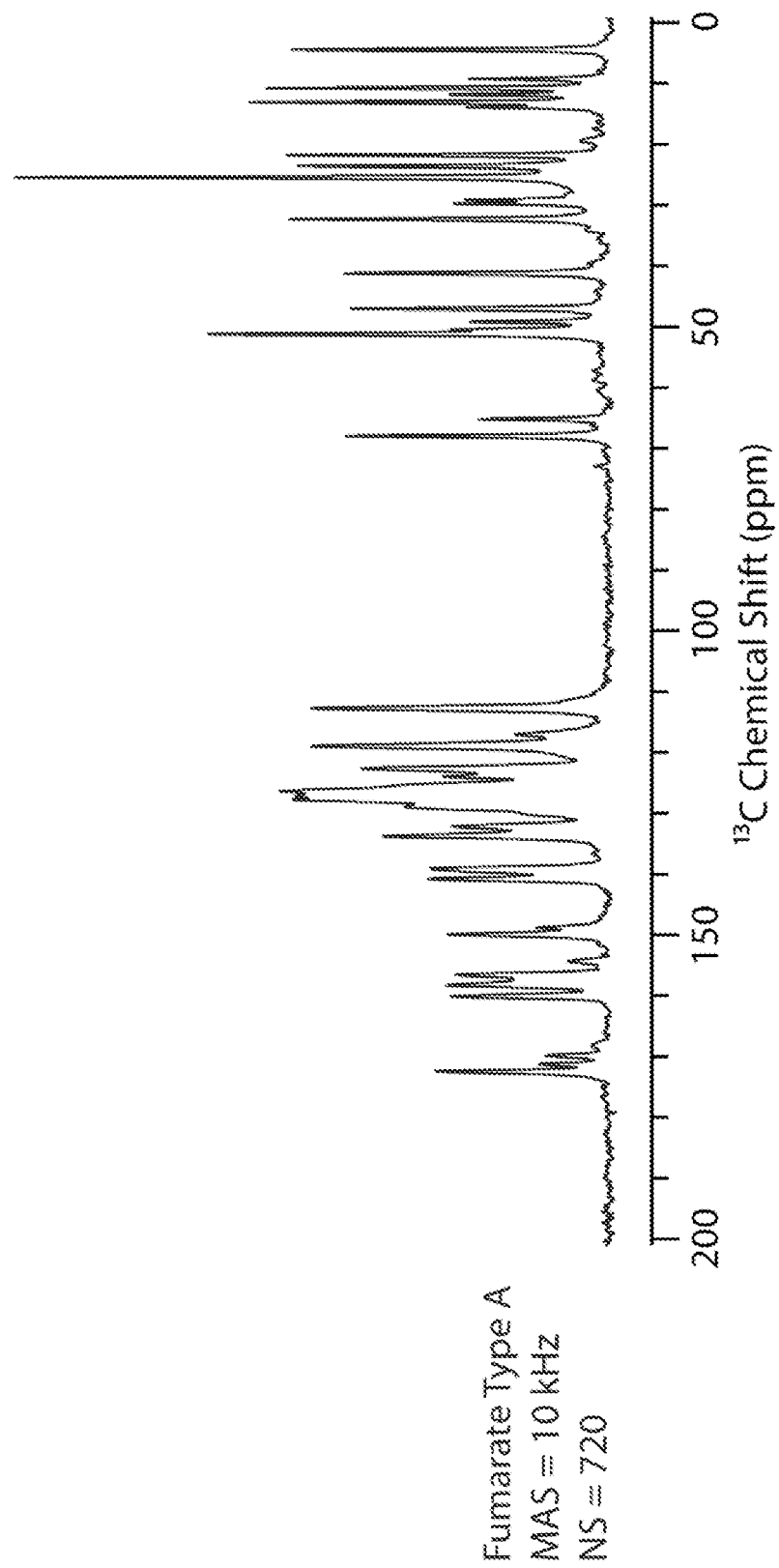
FIG. 57 is a $^{13}$C SSNMR spectrum of fumarate Type A.

In one embodiment, fumarate Type A is characterized by the SSNMR of FIG. 57. In one embodiment, fumarate Type A is characterized by the following $^{13}$C Solid State NMR shifts.

| v(F1) [ppm] | Intensity [abs] |
|---|---|
| 172.38 | 337267480 |
| 171.19 | 131627880 |
| 169.79 | 120497860 |
| 168.78 | 20841048 |
| 168.03 | 30857232 |
| 160.04 | 306524836 |
| 158.23 | 314618800 |
| 156.49 | 297296628 |
| 154.28 | 76593848 |
| 151.50 | 18476548 |
| 149.88 | 313323800 |
| 148.74 | 138099028 |
| 140.74 | 350685108 |
| 139.03 | 346931640 |

-continued

| v(F1) [ppm] | Intensity [abs] |
|---|---|
| 136.55 | 29037296 |
| 135.03 | 36086336 |
| 133.74 | 441091940 |
| 132.11 | 305069032 |
| 128.84 | 396232604 |
| 127.67 | 617794512 |
| 127.04 | 611242240 |
| 126.30 | 642727256 |
| 123.93 | 322306008 |
| 122.57 | 481668820 |
| 118.91 | 581671032 |
| 117.00 | 182375440 |
| 114.48 | 24623640 |
| 112.68 | 580902296 |
| 110.09 | 27131304 |
| 72.86 | 25288860 |
| 67.91 | 511952704 |
| 66.16 | 32567972 |
| 65.11 | 251125628 |
| 60.40 | 20306732 |
| 58.68 | 27378388 |
| 57.05 | 27546476 |
| 51.14 | 785416440 |
| 50.41 | 308814128 |
| 49.11 | 269126368 |
| 46.95 | 504166432 |
| 44.07 | 25520328 |
| 41.12 | 516904168 |
| 39.55 | 38578008 |
| 33.90 | 42940460 |
| 32.23 | 624448384 |
| 29.68 | 301783888 |
| 29.07 | 278305992 |
| 25.36 | 1163443304 |
| 23.53 | 608845616 |
| 21.72 | 629268860 |
| 19.45 | 53364496 |
| 17.35 | 27964284 |
| 16.15 | 20470736 |
| 13.84 | 276258676 |
| 12.99 | 701321012 |
| 11.75 | 309202864 |
| 10.66 | 669111516 |
| 9.18 | 271815232 |
| 4.37 | 618654332 |

Representative $^{13}$C NMR chemical shifts for fumarate Type A are 172.38, 126.3, 51.14, and 25.36 ppm. Representative $^{13}$C NMR chemical shifts for fumarate Type A are also 172.38 and 126.3 ppm.

Maleate

Figure 14:
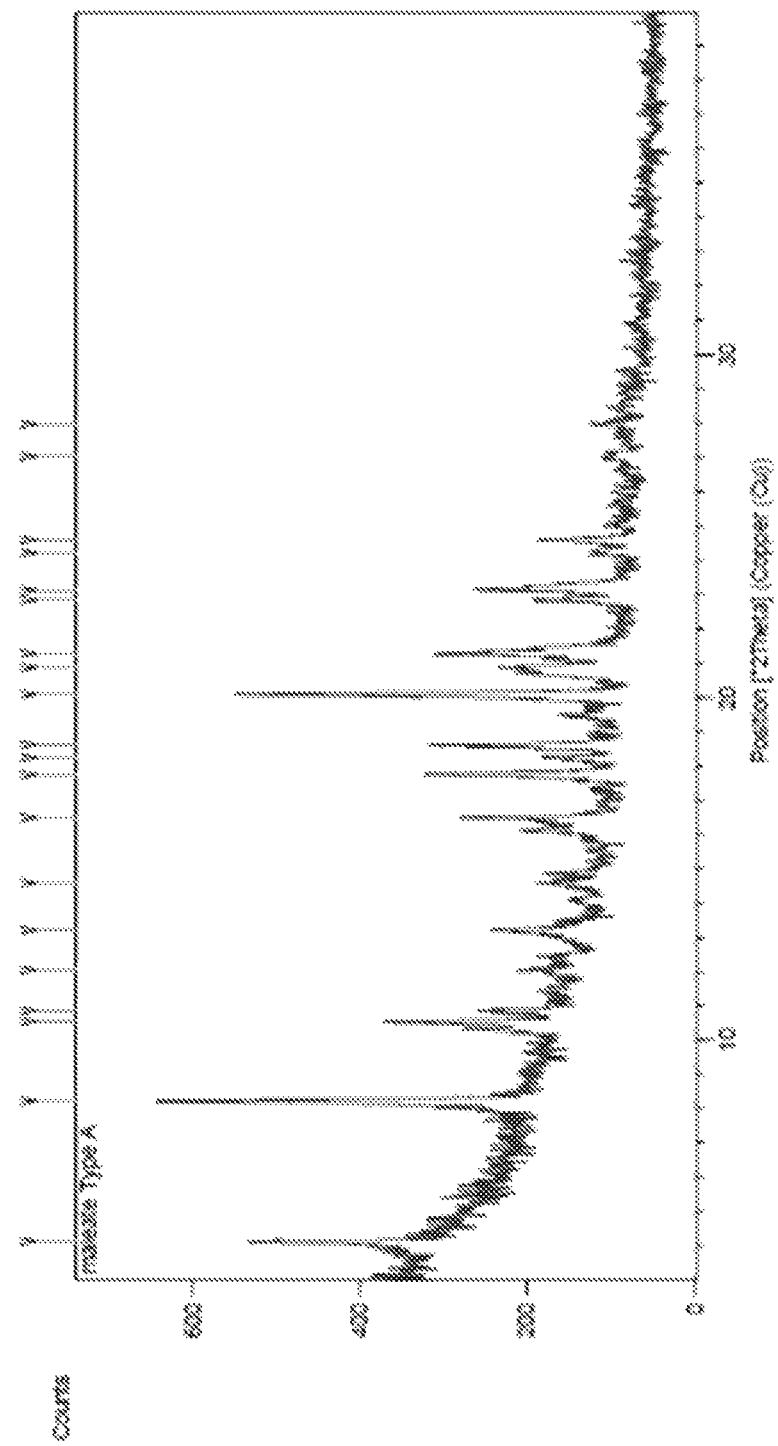
FIG. 14 is a XRPD Pattern of maleate Type A.
Figure 15:
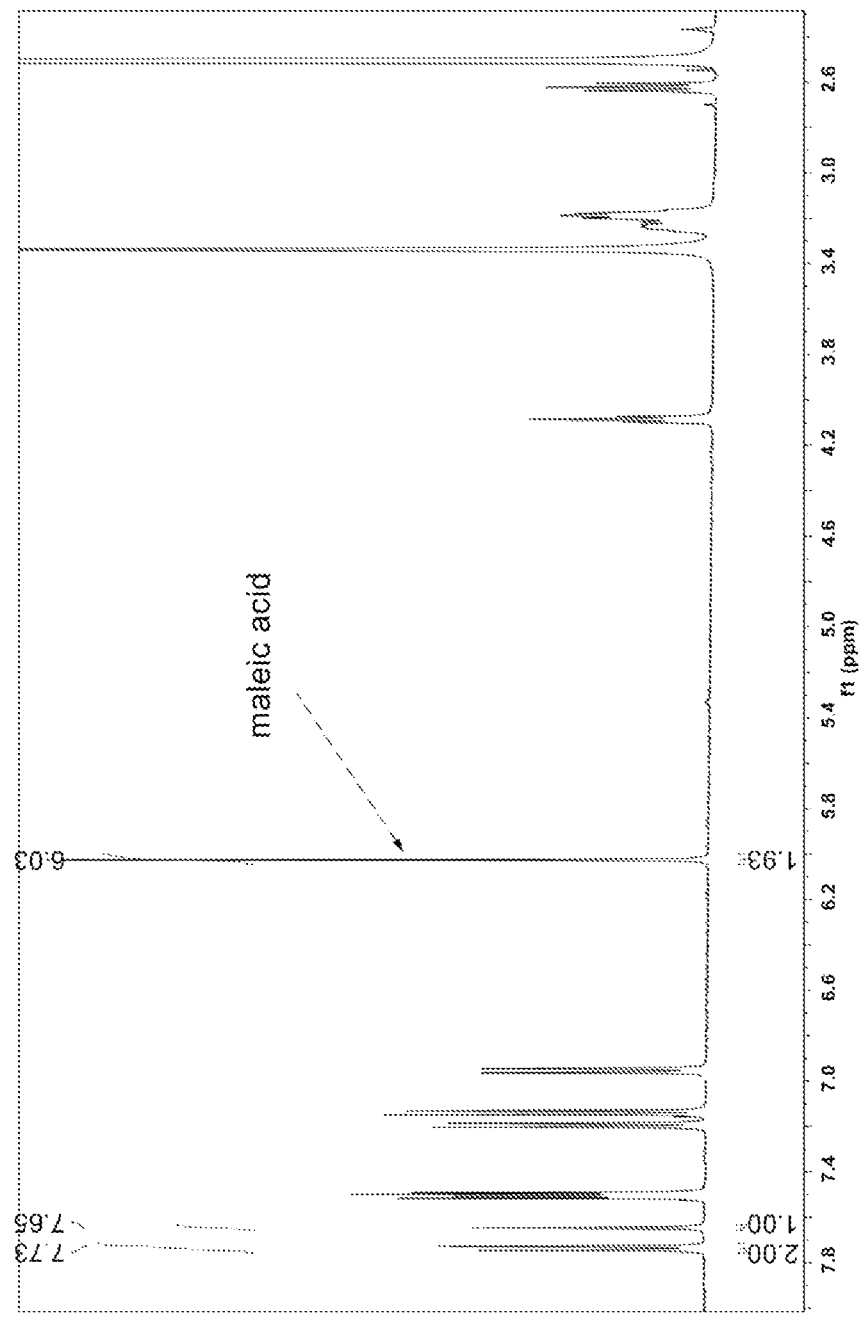
FIG. 15 is a $^1$H NMR spectrum of maleate Type A.
Figure 16:
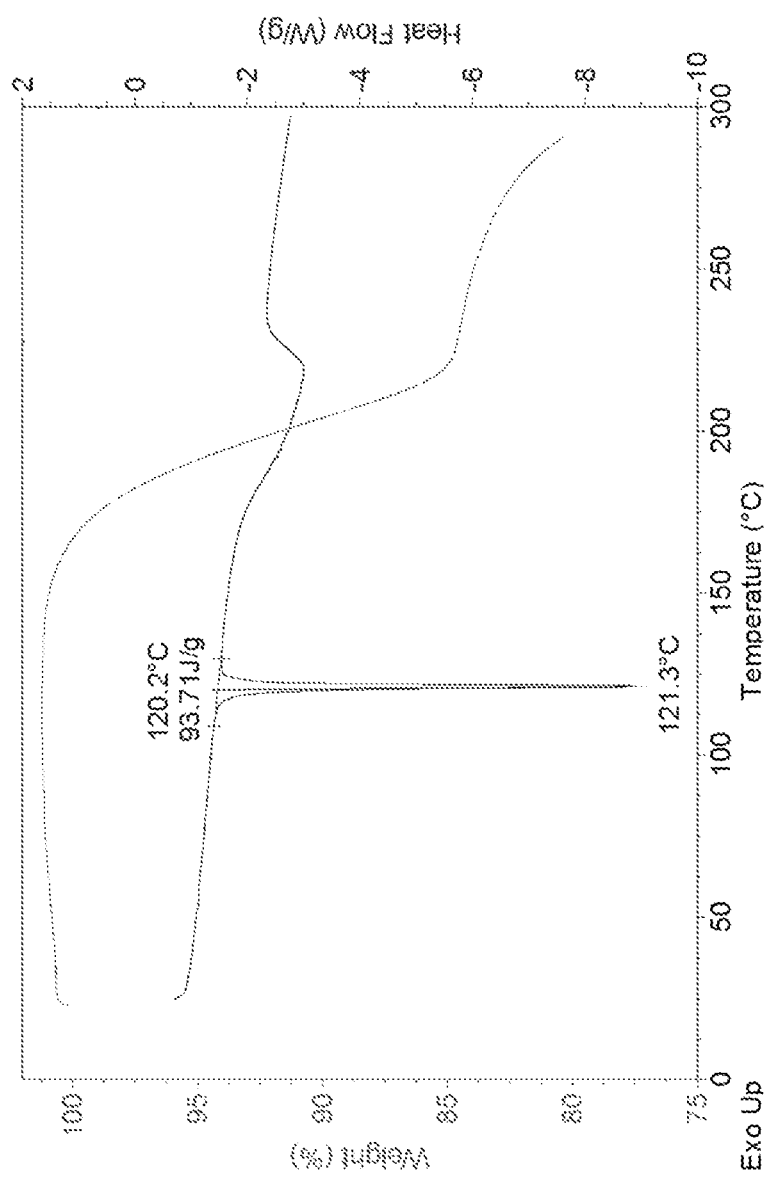
FIG. 16 is a DSC profile and a TGA of maleate Type A.

In one aspect of the invention, the pharmaceutically acceptable salt of COMPOUND I is a maleate. In one embodiment, the pharmaceutically acceptable salt of COMPOUND I is a mono-maleate. In one embodiment, the maleate is crystalline. In one embodiment, the maleate is crystalline and is characterized by an XRPD pattern having peaks at 2θ angles of 4.1°, 8.2°, and 20.1°±0.2°. In one embodiment, the maleate is crystalline and is characterized by an XRPD pattern having peaks at 2θ angles of 4.1°, 8.2°, 17.7°, and 20.1°±0.2°. In one embodiment, the maleate is crystalline and is characterized by an XRPD pattern as shown in FIG. 14. In one embodiment, the maleate is crystalline and is characterized by a $^1$H-NMR substantially similar to FIG. 15. In one embodiment, the maleate is crystalline and is characterized by an endothermic peak at about 121° C. as determined by DSC. In one embodiment, the maleate is crystalline and is characterized by a DSC profile as shown in FIG. 16. In one embodiment, the maleate is crystalline and is characterized by a TGA profile as shown in FIG. 16. In one embodiment, the maleate is crystalline and is characterized by at least two of the following features (I-i)-(I-iv):

(I-i) an XRPD pattern having peaks at 2θ angles of 4.1°, 8.2°, and 20.1°±0.2°;
(I-ii) a ¹H-NMR substantially similar to FIG. 15;
(I-iii) a DSC profile as shown in FIG. 16; or
(I-iv) a TGA profile as shown in FIG. 16.

In one embodiment, the maleate is crystalline and is maleate Type A.

Maleate Type A is characterized by the following XRPD pattern expressed in terms of the degree 2θ and relative intensities:

| Angle (Degree 2θ) | Relative Intensity* % |
|---|---|
| 4.1 | 47.43 |
| 8.2 | 100.00 |
| 10.5 | 36.95 |
| 10.9 | 14.31 |
| 12.1 | 5.98 |
| 13.2 | 19.48 |
| 14.6 | 9.63 |
| 16.5 | 32.99 |
| 17.7 | 38.92 |
| 18.2 | 13.98 |
| 18.6 | 39.55 |
| 20.1 | 85.25 |
| 20.9 | 25.14 |
| 21.3 | 39.00 |
| 22.9 | 20.84 |
| 23.1 | 30.15 |
| 24.2 | 7.34 |
| 24.6 | 19.84 |
| 27.0 | 5.70 |
| 28.0 | 8.16 |

*The relative intensities may change depending on the crystal size and morphology.

Figure 58:
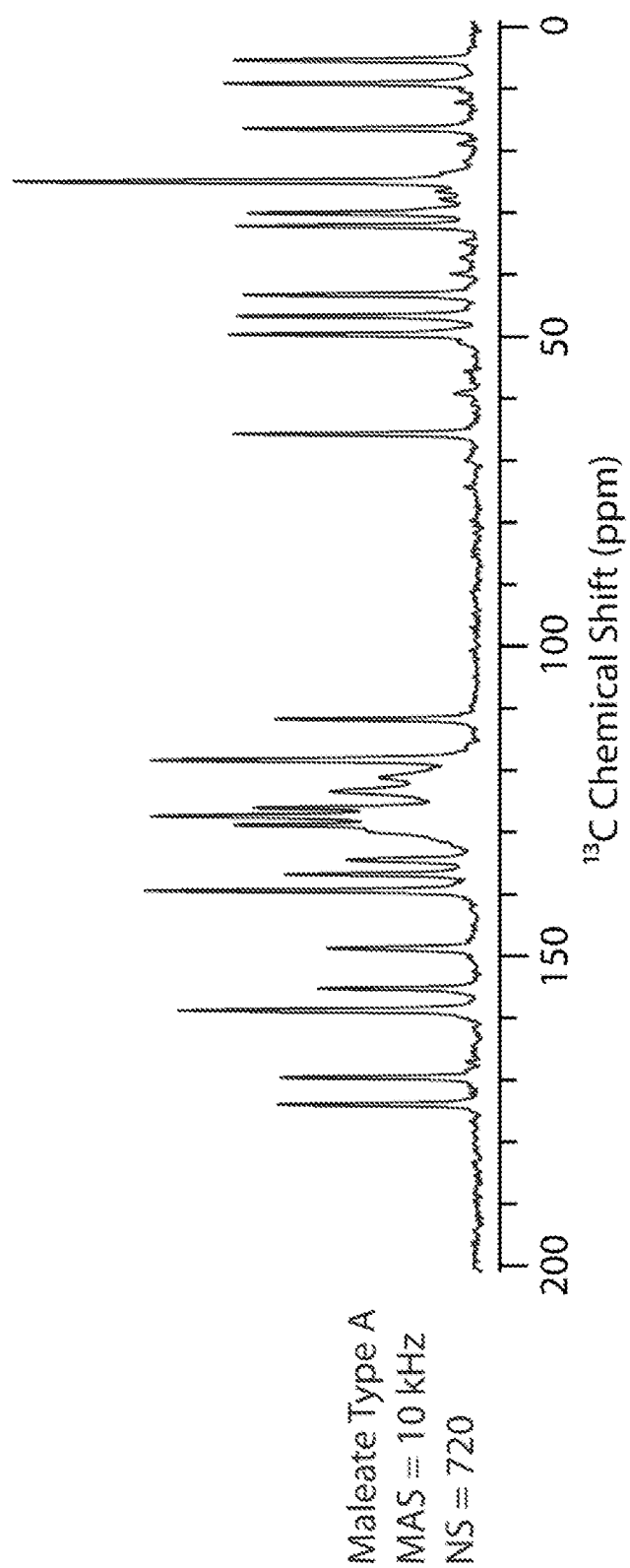
FIG. 58 is a $^{13}$C SSNMR spectrum of maleate Type A.

In one embodiment, maleate Type A is characterized by the SSNMR of FIG. 58. In one embodiment, maleate Type A is characterized by the following ¹³C Solid State NMR shifts.

| v(F1) [ppm] | Intensity [abs] |
|---|---|
| 173.90 | 380871702 |
| 169.54 | 374481920 |
| 158.71 | 572142114 |
| 155.21 | 303592386 |
| 148.72 | 286967840 |
| 139.40 | 636205362 |
| 137.83 | 30078406 |
| 136.75 | 365665738 |
| 134.41 | 247688192 |
| 128.81 | 465806822 |
| 127.34 | 623919564 |
| 126.01 | 426527498 |
| 123.41 | 280650582 |
| 121.12 | 184800890 |
| 118.33 | 623845994 |
| 111.71 | 385934770 |
| 74.23 | 21417096 |
| 69.97 | 20605302 |
| 65.68 | 464208928 |
| 59.18 | 41646048 |
| 55.59 | 20905118 |
| 50.89 | 33762238 |
| 50.63 | 35244932 |
| 49.61 | 473328878 |
| 46.66 | 458106712 |
| 43.22 | 445385924 |
| 39.80 | 47315182 |
| 37.20 | 28517076 |
| 34.72 | 29804692 |
| 32.08 | 459251190 |
| 30.01 | 438417502 |
| 27.77 | 69094248 |
| 26.51 | 75282636 |
| 24.93 | 889954400 |
| 23.56 | 68038434 |
| 21.62 | 22777942 |
| 18.87 | 32612590 |
| 16.37 | 446765060 |
| 15.30 | 25603280 |
| 12.19 | 40121854 |
| 10.18 | 30941316 |
| 9.09 | 483465274 |
| 5.36 | 463535446 |

Representative ¹³C NMR chemical shifts for maleate Type A are 139.40, 127.34, 118.33, and 24.93 ppm. Representative ¹³C NMR chemical shifts for maleate Type A are also 139.40, 127.34 and 118.33 ppm.

Galactarate

Figure 17:
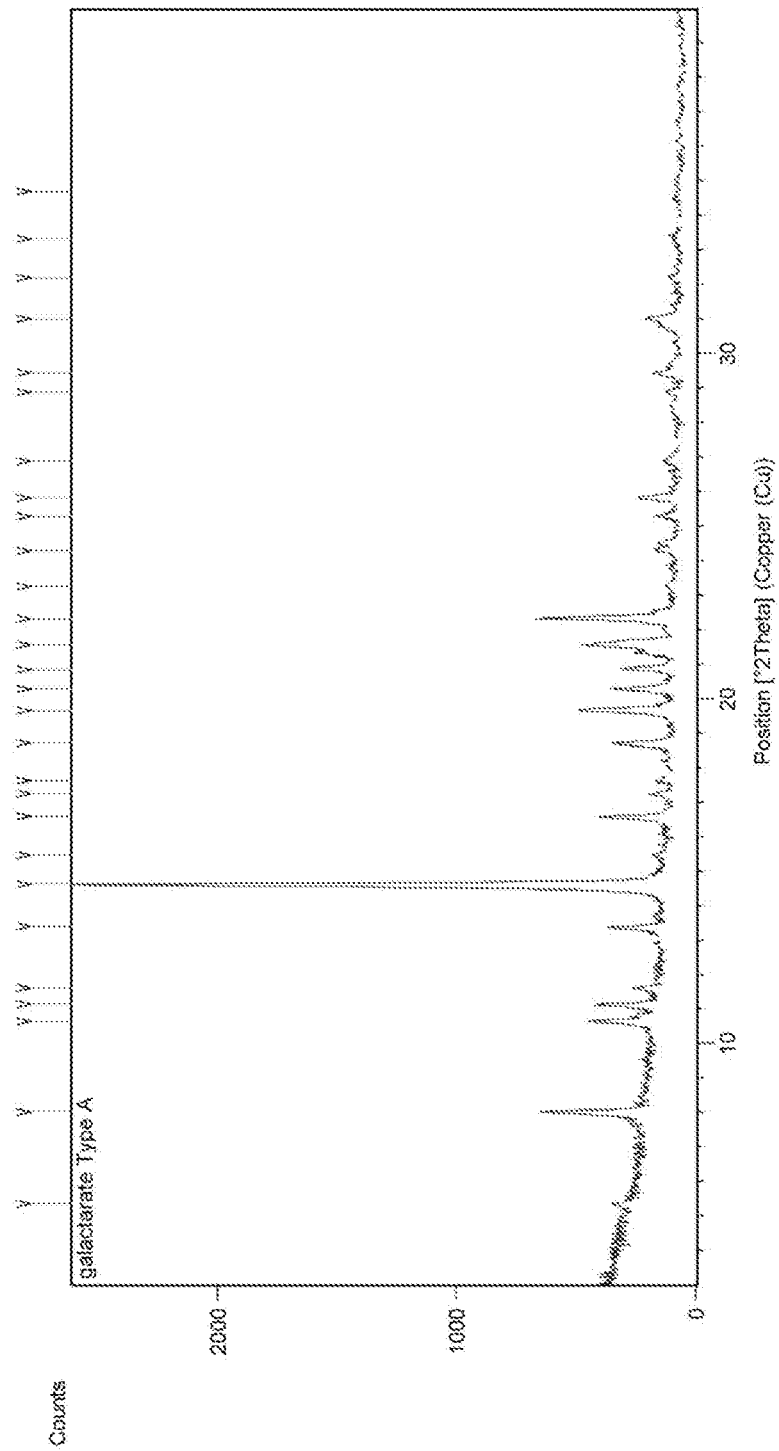
FIG. 17 is a XRPD Pattern of galactarate Type A.
Figure 18:
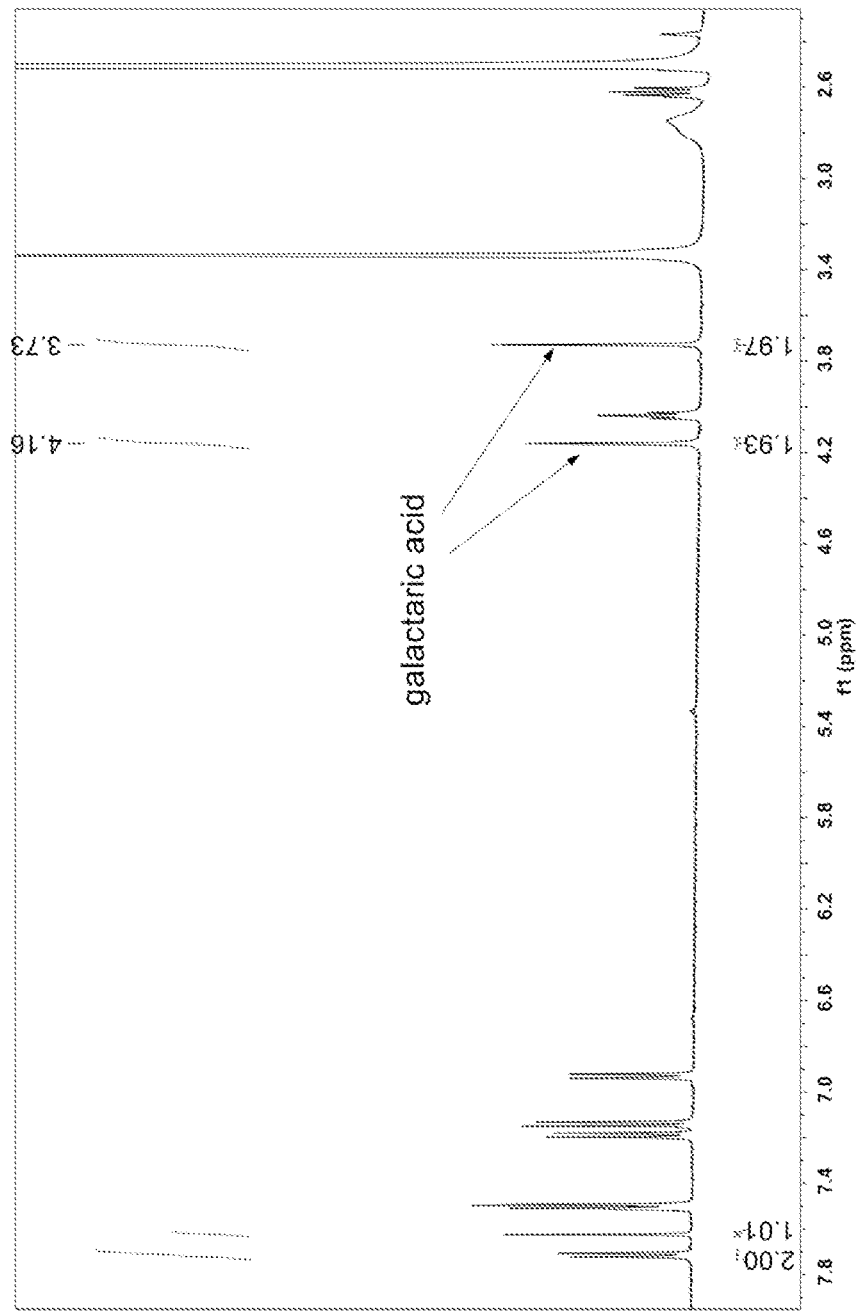
FIG. 18 is a $^1$H NMR spectrum of galactarate Type A.
Figure 19:
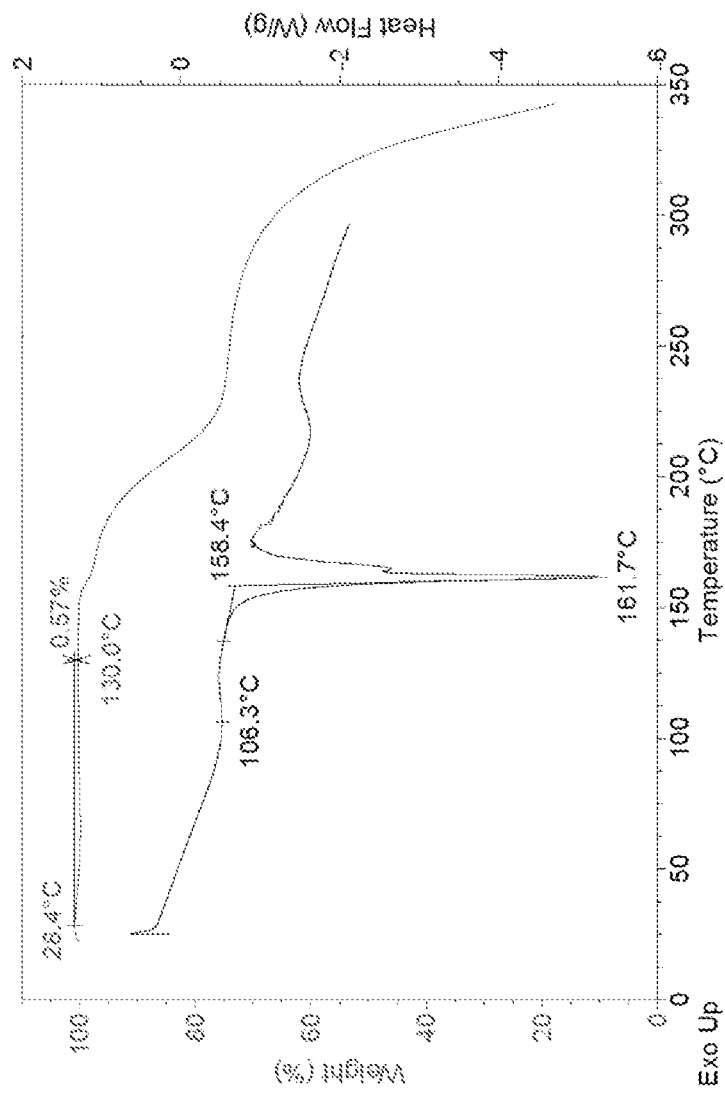
FIG. 19 is a DSC profile and a TGA of galactarate Type A.

In one aspect of the invention, the pharmaceutically acceptable salt of COMPOUND I is a galactarate. In one embodiment, the pharmaceutically acceptable salt of COMPOUND I is a mono-galactarate. In one embodiment, the galactarate is crystalline. In one embodiment, the galactarate is crystalline and is characterized by an XRPD pattern having peaks at 2θ angles of 8.0°, 14.6°, and 19.7±0.2°. In one embodiment, the galactarate is crystalline and is characterized by an XRPD pattern having peaks at 2θ angles of 8.0°, 14.6°, 19.7°, 21.5°, and 22.3±0.2°. In one embodiment, the galactarate is crystalline and is characterized by an XRPD pattern as shown in FIG. 17. In one embodiment, the galactarate is crystalline and is characterized by a ¹H-NMR substantially similar to FIG. 18. In one embodiment, the galactarate is crystalline and is characterized by an endothermic peak at about 106° C. and an endothermic peak at 162° C. as determined by DSC. In one embodiment, the galactarate is crystalline and is characterized by a DSC profile as shown in FIG. 19. In one embodiment, the galactarate is crystalline and characterized by an about 0.6 wt % loss between room temperature and about 130° C. as determined by TGA. In one embodiment, the galactarate is crystalline and is characterized by a TGA profile as shown in FIG. 19. In one embodiment, the galactarate is crystalline and is characterized by at least two of the following features (I-i)-(I-iv):

(I-i) an XRPD pattern having peaks at 2θ angles of 8.0°, 14.6°, and 19.7°±0.2°;
(I-i) a ¹H-NMR substantially similar to FIG. 18;
(I-iii) a DSC profile as shown in FIG. 19; or
(I-iv) a TGA profile as shown in FIG. 19.

In one embodiment, the galactarate is crystalline and is galactarate Type A.

Galactarate Type A is characterized by the following XRPD pattern expressed in terms of the degree 2θ and relative intensities:

| Angle (Degree 2θ) | Relative Intensity* % |
|---|---|
| 5.3 | 2.54 |
| 8.0 | 17.73 |
| 10.7 | 11.12 |
| 11.1 | 9.45 |
| 11.6 | 4.29 |
| 13.4 | 8.63 |
| 14.6 | 100.00 |
| 15.5 | 1.74 |

-continued

| Angle (Degree 2θ) | Relative Intensity* % |
|---|---|
| 16.6 | 10.76 |
| 17.2 | 2.67 |
| 17.6 | 1.23 |
| 18.7 | 9.93 |
| 19.7 | 15.52 |
| 20.3 | 9.80 |
| 20.8 | 8.28 |
| 21.5 | 14.65 |
| 22.3 | 23.34 |
| 23.2 | 1.00 |
| 24.3 | 2.70 |
| 25.3 | 3.03 |
| 25.8 | 6.44 |
| 26.9 | 2.00 |
| 28.9 | 1.86 |
| 29.4 | 4.14 |
| 31.0 | 5.52 |
| 32.2 | 1.68 |
| 33.3 | 1.13 |
| 34.7 | 0.55 |

*The relative intensities may change depending on the crystal size and morphology.

In one embodiment, galactarate Type A is characterized by the SSNMR of FIG. 58. In one embodiment, galactarate Type A is characterized by the following $^{13}$C Solid State NMR shifts.

| v(F1) [ppm] | Intensity [abs] |
|---|---|
| 181.93 | 325948678 |
| 180.74 | 106103884 |
| 158.61 | 389548850 |
| 155.04 | 304336570 |
| 148.95 | 299428434 |
| 141.06 | 270978782 |
| 134.51 | 257792170 |
| 129.58 | 168049070 |
| 126.59 | 678416264 |
| 124.98 | 130287716 |
| 123.44 | 113070648 |
| 122.89 | 113280284 |
| 121.90 | 125311240 |
| 118.81 | 139884322 |
| 117.31 | 350712534 |
| 114.69 | 293874864 |
| 111.57 | 279212724 |
| 74.71 | 499615044 |
| 74.21 | 490241950 |
| 72.26 | 243497372 |
| 71.11 | 16264506 |
| 64.84 | 412653130 |
| 63.49 | 16083816 |
| 59.36 | 29923758 |
| 59.07 | 29863004 |
| 55.52 | 21032144 |
| 49.12 | 363759534 |
| 46.02 | 323447042 |
| 40.75 | 320978348 |
| 34.72 | 23351194 |
| 32.67 | 16782962 |
| 31.19 | 449367100 |
| 29.06 | 418670188 |
| 26.89 | 67807004 |
| 25.17 | 16194924 |
| 24.17 | 18556462 |
| 22.76 | 524726276 |
| 19.40 | 445112248 |
| 17.77 | 40117878 |
| 15.07 | 17708420 |
| 13.10 | 315386028 |
| 9.93 | 623470392 |
| 6.73 | 21738298 |

Representative $^{13}$C NMR chemical shifts for galactarate Type A are 126.59, 74.71, 31.19, and 22.76 ppm. Representative $^{13}$C NMR chemical shifts for galactarate Type A are also 126.59 and 74.71 ppm.

Phosphate

Figure 20:
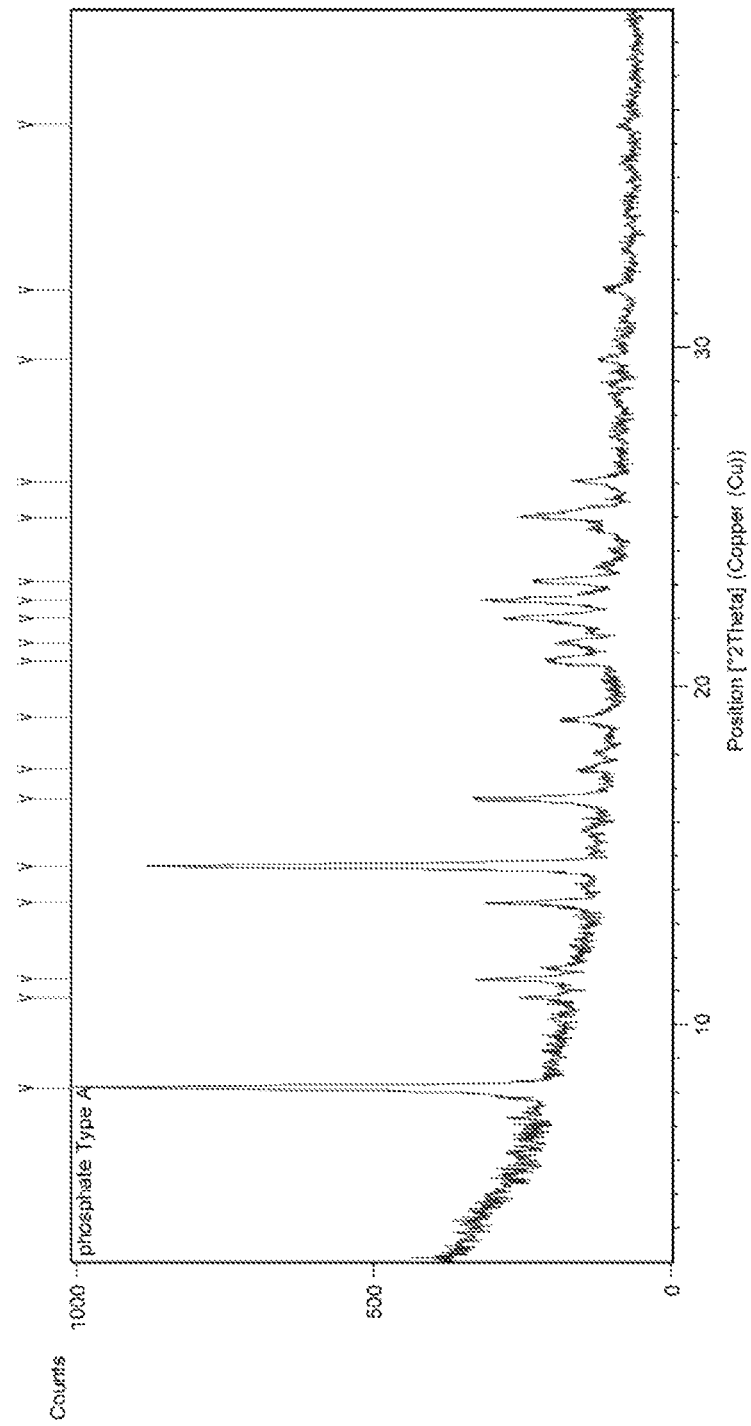
FIG. 20 is a XRPD Pattern of phosphate Type A.
Figure 21:
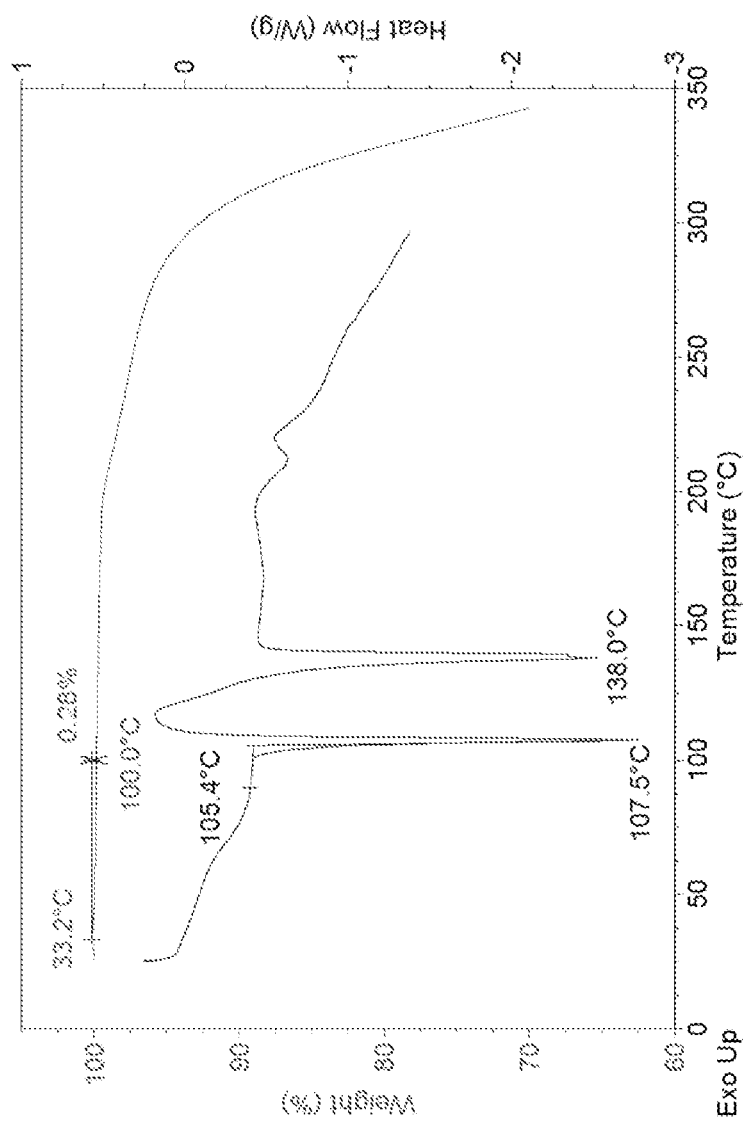
FIG. 21 is a DSC profile and a TGA of phosphate Type A.

In one aspect of the invention, the pharmaceutically acceptable salt of COMPOUND I is a phosphate. In one embodiment, the pharmaceutically acceptable salt of COMPOUND I is a mono-phosphate. In one embodiment, the phosphate is crystalline. In one embodiment, the phosphate is crystalline and is characterized by an XRPD pattern having peaks at 2θ angles of 8.1°, 14.7°, and 16.7±0.2°. In one embodiment, the phosphate is crystalline and is characterized by an XRPD pattern having peaks at 2θ angles of 8.1°, 13.6°, 14.7°, 16.7°, and 22.5±0.2°. In one embodiment, the phosphate is crystalline and is characterized by an XRPD pattern as shown in FIG. 20. In one embodiment, the phosphate is crystalline and is characterized by an endothermic peak at about 108° C. and an endothermic peak at about 138° C. as determined by DSC. In one embodiment, the phosphate is crystalline and is characterized by a DSC profile as shown in FIG. 21. In one embodiment, the phosphate is crystalline and is characterized by an about 0.3 wt % loss between room temperature and about 100° C. as determined by TGA. In one embodiment, the phosphate is crystalline and is characterized by a TGA profile as shown in FIG. 21. In one embodiment, the phosphate is crystalline and is characterized by at least two of the following features (I-i)-(I-ii):

(I-i) an XRPD pattern having peaks at 2θ angles of 8.1°, 14.7°, and 16.7±0.2°;

(I-i) a DSC profile as shown in FIG. 21; or (I-iii) a TGA profile as shown in FIG. 21.

In one embodiment, the phosphate is crystalline and is phosphate Type A.

Phosphate Type A is characterized by the following XRPD pattern expressed in terms of the degree 2θ and relative intensities:

| Angle (Degree 2θ) | Relative Intensity* % |
|---|---|
| 8.1 | 100.00 |
| 10.8 | 9.15 |
| 11.3 | 19.37 |
| 13.6 | 20.91 |
| 14.7 | 95.71 |
| 16.7 | 27.92 |
| 17.6 | 4.90 |
| 19.1 | 8.68 |
| 20.7 | 14.22 |
| 21.3 | 12.42 |
| 22.0 | 22.53 |
| 22.5 | 29.04 |
| 23.1 | 18.72 |
| 25.0 | 18.37 |
| 26.0 | 8.88 |
| 29.6 | 4.98 |
| 31.7 | 4.28 |
| 36.6 | 2.33 |

*The relative intensities may change depending on the crystal size and morphology.

Figure 60:
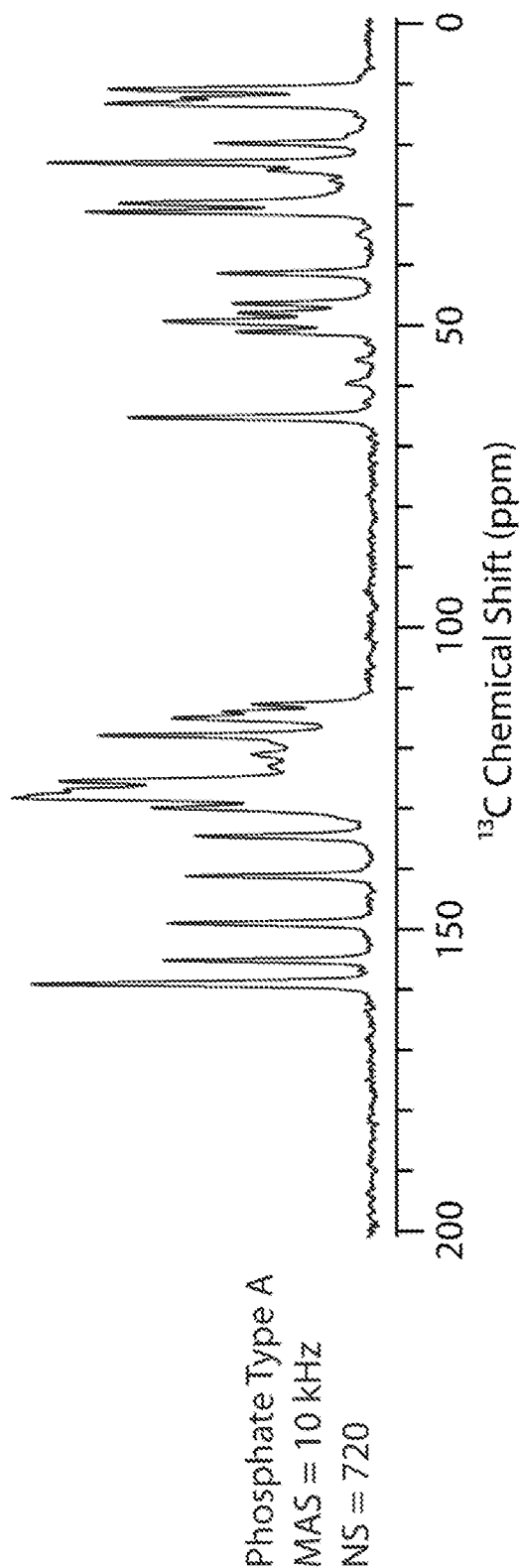
FIG. 60 is a $^{13}$C SSNMR spectrum of phosphate Type A.

In one embodiment, phosphate Type A is characterized by the SSNMR of FIG. 60. In one embodiment, phosphate Type A is characterized by the following $^{13}$C Solid State NMR shifts.

| v(F1) [ppm] | Intensity [abs] |
|---|---|
| 159.04 | 668857224 |
| 156.76 | 25017018 |
| 155.11 | 408439258 |
| 150.44 | 15088782 |
| 148.96 | 399671922 |
| 141.13 | 364566002 |
| 134.52 | 346968388 |
| 132.81 | 24859702 |
| 129.82 | 433432980 |
| 128.21 | 707551096 |
| 127.74 | 676987642 |
| 126.81 | 603713522 |
| 125.47 | 615857914 |
| 122.87 | 202753346 |
| 121.00 | 234871980 |
| 117.83 | 538405496 |
| 114.96 | 391806986 |
| 113.91 | 291927828 |
| 112.69 | 235856042 |
| 93.85 | 13223372 |
| 66.48 | 18030850 |
| 65.17 | 478771552 |
| 62.69 | 14226318 |
| 59.51 | 49241134 |
| 55.66 | 30043784 |
| 52.85 | 12991680 |
| 50.97 | 267380082 |
| 49.20 | 410782762 |
| 47.84 | 262230748 |
| 46.26 | 275719500 |
| 41.28 | 302341508 |
| 37.19 | 12948154 |
| 34.96 | 29409642 |
| 32.88 | 16260426 |
| 31.10 | 561930508 |
| 29.69 | 496689348 |
| 27.09 | 66726326 |
| 25.89 | 81441996 |
| 24.24 | 205034626 |
| 22.95 | 637653572 |
| 19.73 | 308598938 |
| 16.89 | 21254000 |
| 15.20 | 33640026 |
| 13.17 | 523917204 |
| 12.18 | 373527344 |
| 10.80 | 517532896 |
| 8.59 | 24727714 |
| 7.57 | 13904968 |

Representative $^{13}$C NMR chemical shifts for phosphate Type A are 159.04, 128.21, 31.10, and 22.95 ppm. Representative $^{13}$C NMR chemical shifts for phosphate Type A are 159.04 and 128.21 ppm.

L-Tartrate

Figure 22:
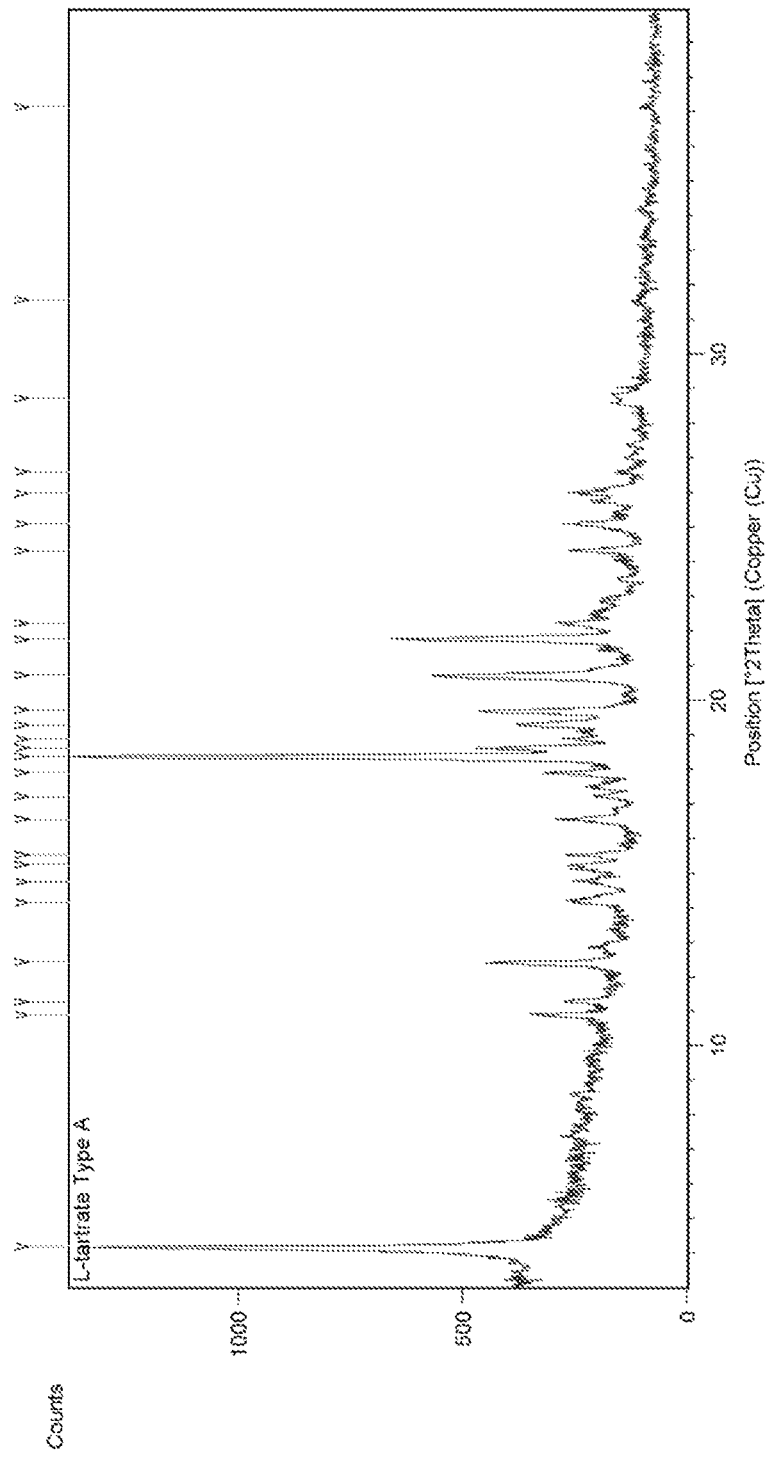
FIG. 22 is a XRPD Pattern of L-tartrate Type A.
Figure 23:
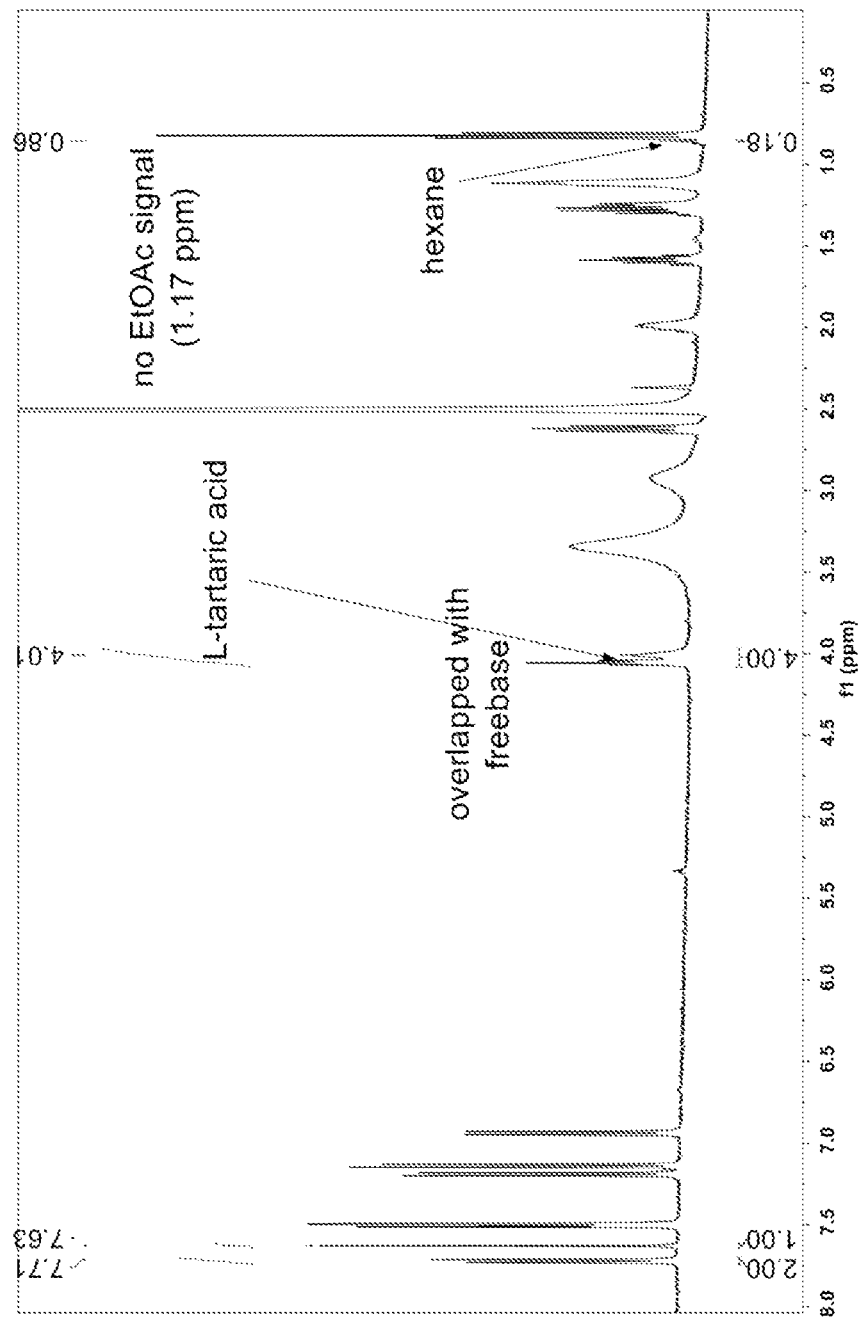
FIG. 23 is a $^1$H NMR spectrum of L-tartrate Type A.
Figure 24:
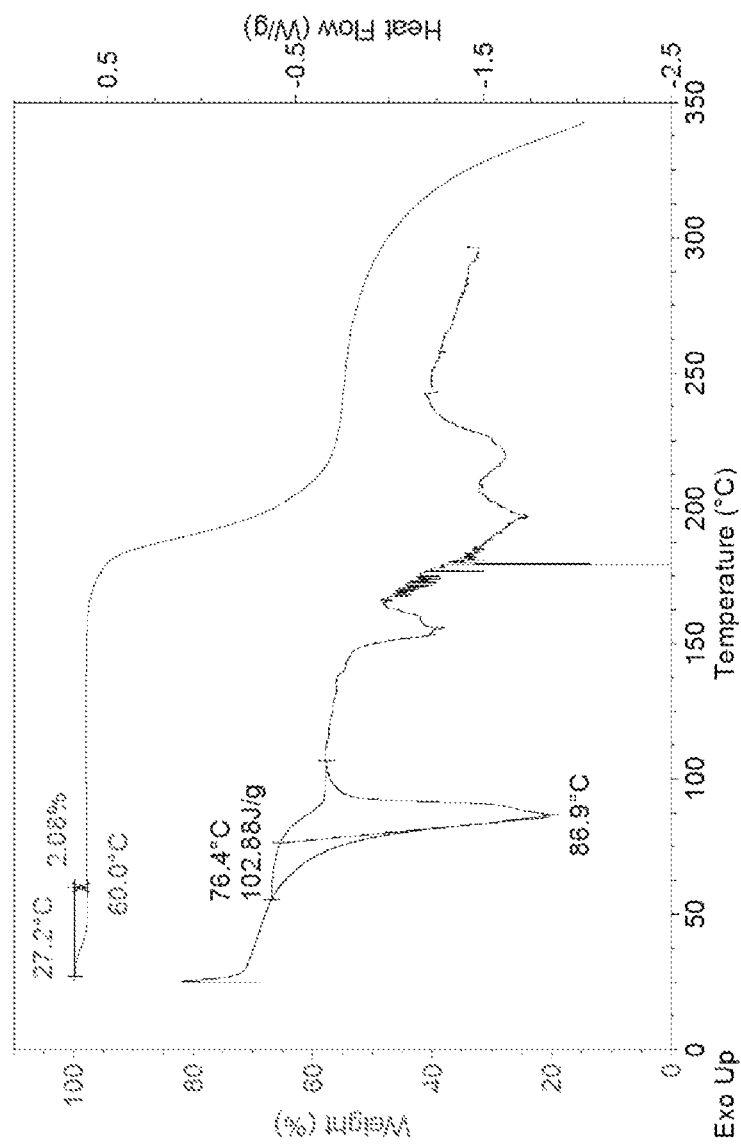
FIG. 24 is a DSC profile and a TGA of L-tartrate Type A.

In one aspect of the invention, the pharmaceutically acceptable salt of COMPOUND I is a L-tartrate. In one embodiment, the L-tartrate is crystalline. In one embodiment, the L-tartrate is crystalline and is characterized by an XRPD pattern having peaks at 2θ angles of 4.2°, 18.4°, and 21.8±0.2°. In one embodiment, the L-tartrate is crystalline and is characterized by an XRPD pattern having peaks at 2θ angles of 4.2°, 12.4°, 18.4°, 20.7°, and 21.8±0.2°. In one embodiment, the L-tartrate is crystalline and is characterized by an XRPD pattern as shown in FIG. 22. In one embodiment, the L-tartrate is crystalline and is characterized by a $^1$H-NMR substantially similar to FIG. 23. In one embodiment, the L-tartrate is crystalline and is characterized by an endothermic peak at about 87° C. as determined by DSC. In one embodiment, the L-tartrate is crystalline and is characterized by a DSC profile as shown in FIG. 24. In one embodiment, the L-tartrate is crystalline and is characterized by an about 2.1 wt % loss between room temperature and about 60° C. as determined by TGA. In one embodiment, the L-tartrate is crystalline and is characterized by a TGA profile as shown in FIG. 24. In one embodiment, the L-tartrate is crystalline and is characterized by at least two of the following features (I-i)-(I-iv):

(I-i) an XRPD pattern having peaks at 2θ angles of 4.2°, 18.4°, and 21.8±0.2°;
(I-li) a $^1$H-NMR as shown in FIG. 23;
(I-i) a DSC profile as shown in FIG. 24; or
(I-iii) a TGA profile as shown in FIG. 24.

In one embodiment, the L-tartrate is crystalline and is L-tartrate Type A.

L-tartrate Type A is characterized by the following XRPD pattern expressed in terms of the degree 2θ and relative intensities:

| Angle (Degree 2θ) | Relative Intensity* % |
|---|---|
| 4.2 | 86.67 |
| 10.9 | 12.97 |
| 11.3 | 8.23 |
| 12.4 | 22.81 |
| 14.1 | 8.48 |
| 14.7 | 6.64 |
| 15.2 | 9.45 |
| 15.5 | 10.21 |
| 16.6 | 11.70 |
| 17.2 | 6.01 |
| 17.9 | 15.37 |
| 18.4 | 100.00 |
| 18.6 | 28.32 |
| 18.9 | 11.34 |
| 19.3 | 21.41 |
| 19.7 | 26.27 |
| 20.7 | 36.58 |
| 21.8 | 43.58 |
| 22.2 | 14.48 |
| 24.3 | 13.04 |
| 25.1 | 12.82 |
| 26.0 | 10.77 |
| 26.6 | 3.78 |
| 28.7 | 5.29 |
| 31.6 | 1.67 |
| 37.1 | 1.39 |

*The relative intensities may change depending on the crystal size and morphology.

Figure 25:
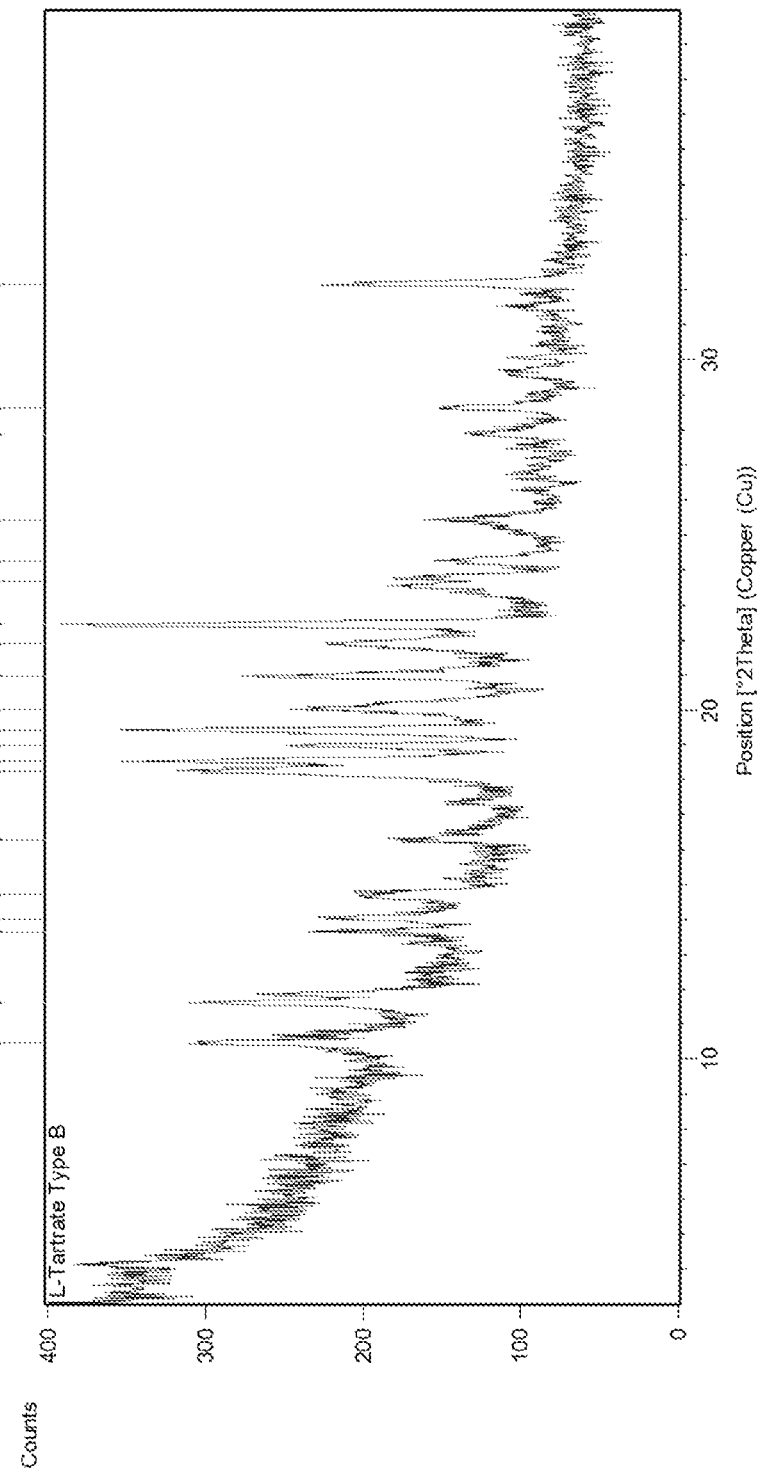
FIG. 25 is a XRPD Pattern of L-tartrate Type B.
Figure 26:
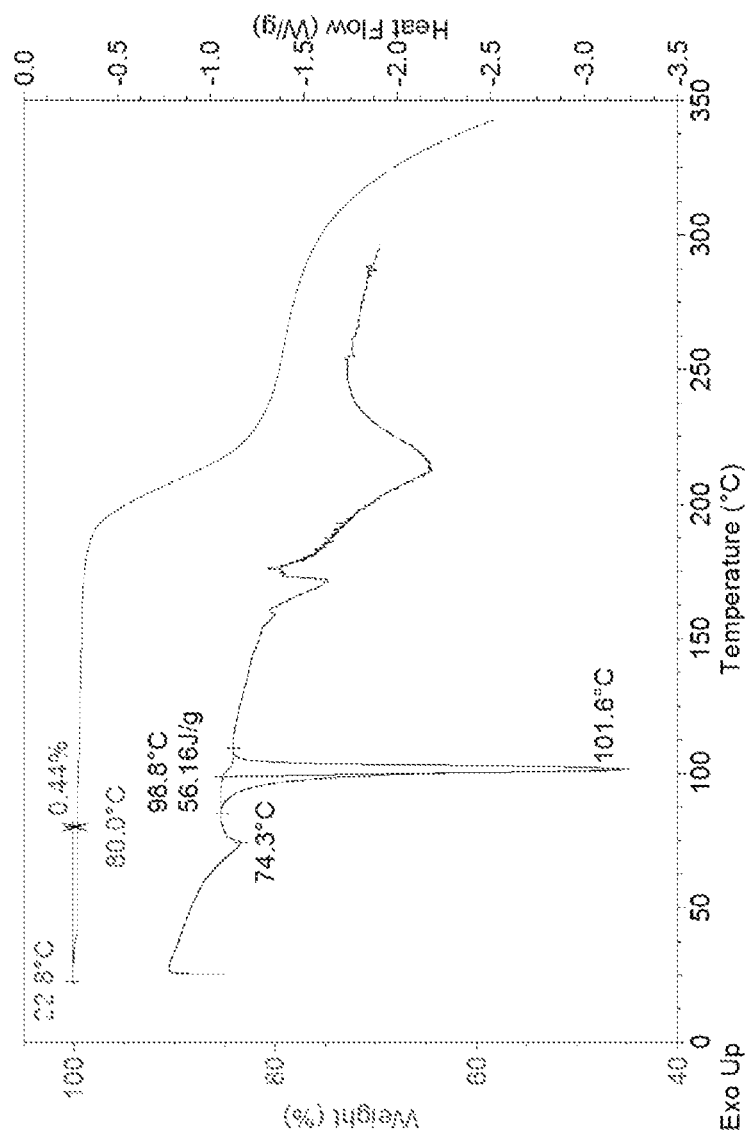
FIG. 26 is a DSC profile and a TGA of L-tartrate Type B.

In one embodiment, the L-tartrate is crystalline and is characterized by an XRPD pattern having peaks at 2θ angles of 18.5, 22.5°, and 32.1°±0.2°. In one embodiment, the L-tartrate is crystalline and is characterized by an XRPD pattern having peaks at 2θ angles of 4.2°, 12.4°, 18.4°, 20.7°, and 21.8±0.2°. In one embodiment, the L-tartrate is crystalline and is characterized by an XRPD pattern as shown in FIG. 25. In one embodiment, the L-tartrate is crystalline and is characterized by an endothermic peak at about 102° C. as determined by DSC. In one embodiment, the L-tartrate is crystalline and is characterized by a DSC profile as shown in FIG. 26. In one embodiment, the L-tartrate is crystalline and is characterized by a TGA profile as shown in FIG. 26. In one embodiment, the L-tartrate is crystalline and is characterized by at least two of the following features (I-i)-(I-ii):

(I-i) an XRPD pattern having peaks at 2θ angles of 18.5, 22.5°, and 32.1°±0.2°;
(I-i) a DSC profile as shown in FIG. 26; or
(I-iii) a TGA profile as shown in FIG. 26.

In one embodiment, the L-tartrate is crystalline and is L-tartrate Type B.

L-tartrate Type B is characterized by the following XRPD pattern expressed in terms of the degree 2θ and relative intensities:

| Angle (Degree 2θ) | Relative Intensity* % |
|---|---|
| 10.5 | 47.35 |
| 11.6 | 54.39 |
| 13.7 | 29.50 |
| 14.0 | 34.31 |
| 14.7 | 24.35 |
| 16.3 | 21.65 |
| 18.2 | 76.29 |
| 18.5 | 85.06 |
| 19.0 | 50.98 |
| 19.4 | 93.08 |
| 20.0 | 51.19 |
| 21.0 | 66.20 |
| 21.9 | 47.66 |
| 22.5 | 100.00 |
| 23.7 | 25.95 |
| 24.3 | 22.66 |
| 25.4 | 24.29 |
| 27.9 | 19.53 |
| 28.6 | 27.54 |
| 32.1 | 58.41 |

*The relative intensities may change depending on the crystal size and morphology.

Figure 61:
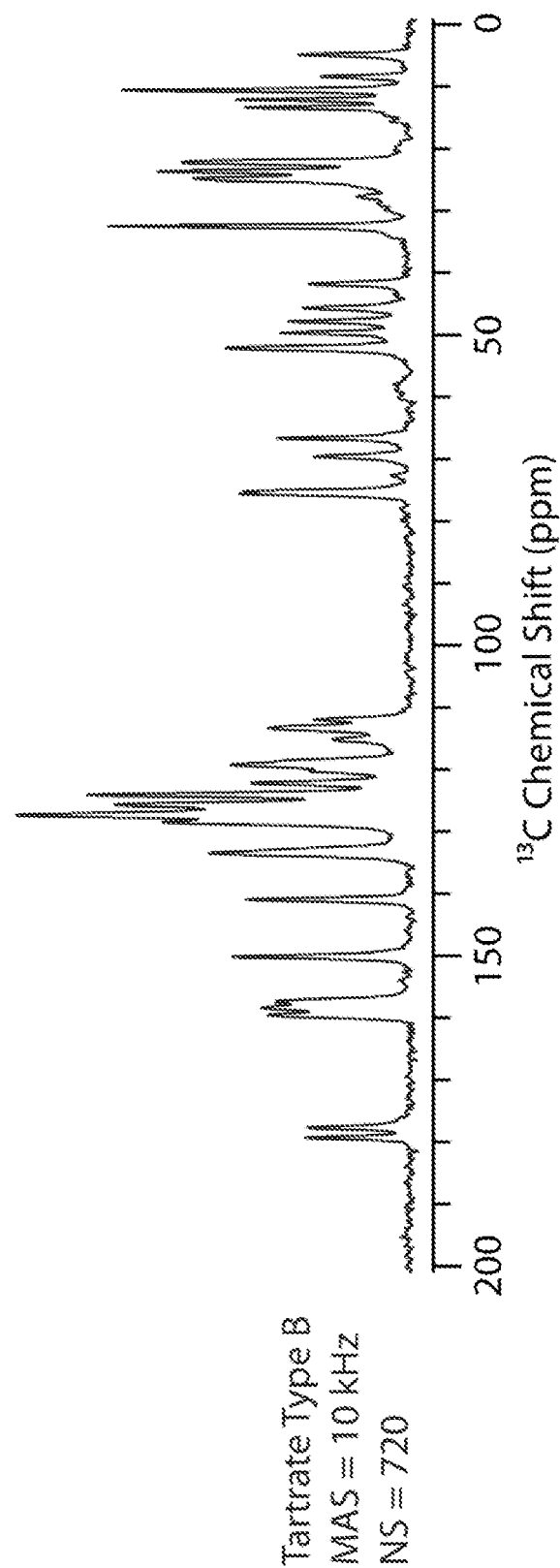
FIG. 61 is a $^{13}$C SSNMR spectrum of L-tartrate Type B.

In one embodiment, L-tartrate Type B is characterized by the SSNMR of FIG. 61. In one embodiment, L-tartrate Type B is characterized by the following $^{13}C$ Solid State NMR shifts.

| v(F1) [ppm] | Intensity [abs] |
|---|---|
| 179.26 | 197227948 |
| 177.65 | 194065766 |
| 159.46 | 270033300 |
| 158.34 | 281060904 |
| 157.30 | 255350146 |
| 150.10 | 337870880 |
| 140.87 | 310375606 |
| 133.43 | 381450066 |
| 128.44 | 471381052 |
| 127.29 | 751441526 |
| 125.62 | 564923424 |
| 124.04 | 615212706 |
| 122.13 | 303216384 |
| 120.17 | 191819962 |
| 119.22 | 340836160 |
| 115.09 | 145883852 |
| 113.28 | 268375212 |
| 111.88 | 180733110 |
| 75.55 | 325209208 |
| 75.11 | 316496846 |
| 72.56 | 34876260 |
| 69.52 | 180361452 |
| 66.59 | 251002408 |
| 60.12 | 19450206 |
| 58.88 | 26503388 |
| 58.33 | 23807320 |
| 57.90 | 30024954 |
| 52.06 | 350646012 |
| 49.59 | 245448022 |
| 47.76 | 229050772 |
| 45.59 | 202811096 |
| 43.78 | 24885608 |
| 43.36 | 28184022 |
| 41.74 | 191949572 |
| 32.43 | 576054786 |
| 29.77 | 45487472 |
| 28.81 | 60315040 |
| 27.61 | 99146488 |
| 24.74 | 411930378 |
| 23.59 | 480259778 |
| 22.21 | 434905310 |
| 20.17 | 26904036 |
| 15.59 | 35099692 |
| 14.38 | 49778084 |
| 13.33 | 313809090 |
| 12.04 | 329599528 |
| 10.53 | 547971234 |
| 8.32 | 167499990 |
| 4.81 | 210207514 |

Representative $^{13}C$ NMR chemical shifts for L-tartrate Type B are 127.29, 32.43, and 23.59 ppm. Representative $^{13}C$ NMR chemical shifts for L-tartrate Type B are also 179.26 and 127.29 ppm.

Hippurate

Figure 27:
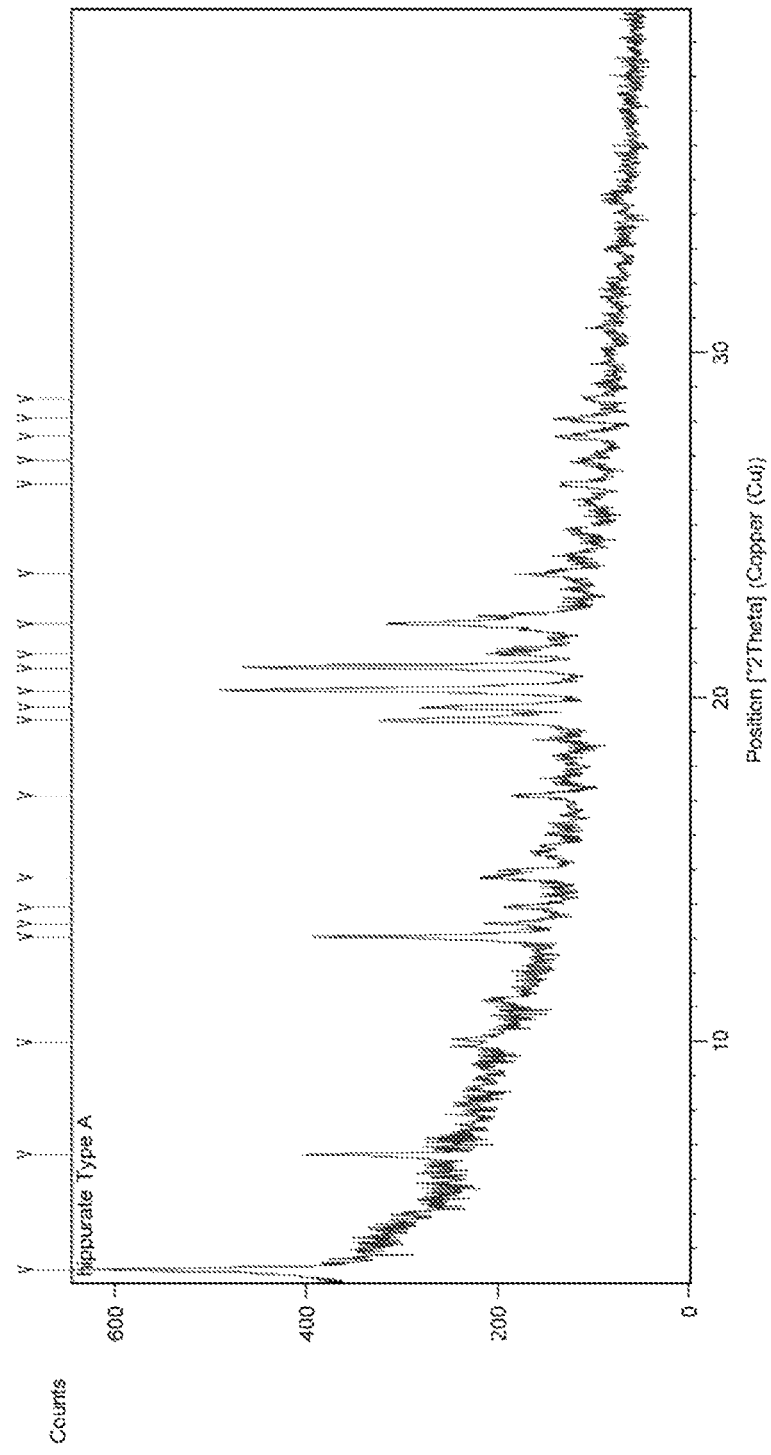
FIG. 27 is a XRPD Pattern of hippurate Type A.
Figure 28:
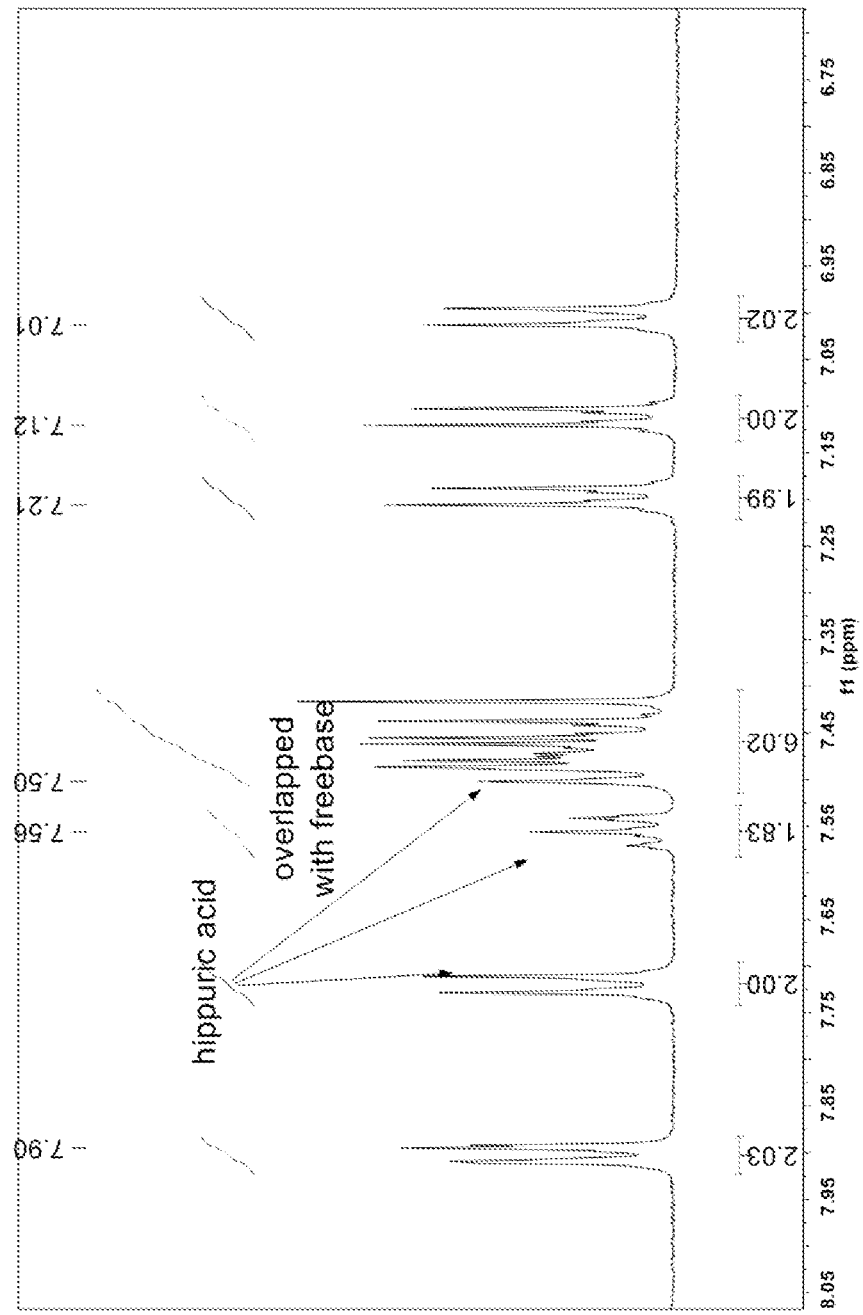
FIG. 28 is a $^1$H NMR spectrum of hippurate Type A.
Figure 29:
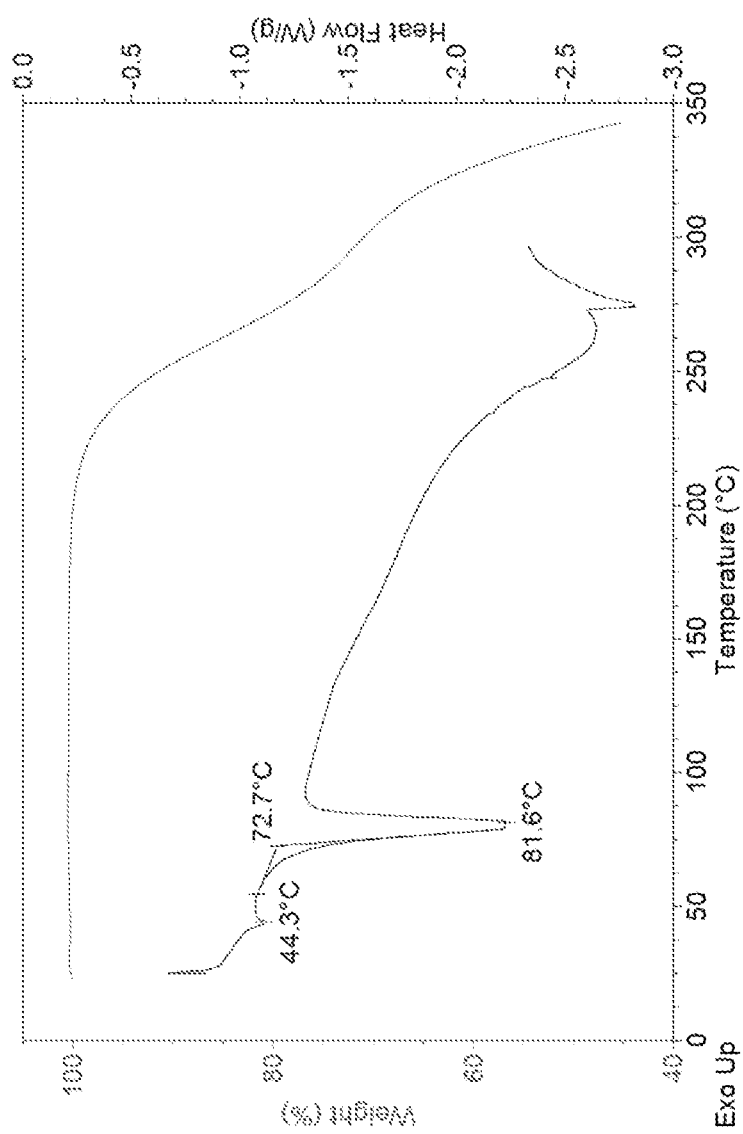
FIG. 29 is a DSC profile and a TGA of hippurate Type A.

In one aspect of the invention, the pharmaceutically acceptable salt of COMPOUND I is a hippurate. In one embodiment, the pharmaceutically acceptable salt of COMPOUND I is a mono-hippurate. In one embodiment, the hippurate is crystalline. In one embodiment, the hippurate is crystalline and is characterized by an XRPD pattern having peaks at 2θ angles of 3.4°, 20.2°, and 20.9°±0.2°. In one embodiment, the hippurate is crystalline and is characterized by an XRPD pattern having peaks at 2θ angles of 3.4°, 13.0°, 20.2°, 20.9°, and 22.1°±0.2°. In one embodiment, the hippurate is crystalline and is characterized by an XRPD pattern as shown in FIG. 27. In one embodiment, the hippurate is crystalline and is characterized by a $^{1}H$-NMR substantially similar to FIG. 28. In one embodiment, the hippurate is crystalline and is characterized by an endothermic peak at about 44.3° C. and an endothermic peak at about 81.6° C. as determined by DSC. In one embodiment, the hippurate is crystalline and is characterized by a DSC profile as shown in FIG. 29. In one embodiment, the hippurate is crystalline and is characterized by a TGA profile as shown in FIG. 29. In one embodiment, the hippurate is crystalline and is characterized by at least two of the following features (I-i)-(I-iv):

(I-i) an XRPD pattern having peaks at 2θ angles of 3.4°, 20.2°, and 20.9°±0.2°;

(I-i) a $^{1}H$-NMR substantially similar to FIG. 28;

(I-iii) a DSC profile as shown in FIG. 29; or (I-iv) a TGA profile as shown in FIG. 29.

In one embodiment, the hippurate is crystalline and is hippurate Type A.

Hippurate Type A is characterized by the following XRPD pattern expressed in terms of the degree 2θ and relative intensities:

| Angle (Degree 2θ) | Relative Intensity* % |
|---|---|
| 3.4 | 99.59 |
| 6.7 | 42.48 |
| 10.0 | 9.34 |
| 13.0 | 62.99 |
| 13.4 | 13.38 |
| 13.9 | 11.68 |
| 14.8 | 19.87 |
| 17.1 | 15.91 |
| 19.3 | 57.21 |
| 19.7 | 45.04 |
| 20.2 | 100.00 |
| 20.9 | 97.12 |
| 21.3 | 25.78 |
| 22.1 | 57.72 |
| 23.6 | 17.21 |
| 26.2 | 13.01 |
| 26.9 | 5.63 |
| 27.6 | 13.91 |
| 28.1 | 15.59 |
| 28.7 | 7.60 |

*The relative intensities may change depending on the crystal size and morphology.

Figure 62:
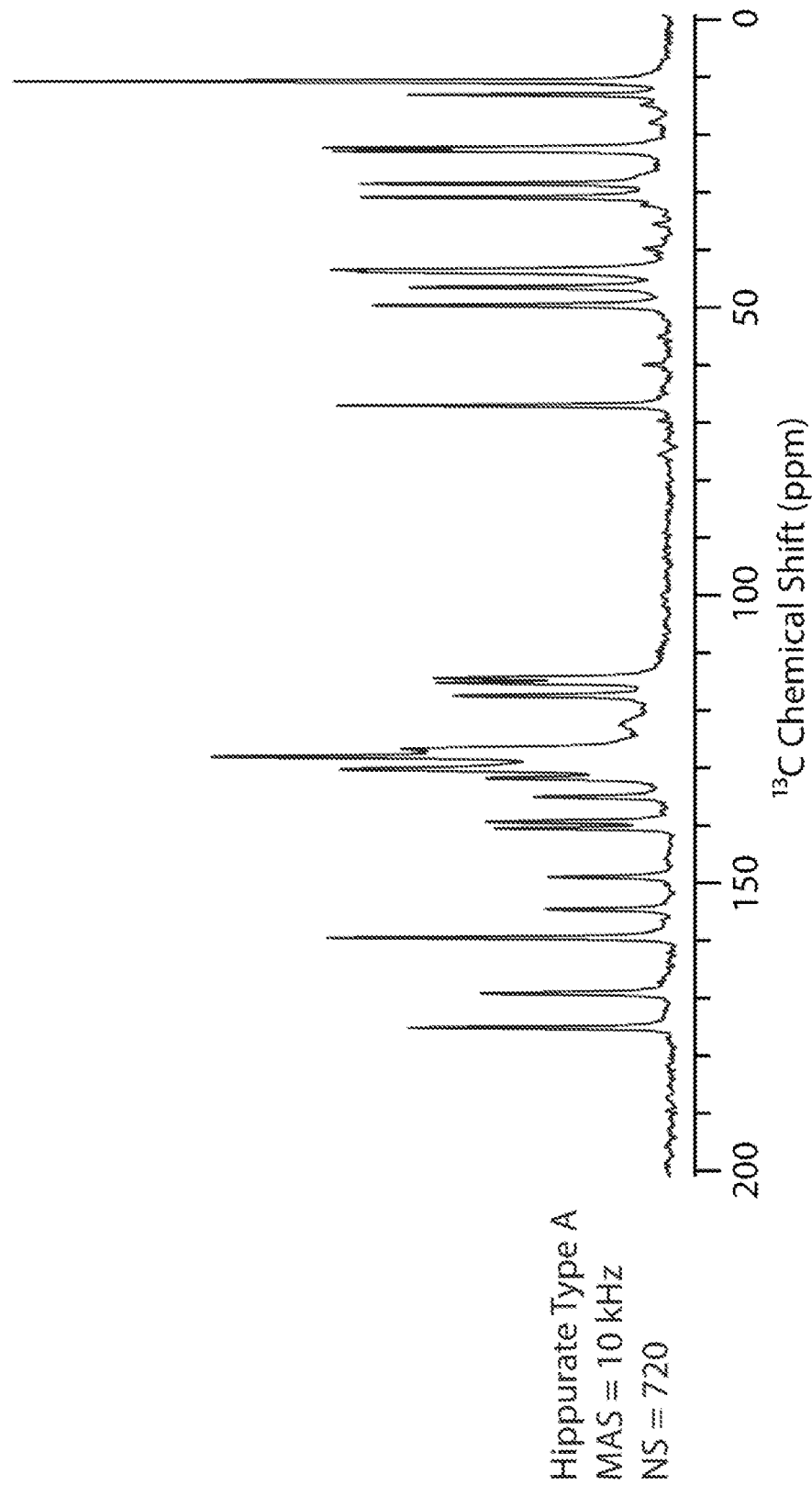
FIG. 62 is a $^{13}$C SSNMR spectrum of hippurate Type A.

In one embodiment, hippurate Type A is characterized by the SSNMR of FIG. 62. In one embodiment, hippurate Type A is characterized by the following $^{13}$C Solid State NMR shifts.

| v(F1) [ppm] | Intensity [abs] |
|---|---|
| 175.07 | 536996244 |
| 169.11 | 388809548 |
| 159.46 | 707295764 |
| 154.52 | 254091908 |
| 148.90 | 247577616 |
| 140.44 | 359376636 |
| 139.33 | 377787640 |
| 134.98 | 277284504 |
| 131.76 | 378359044 |
| 130.20 | 680169748 |
| 128.01 | 947549856 |
| 127.17 | 516324924 |
| 126.64 | 552370164 |
| 124.11 | 77433492 |
| 122.43 | 101402928 |
| 122.00 | 96818692 |
| 119.60 | 56224288 |
| 117.41 | 444677132 |
| 115.14 | 479938164 |
| 114.36 | 485993716 |
| 112.14 | 27360080 |
| 109.67 | 25242052 |
| 66.99 | 685739596 |
| 59.90 | 51412780 |
| 49.58 | 610780496 |
| 46.43 | 535428332 |
| 43.77 | 642153872 |
| 43.40 | 699072908 |
| 40.78 | 27447988 |
| 39.66 | 50607052 |
| 35.44 | 30868404 |
| 32.15 | 55418392 |
| 30.81 | 637101644 |
| 28.45 | 639591940 |
| 25.76 | 26982976 |
| 25.47 | 28316724 |
| 25.03 | 28916204 |
| 22.76 | 695916772 |
| 22.21 | 715084348 |
| 17.83 | 38960068 |
| 14.79 | 56541640 |
| 12.98 | 539719136 |
| 10.65 | 1356709656 |

Representative $^{13}$C NMR chemical shifts for hippurate Type A are 159.46, 128.01, 66.99, and 10.65 ppm. Representative $^{13}$C NMR chemical shifts for hippurate Type A are 159.46 and 128.01 ppm.

L-Malate

Figure 30:
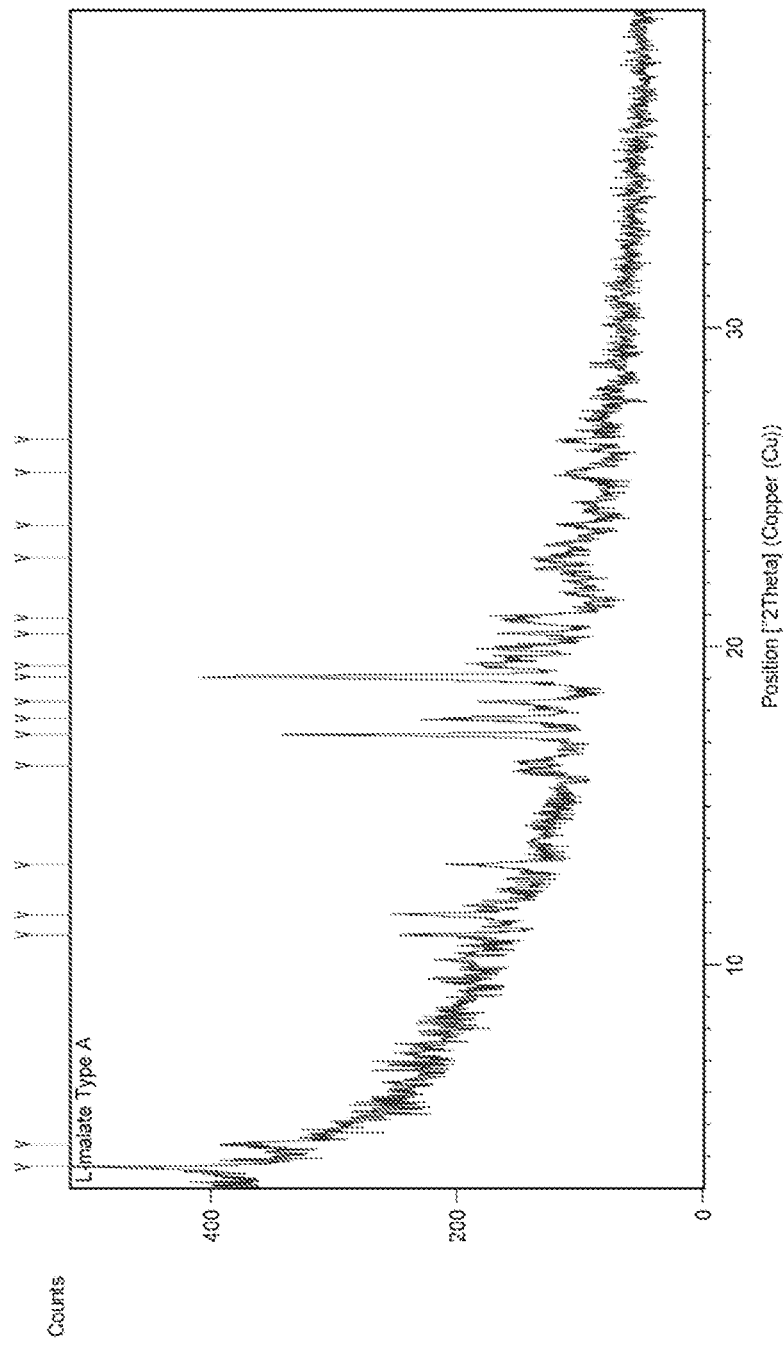
FIG. 30 is a XRPD Pattern of L-malate Type A.
Figure 31:
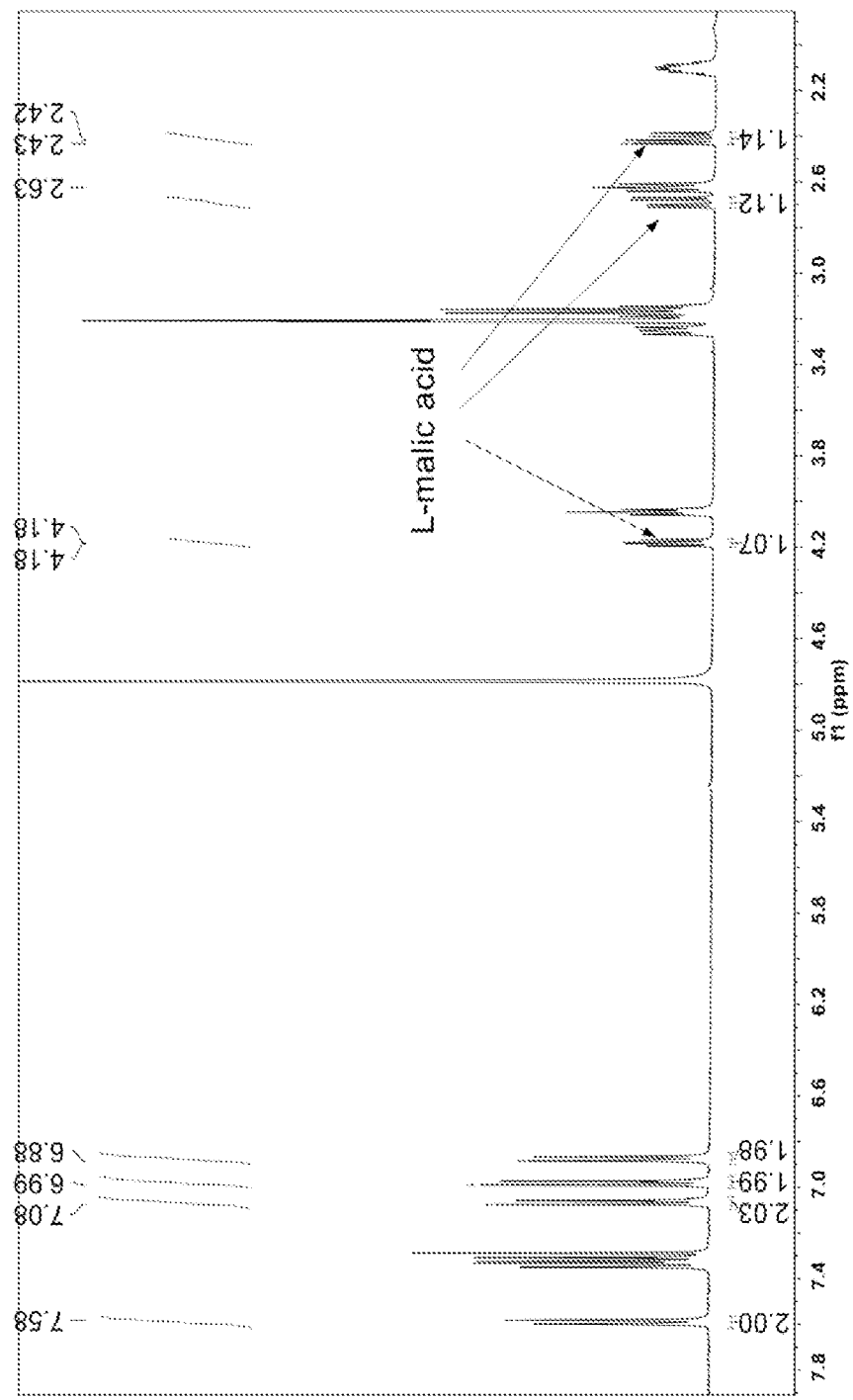
FIG. 31 is a $^1$H NMR spectrum of L-malate Type A.
Figure 32:
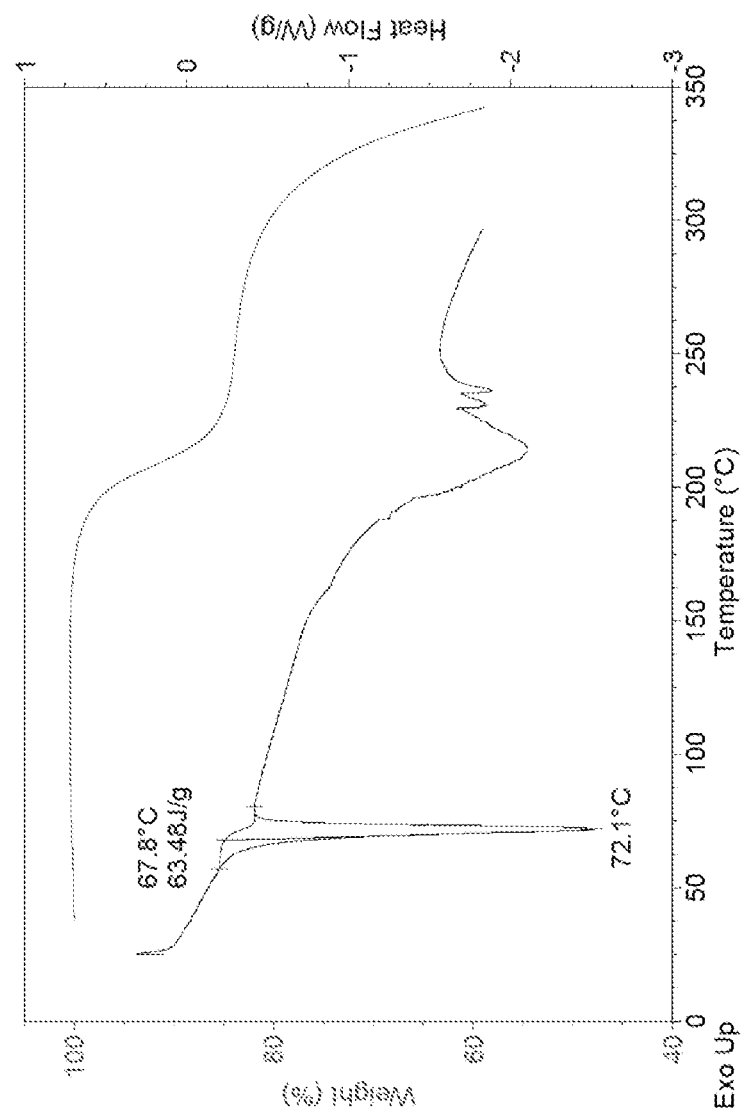
FIG. 32 is a DSC profile and a TGA of L-malate Type A.

In one aspect of the invention, the pharmaceutically acceptable salt of COMPOUND 1 is a L-malate. In one embodiment, the L-malate is crystalline. In one embodiment, the L-malate is crystalline and is characterized by an XRPD pattern having peaks at 2θ angles of 3.7°, 17.2°, and 19.0±0.2°. In one embodiment, the L-malate is crystalline and is characterized by an XRPD pattern having peaks at 2θ angles of 3.7°, 17.2°, 19.0°, and 19.4°±0.2°. In one embodiment, the L-malate is crystalline and is characterized by an XRPD pattern as shown in FIG. 30. In one embodiment, the L-malate is crystalline and is characterized by a $^{1}$H-NMR substantially similar to FIG. 31. In one embodiment, the L-malate is crystalline and is characterized by an endothermic peak at about 72° C. as determined by DSC. In one embodiment, the L-malate is crystalline and is characterized by a DSC profile as shown in FIG. 32. In one embodiment, the L-malate is crystalline and is characterized by a TGA profile as shown in FIG. 32. In one embodiment, the L-malate is crystalline and is characterized by at least two of the following features (I-i)-(I-iv):

(I-i) an XRPD pattern having peaks at 2θ angles of 3.7°, 17.2°, and 19.0±0.2°;
(I-i) a $^{1}$H-NMR substantially similar to FIG. 31;
(I-iii) a DSC profile as shown in FIG. 32; or
(I-iv) a TGA profile as shown in FIG. 32.

In one embodiment, the L-malate is crystalline and is L-malate Type A.

L-malate Type A is characterized by the following XRPD pattern expressed in terms of the degree 2θ and relative intensities:

| Angle (Degree 2θ) | Relative Intensity* % |
|---|---|
| 3.7 | 88.05 |
| 4.4 | 48.29 |
| 11.0 | 23.49 |
| 11.6 | 30.65 |
| 13.2 | 21.84 |
| 16.3 | 8.73 |
| 17.3 | 76.79 |
| 17.7 | 34.62 |
| 18.3 | 25.97 |
| 19.0 | 100.00 |
| 19.4 | 28.37 |
| 20.4 | 23.16 |
| 20.9 | 19.85 |
| 22.8 | 11.08 |
| 23.8 | 9.45 |
| 25.5 | 11.47 |
| 26.5 | 11.86 |

*The relative intensities may change depending on the crystal size and morphology.

Figure 63:
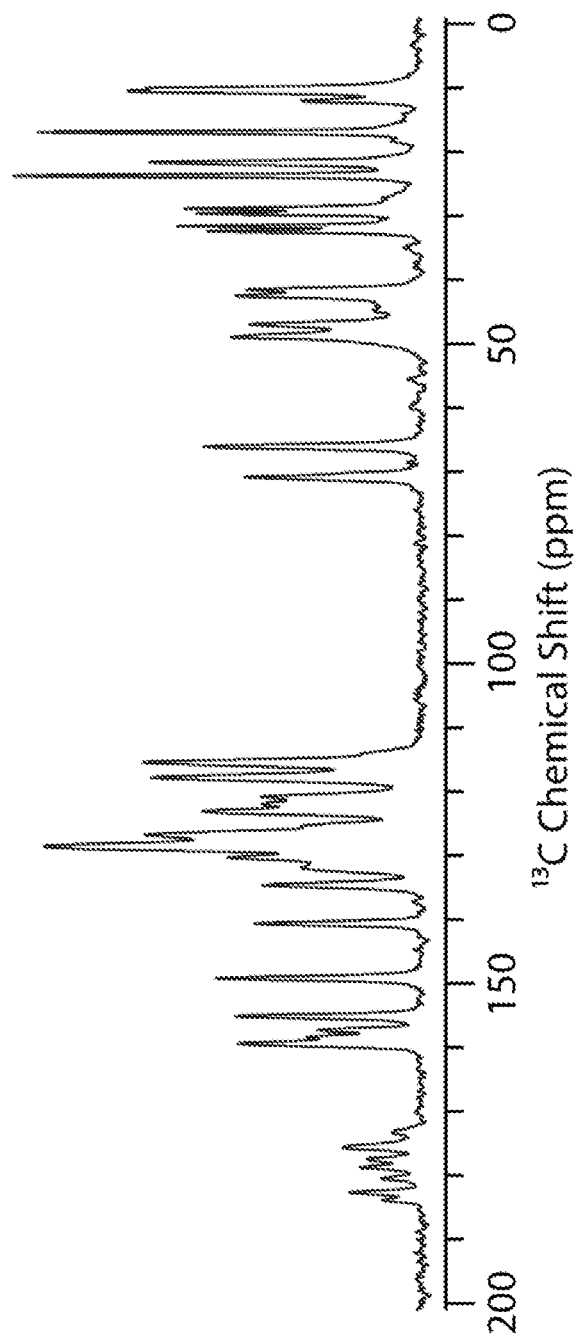
FIG. 63 is a $^{13}$C SSNMR spectrum of malate Type A.

In one embodiment, L-malate Type A is characterized by the SSNMR of FIG. 63. In one embodiment, L-malate Type A is characterized by the following $^{13}$C Solid State NMR shifts.

| v(F1) [ppm] | Intensity [abs] |
|---|---|
| 183.81 | 73149708 |
| 182.62 | 133479594 |
| 180.47 | 73854752 |
| 178.70 | 112511284 |
| 177.40 | 100085658 |
| 175.61 | 144403858 |
| 173.33 | 53467518 |
| 159.35 | 339314562 |
| 158.33 | 212072860 |
| 157.26 | 190555250 |
| 155.05 | 344483764 |
| 149.14 | 381526652 |
| 140.57 | 309622658 |
| 134.57 | 294325222 |
| 131.83 | 221055036 |
| 130.24 | 360733862 |
| 128.47 | 702166424 |
| 126.72 | 514055648 |
| 123.02 | 406924402 |
| 121.92 | 295154322 |
| 120.76 | 297586874 |
| 117.75 | 501635754 |
| 115.37 | 518536408 |
| 70.75 | 327004524 |
| 69.21 | 21959106 |
| 68.49 | 25691294 |
| 66.01 | 403435940 |
| 59.99 | 21421250 |
| 55.53 | 24299200 |
| 48.90 | 354613014 |
| 46.90 | 318911998 |
| 45.48 | 64446680 |

| v(F1) [ppm] | Intensity [abs] |
|---|---|
| 44.69 | 88696532 |
| 42.44 | 346713864 |
| 41.44 | 324356618 |
| 34.92 | 31494084 |
| 34.52 | 25039434 |
| 32.36 | 397284450 |
| 31.56 | 452242880 |
| 29.55 | 416876052 |
| 28.78 | 440724692 |
| 27.11 | 71170336 |
| 23.65 | 758949044 |
| 21.53 | 504861284 |
| 18.12 | 55775026 |
| 16.84 | 712075916 |
| 14.85 | 32995138 |
| 14.04 | 35477352 |
| 11.95 | 223370624 |
| 10.41 | 547027144 |
| 9.98 | 513262326 |
| 7.92 | 24373530 |
| 3.28 | 18663958 |

Representative $^{13}$C NMR chemical shifts for L-malate Type A are 128.47, 115.37, 66.01, and 16.84 ppm. Representative $^{13}$C NMR chemical shifts for L-malate Type A are 128.47 and 115.37 ppm.

Oxalate

Figure 33:
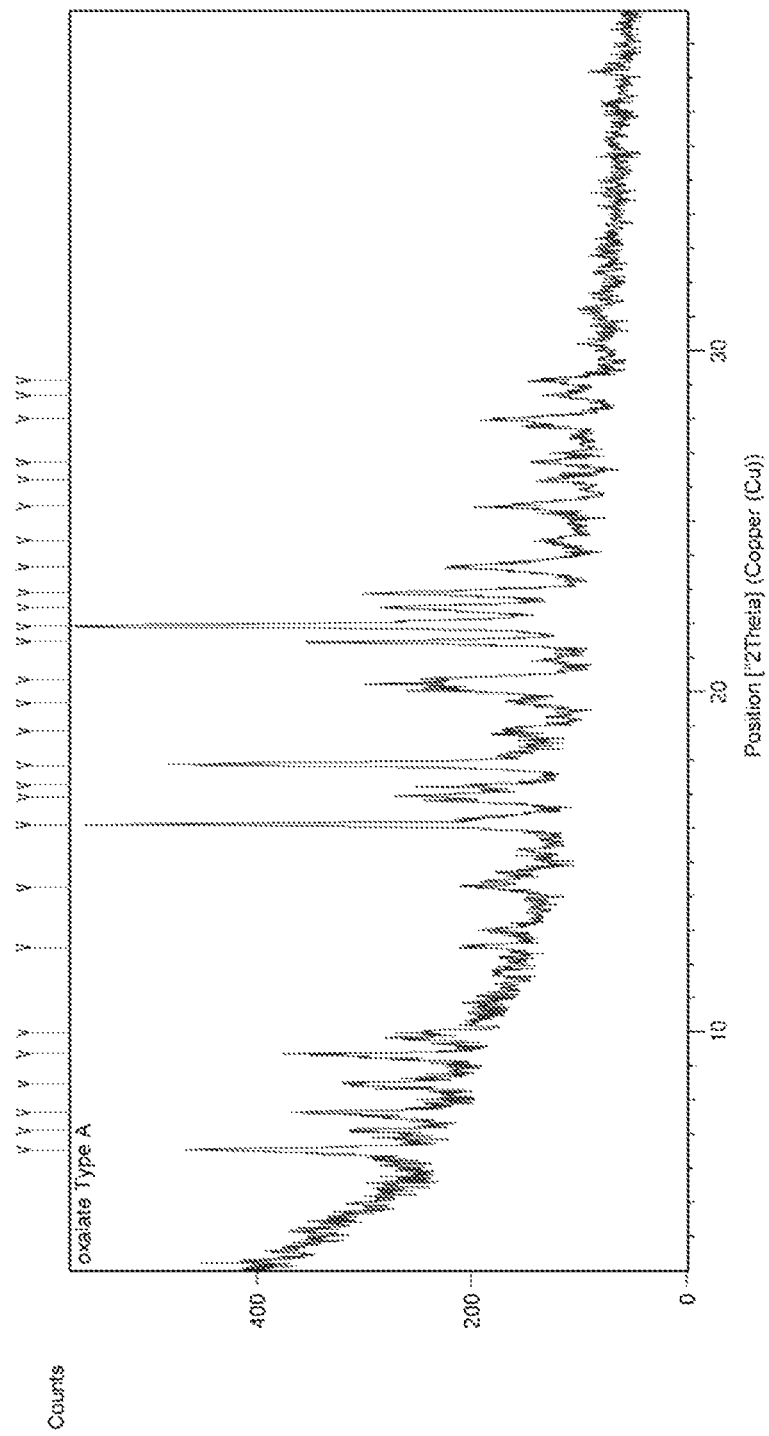
FIG. 33 is a XRPD Pattern of oxalate Type A.
Figure 34:
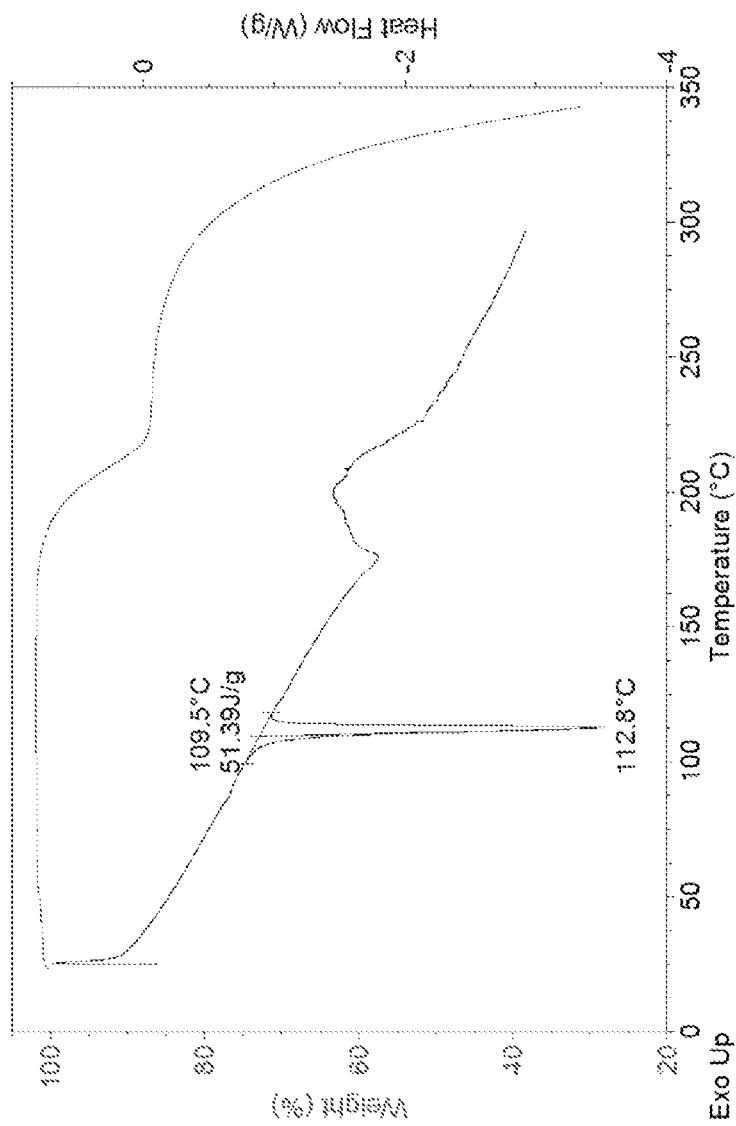
FIG. 34 is a DSC profile and a TGA of oxalate Type A.

In one aspect of the invention, the pharmaceutically acceptable salt of COMPOUND I is an oxalate. In one embodiment, the pharmaceutically acceptable salt of COMPOUND I is a mono-oxalate. In one embodiment, the oxalate is crystalline. In one embodiment, the oxalate is crystalline and is characterized by an XRPD pattern having peaks at 2θ angles of 16.1°, 17.8°, and 21.9±0.2°. In one embodiment, the oxalate is crystalline and is characterized by an XRPD pattern having peaks at 2θ angles of 16.1°, 17.8°, 21.5°, 22.5°, and 21.9±0.2°. In one embodiment, the oxalate is crystalline and is characterized by an XRPD pattern as shown in FIG. 33. In one embodiment, the oxalate is crystalline and is characterized by an endothermic peak at about 113° C. as determined by DSC. In one embodiment, the oxalate is crystalline and is characterized by a DSC profile as shown in FIG. 34. In one embodiment, the oxalate is crystalline and is characterized by a TGA profile as shown in FIG. 34. In one embodiment, the oxalate is crystalline and is characterized by at least two of the following features (I-i)-(I-ii):

(I-i) an XRPD pattern having peaks at 2θ angles of 16.1°, 17.8°, and 21.9±0.2°;
(I-ii) a DSC profile as shown in FIG. 34; or
(I-iii) a TGA profile as shown in FIG. 34.

In one embodiment, the oxalate is crystalline and is oxalate Type A.

Oxalate Type A is characterized by the following XRPD pattern expressed in terms of the degree 2θ and relative intensities:

| Angle (Degree 2θ) | Relative Intensity* % |
|---|---|
| 6.5 | 46.94 |
| 7.1 | 14.57 |
| 7.7 | 28.85 |
| 8.5 | 21.49 |
| 9.4 | 31.28 |
| 10.0 | 12.14 |
| 12.5 | 11.06 |
| 14.2 | 11.89 |
| 16.1 | 94.12 |
| 16.9 | 23.59 |
| 17.2 | 19.17 |
| 17.8 | 73.32 |
| 18.8 | 9.68 |
| 19.7 | 8.32 |
| 20.3 | 25.87 |
| 21.5 | 54.15 |
| 21.9 | 100.00 |
| 22.5 | 38.71 |
| 22.9 | 39.72 |
| 23.6 | 25.66 |
| 24.4 | 8.18 |
| 25.4 | 15.80 |
| 26.2 | 9.19 |
| 26.7 | 11.51 |
| 28.0 | 21.78 |
| 28.7 | 10.06 |
| 29.1 | 12.40 |

*The relative intensities may change depending on the crystal size and morphology.

Figure 64:
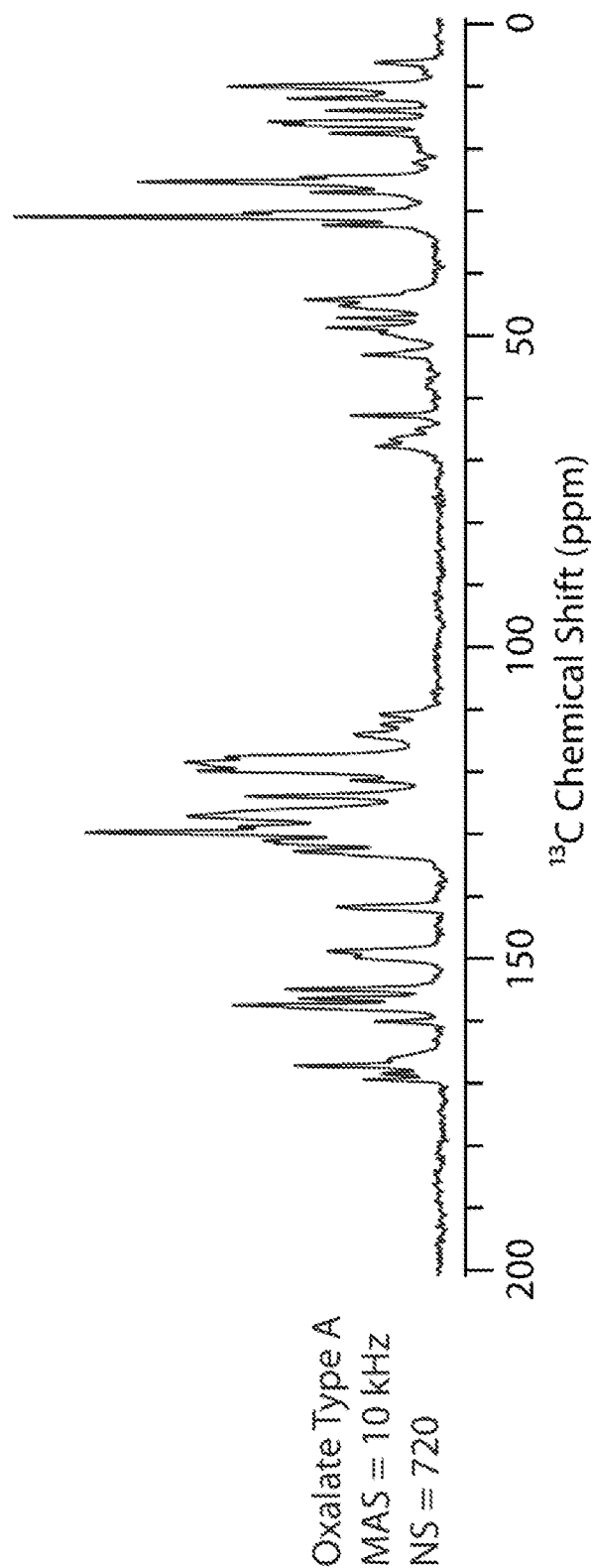
FIG. 64 is a $^{13}$C SSNMR spectrum of oxalate Type A.

In one embodiment, oxalate Type A is characterized by the SSNMR of FIG. 64. In one embodiment, oxalate Type A is characterized by the following $^{13}$C Solid State NMR shifts.

| v(F1) [ppm] | Intensity [abs] |
|---|---|
| 169.35 | 143373588 |
| 168.40 | 110288062 |
| 167.13 | 276143990 |
| 166.16 | 97188958 |
| 160.04 | 122397028 |
| 157.40 | 395846290 |
| 156.35 | 267856646 |
| 154.86 | 293830770 |
| 149.64 | 161277116 |
| 148.72 | 213841548 |
| 141.63 | 194621074 |
| 132.73 | 277567956 |
| 131.46 | 315460830 |
| 130.99 | 335493672 |
| 129.67 | 679603646 |
| 128.79 | 385227818 |
| 127.07 | 482576294 |
| 123.88 | 370029926 |
| 121.34 | 169021724 |
| 119.82 | 464071608 |
| 118.41 | 486692708 |
| 117.57 | 409208264 |
| 113.94 | 162239534 |
| 112.40 | 111088328 |
| 110.80 | 113749464 |
| 67.72 | 122355486 |
| 66.63 | 93880362 |
| 65.06 | 44696072 |
| 62.76 | 169457102 |
| 53.06 | 146542208 |
| 49.52 | 114797198 |
| 48.68 | 214215634 |
| 47.14 | 193662434 |
| 45.15 | 189908648 |
| 44.14 | 256890092 |
| 42.84 | 69214852 |
| 32.19 | 222202084 |
| 30.88 | 815357798 |
| 30.18 | 374165606 |
| 26.90 | 245211526 |
| 25.24 | 577388052 |
| 24.46 | 264825296 |
| 22.20 | 50496138 |
| 20.38 | 41759744 |

-continued

| v(F1) [ppm] | Intensity [abs] |
|---|---|
| 19.49 | 41357342 |
| 18.71 | 47277276 |
| 17.48 | 208619340 |
| 16.12 | 299572586 |
| 15.60 | 327837392 |
| 13.81 | 215875880 |
| 11.86 | 290193382 |
| 9.99 | 403708852 |
| 6.12 | 121783130 |

Representative $^{13}$C NMR chemical shifts for oxalate Type A are 167.13, 129.67, 118.41, and 30.88 ppm. Representative $^{13}$C NMR chemical shifts for oxalate Type A are also 167.13, 129.67, and 118.41 ppm.

Gentisate

Figure 35:
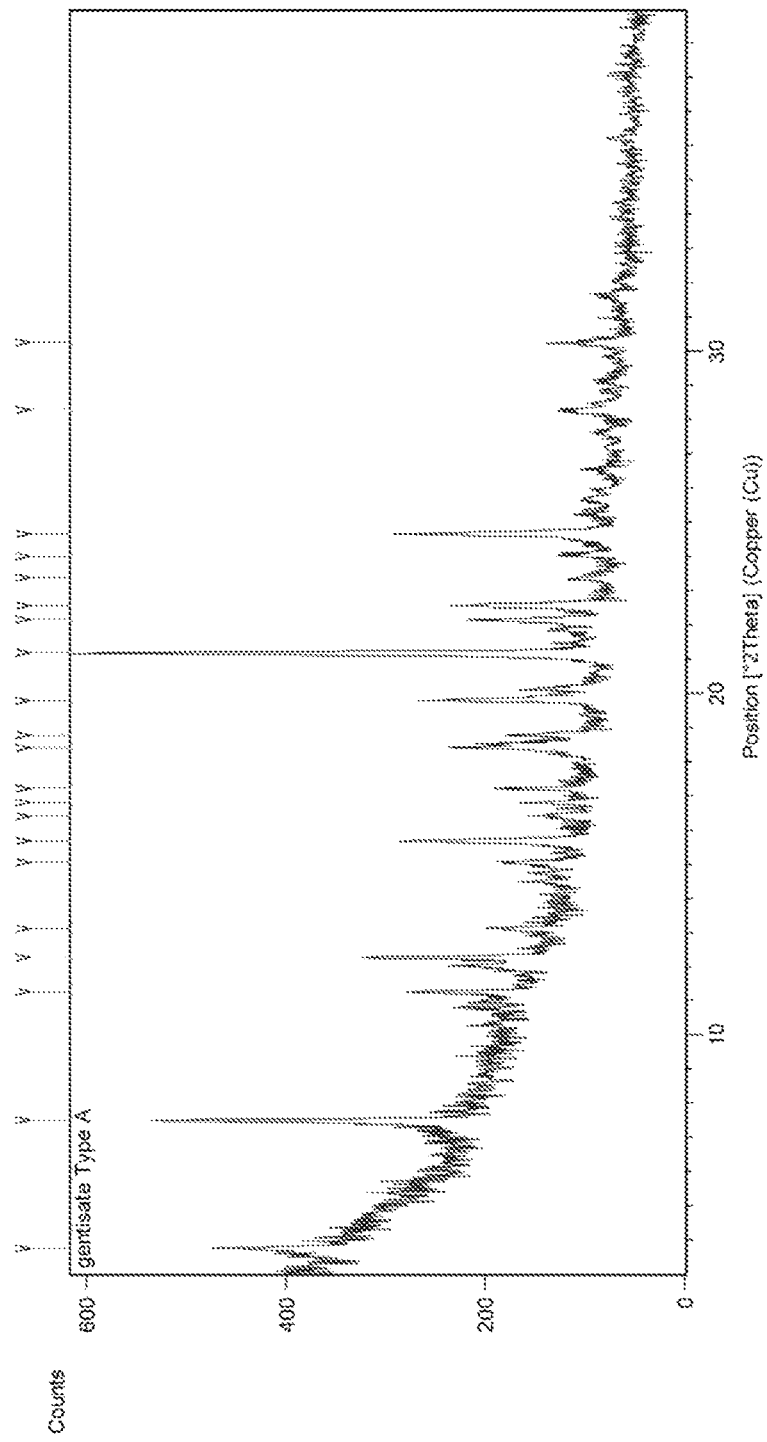
FIG. 35 is a XRPD Pattern of gentisate Type A.
Figure 36:
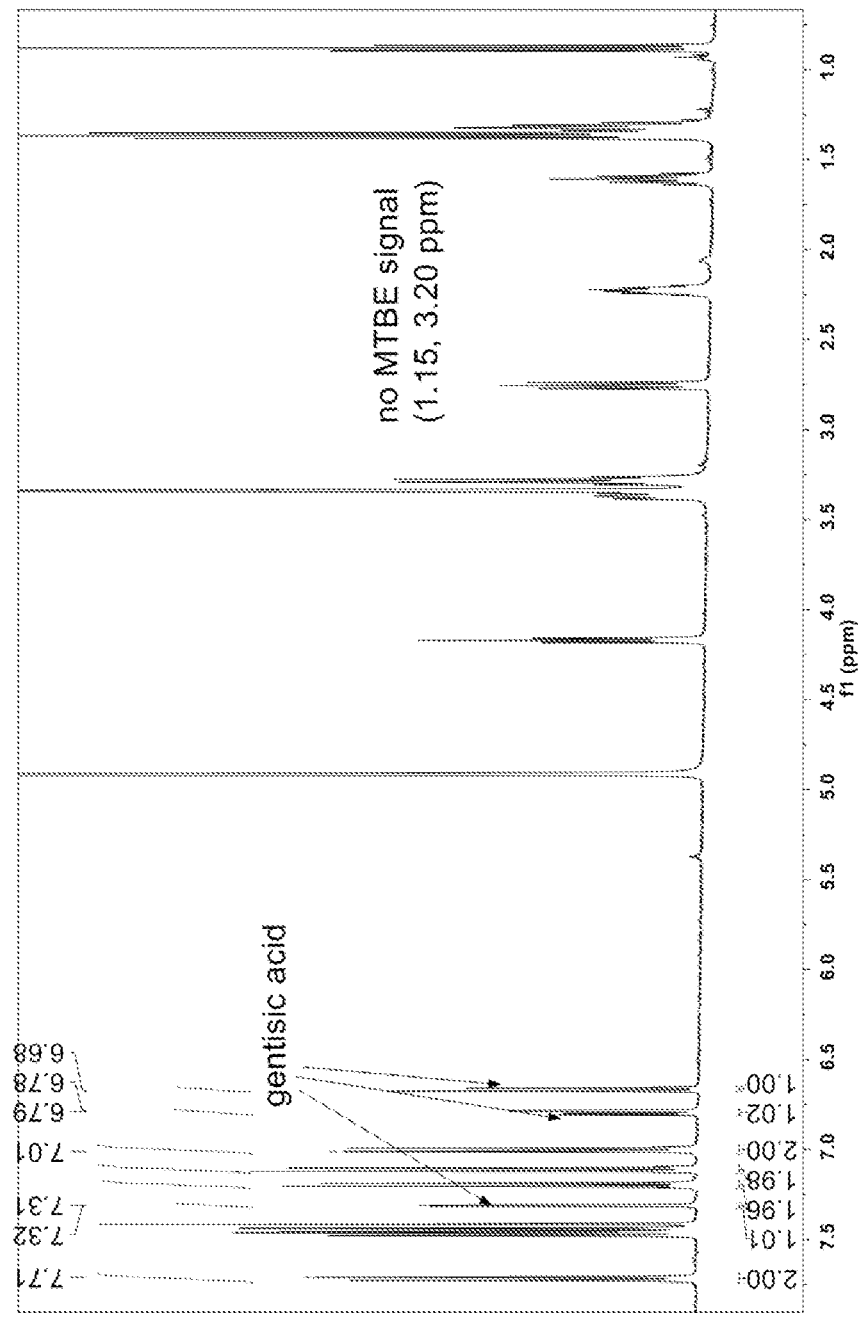
FIG. 36 is a $^1$H NMR spectrum of gentisate Type A.
Figure 37:
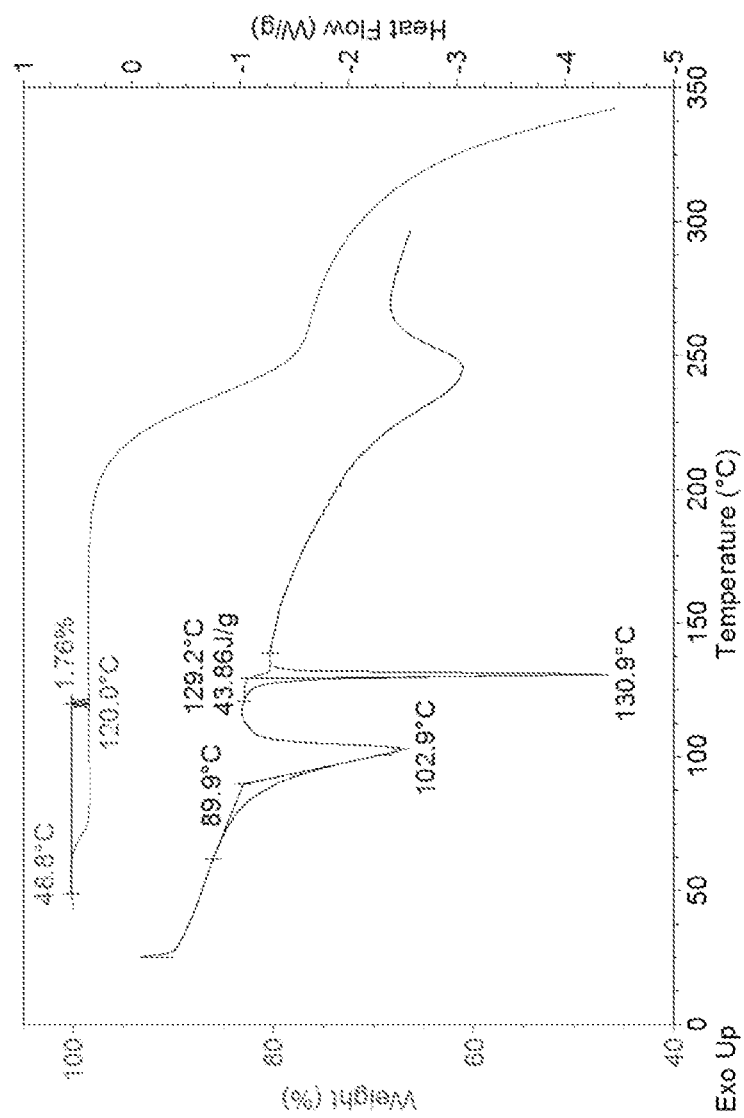
FIG. 37 is a DSC profile and a TGA of gentisate Type A.

In one aspect of the invention, the pharmaceutically acceptable salt of COMPOUND I is a gentisate. In one embodiment, the gentisate is crystalline. In one embodiment, the gentisate is crystalline and is characterized by an XRPD pattern having peaks at 2θ angles of 7.5°, 21.2°, and 24.7±0.2°. In one embodiment, the gentisate is crystalline and is characterized by an XRPD pattern having peaks at 2θ angles of 3.8°, 7.5°, 12.3°, 21.2°, and 24.7±0.2°. In one embodiment, the gentisate is crystalline and is characterized by an XRPD pattern as shown in FIG. 35. In one embodiment, the gentisate is crystalline and is characterized by a $^1$H-NMR substantially similar to FIG. 36. In one embodiment, the gentisate is crystalline and is characterized by an endothermic peak at about 103° C. and an endothermic peak at about 131° C. as determined by DSC. In one embodiment, the gentisate is crystalline and is characterized by a DSC profile as shown in FIG. 37. In one embodiment, the gentisate is crystalline and is characterized by an about 1.8 wt % loss between room temperature and about 120° C. as determined by TGA. In one embodiment, the gentisate is crystalline and is characterized by a TGA profile as shown in FIG. 37. In one embodiment, the gentisate is crystalline and is characterized by at least two of the following features (I-i)-(I-iv):

(I-i) an XRPD pattern having peaks at 2θ angles of 7.5°, 21.2°, and 24.7±0.2°;
(I-i) a $^1$H-NMR substantially as shown in FIG. 36;
(I-iii) a DSC profile as shown in FIG. 37; or
(I-iv) a TGA profile as shown in FIG. 37.

In one embodiment, the gentisate is crystalline and is gentisate Type A.

Gentisate Type A is characterized by the following XRPD pattern expressed in terms of the degree 2θ and relative intensities:

| Angle (Degree 2θ) | Relative Intensity* % |
|---|---|
| 3.8 | 33.67 |
| 7.5 | 58.03 |
| 11.3 | 21.31 |
| 12.3 | 35.02 |
| 13.1 | 11.78 |
| 15.1 | 12.12 |
| 15.7 | 33.21 |
| 16.4 | 6.75 |
| 16.8 | 10.36 |
| 17.2 | 14.49 |
| 18.4 | 24.05 |
| 18.8 | 14.25 |
| 19.8 | 33.11 |
| 21.2 | 100.00 |
| 22.1 | 24.82 |
| 22.6 | 28.52 |
| 23.4 | 4.22 |
| 24.0 | 6.91 |
| 24.7 | 41.99 |
| 28.3 | 10.12 |
| 30.3 | 9.47 |

*The relative intensities may change depending on the crystal size and morphology.

Figure 65:
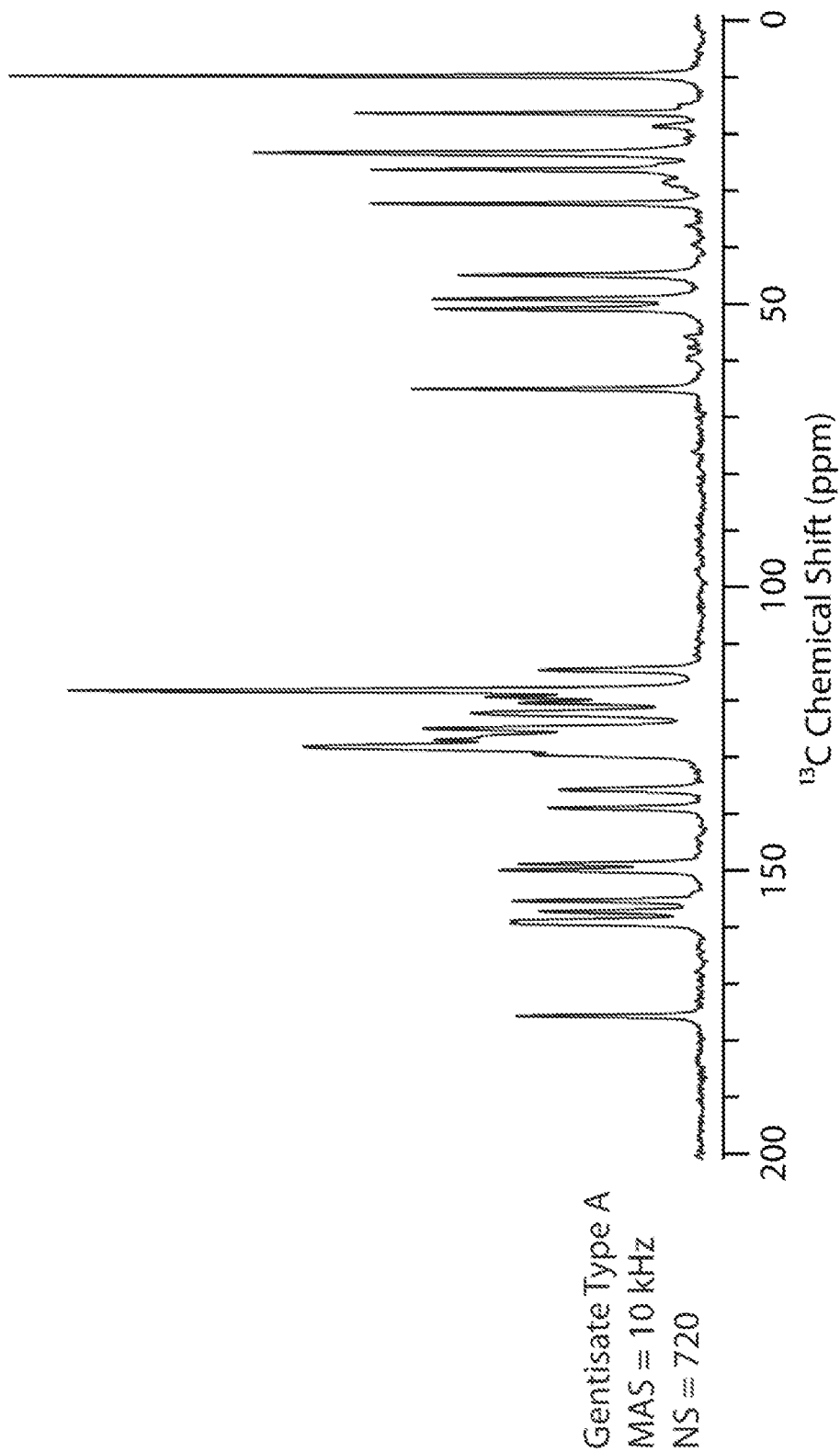
FIG. 65 is a $^{13}$C SSNMR spectrum of gentisate Type A.

In one embodiment, gentisate Type A is characterized by the SSNMR of FIG. 65. In one embodiment, gentisate Type A is characterized by the following $^{13}$C Solid State NMR shifts.

| v(F1) [ppm] | Intensity [abs] |
|---|---|
| 175.64 | 388126120 |
| 159.32 | 397869172 |
| 158.87 | 397961136 |
| 157.20 | 339475808 |
| 155.31 | 396167256 |
| 149.90 | 422353164 |
| 148.80 | 382549580 |
| 138.94 | 320161024 |
| 135.69 | 296428680 |
| 129.45 | 352643232 |
| 128.12 | 835694180 |
| 126.89 | 559127120 |
| 124.90 | 582995336 |
| 122.15 | 483027136 |
| 120.39 | 381464612 |
| 119.34 | 451353368 |
| 118.23 | 1330161012 |
| 114.58 | 338519648 |
| 64.96 | 606170172 |
| 59.85 | 29076340 |
| 59.30 | 26856152 |
| 57.57 | 25433924 |
| 55.78 | 33462768 |
| 50.85 | 558255560 |
| 49.08 | 562899892 |
| 44.84 | 508006244 |
| 36.17 | 32000524 |
| 32.25 | 693747184 |
| 29.83 | 33078072 |
| 28.43 | 78756820 |
| 26.24 | 691207596 |
| 23.22 | 940029676 |
| 20.71 | 34814676 |
| 19.74 | 29060256 |
| 18.65 | 101033564 |
| 16.26 | 726578028 |
| 14.85 | 47116228 |
| 9.69 | 1453241704 |

Representative $^{13}$C NMR chemical shifts for gentisate Type A are 128.12, 118.23, 23.22, and 9.69 ppm. Representative $^{13}$C NMR chemical shifts for gentisate Type A are also 128.12, and 118.23 ppm.

Figure 38:
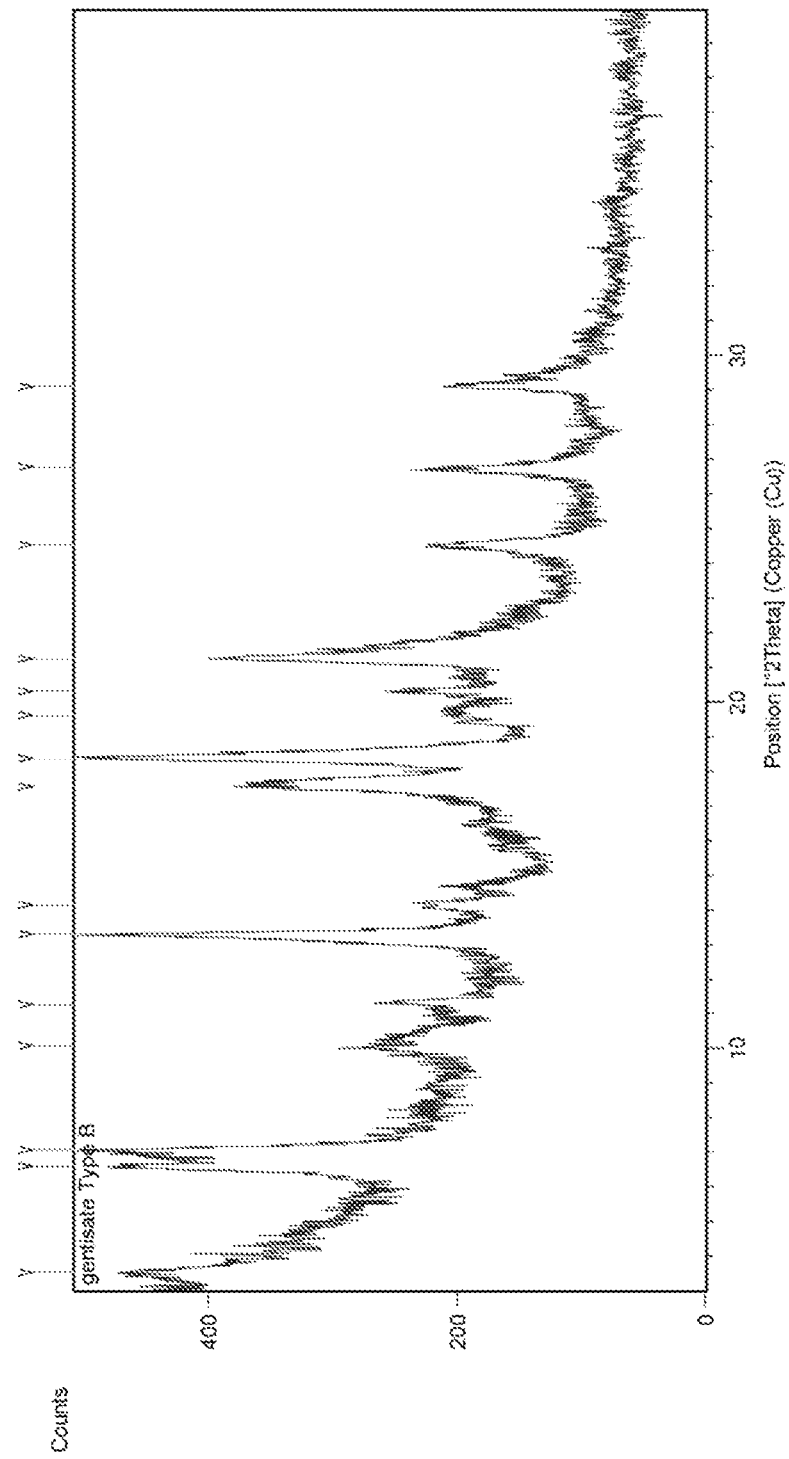
FIG. 38 is a XRPD Pattern of gentisate Type B.

In one embodiment, the gentisate is crystalline and is characterized by an XRPD pattern having peaks at 2θ angles of 13.3°, 18.4°, and 21.2±0.2°. In one embodiment, the gentisate is crystalline and is characterized by an XRPD pattern having peaks at 2θ angles of 7.1°, 13.3°, 188.4°, and 21.2±0.2°. In one embodiment, the gentisate is crystalline and is characterized by an XRPD pattern as shown in FIG. 38. In one embodiment, the gentisate is crystalline and is characterized by a $^1$H-NMR substantially similar to FIG. 39.

Figure 39:
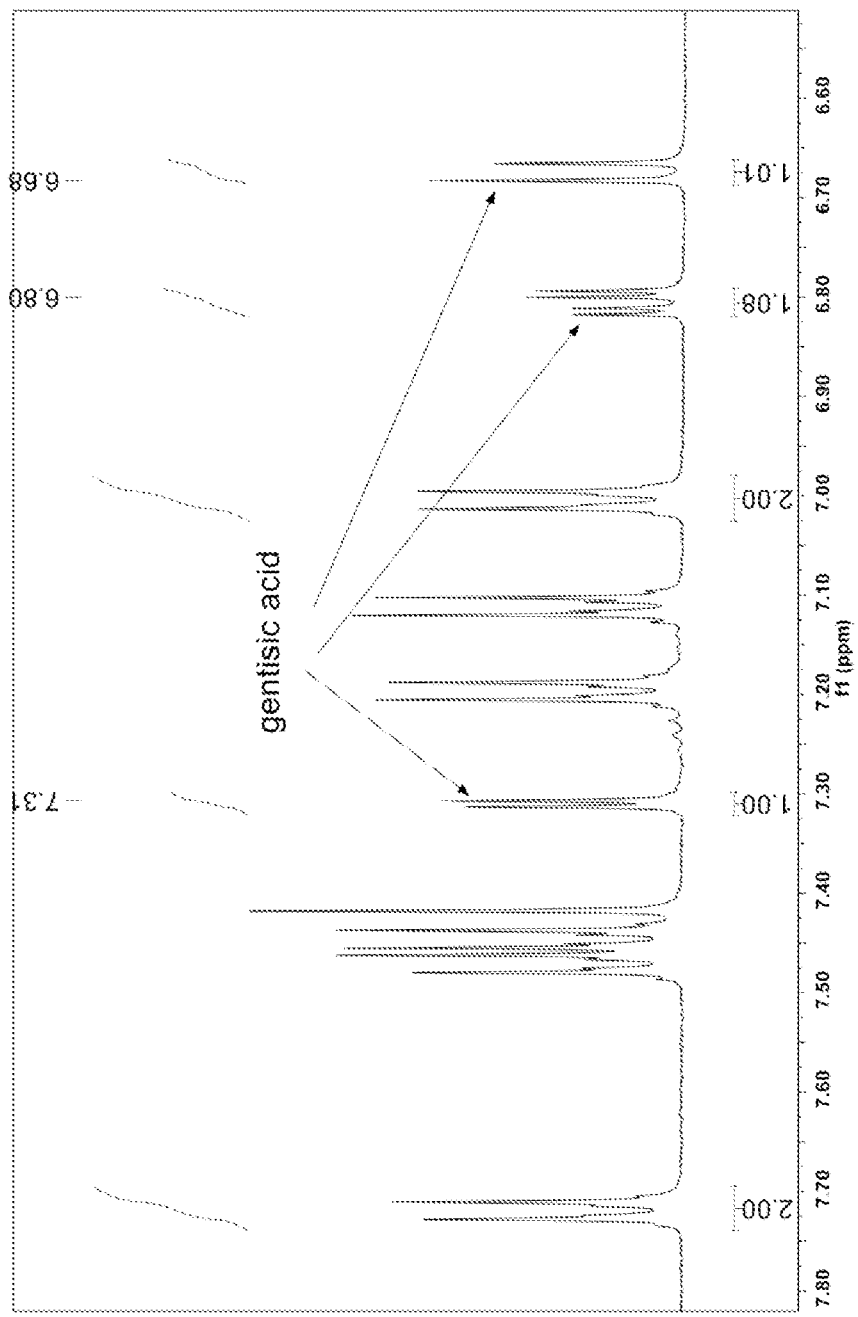
FIG. 39 is a $^1$H NMR spectrum of gentisate Type B.
Figure 40:
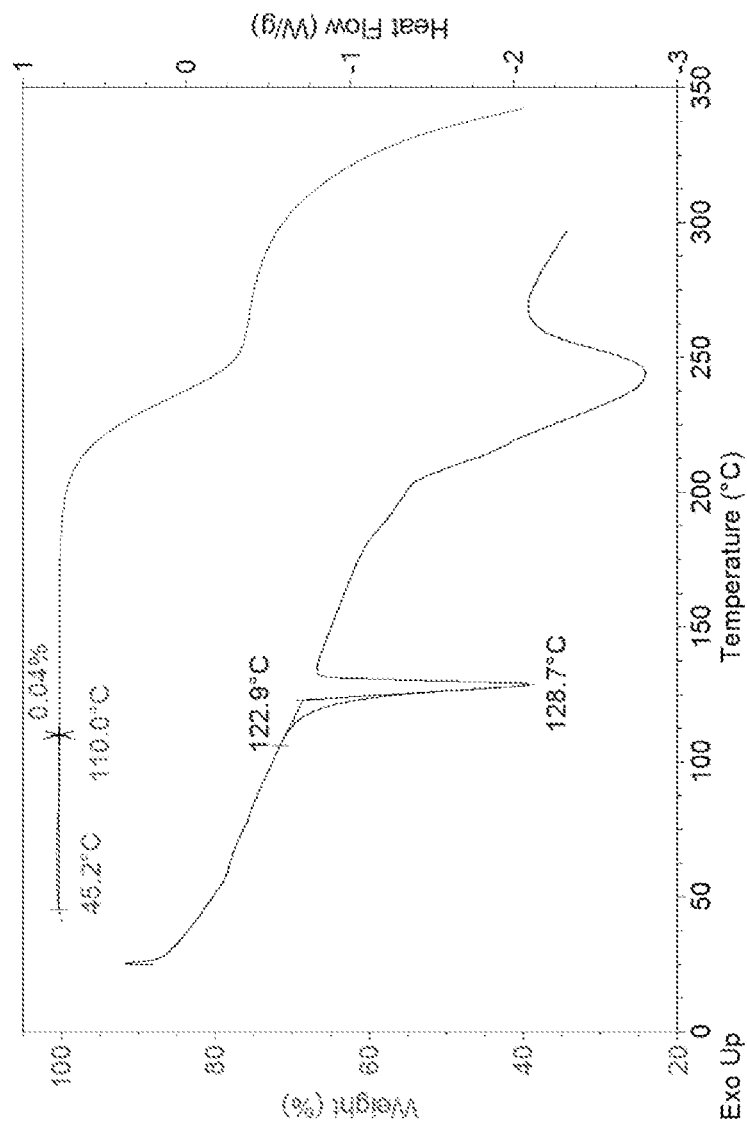
FIG. 40 is a DSC profile and a TGA of gentisate Type B.

In one embodiment, the gentisate is crystalline and is characterized by an endothermic peak at about 129° C. as determined by DSC. In one embodiment, the gentisate is crystalline and is characterized by a DSC profile as shown in FIG. 40. In one embodiment, the gentisate is crystalline and is characterized by a TGA profile as shown in FIG. 40. In one embodiment, the gentisate is crystalline and is characterized by at least two of the following features (I-i)-(I-iv):
- (I-i) an XRPD pattern having peaks at 2θ angles of 13.3°, 18.4°, and 21.2±0.2°;
- (I-li) a $^1$H-NMR as shown in FIG. 39;
- (I-iii) a DSC profile as shown in FIG. 40; or
- (I-iv) a TGA profile as shown in FIG. 40.

In one embodiment, the gentisate is crystalline and is gentisate Type B.

Gentisate Type B is characterized by the following XRPD pattern expressed in terms of the degree 2θ and relative intensities:

| Angle (Degree 2θ) | Relative Intensity* % |
| --- | --- |
| 3.5 | 48.33 |
| 6.6 | 61.35 |
| 7.1 | 75.61 |
| 10.1 | 20.11 |
| 11.3 | 15.08 |
| 13.3 | 93.49 |
| 14.1 | 20.85 |
| 17.6 | 58.99 |
| 18.4 | 100.00 |
| 19.6 | 15.08 |
| 20.3 | 28.53 |
| 21.2 | 76.23 |
| 24.5 | 33.97 |
| 26.8 | 33.79 |
| 29.1 | 35.50 |

*The relative intensities may change depending on the crystal size and morphology.

Mesylate

Figure 41:
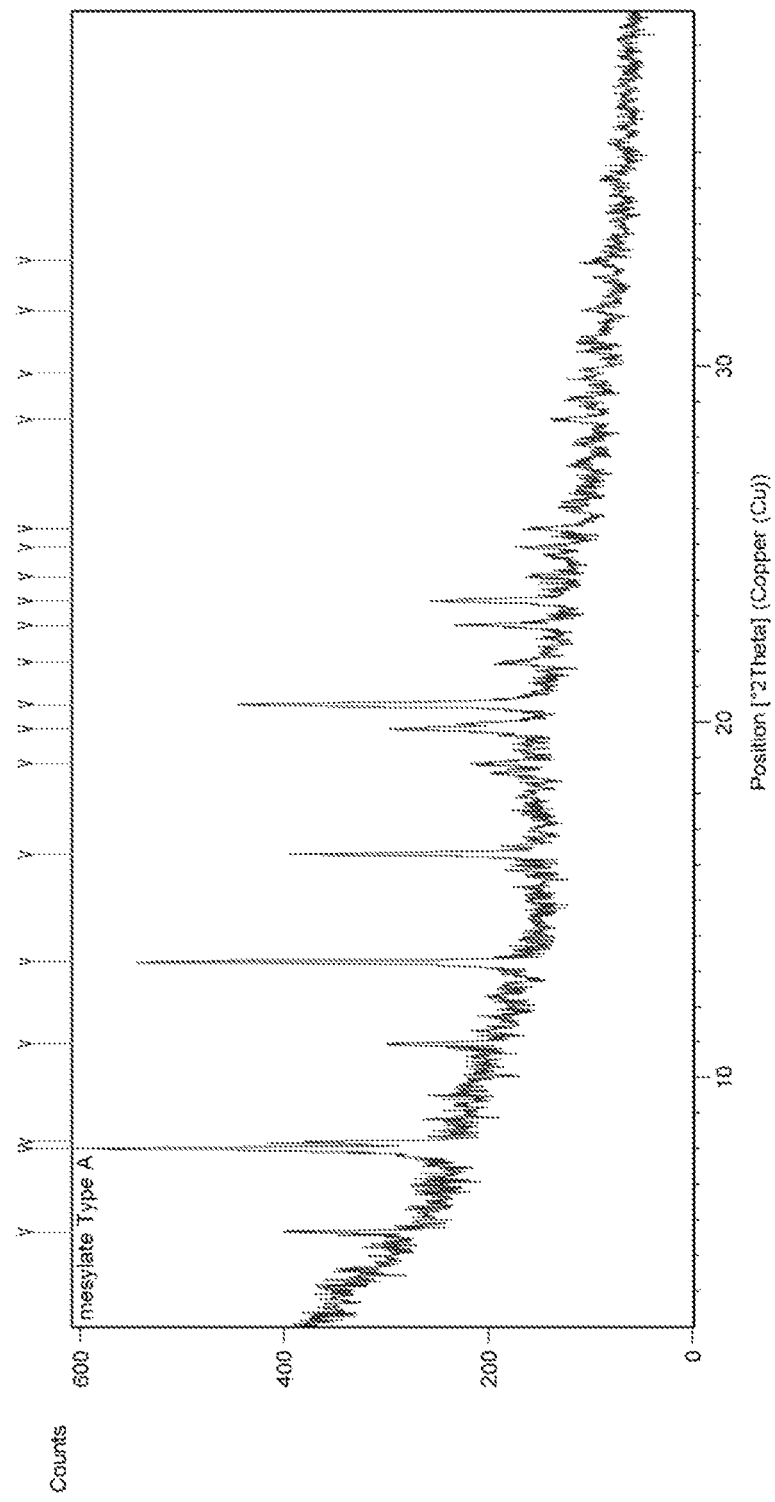
FIG. 41 is a XRPD Pattern of mesylate Type A.

In one aspect of the invention, the pharmaceutically acceptable salt of COMPOUND I is a mesylate. In one embodiment, the mesylate is crystalline. In one embodiment, the mesylate is crystalline and is characterized by an XRPD pattern having peaks at 2θ angles of 8.0°, 13.3°, and 20.5±0.2°. In one embodiment, the mesylate is crystalline and is characterized by an XRPD pattern having peaks at 2θ angles of 8.0°, 13.3°, 16.3°, 20.5°, and 23.4±0.2°. In one embodiment, the mesylate is crystalline and is characterized by an XRPD pattern as shown in FIG. 41. In one embodiment, the mesylate is crystalline and is mesylate Type A.

Mesylate Type A is characterized by the following XRPD pattern expressed in terms of the degree 2θ and relative intensities:

| Angle (Degree 2θ) | Relative Intensity* % |
| --- | --- |
| 5.7 | 27.93 |
| 8.0 | 100.00 |
| 8.2 | 42.21 |
| 11.0 | 29.69 |
| 13.3 | 91.69 |
| 16.3 | 61.13 |
| 18.8 | 19.89 |
| 19.8 | 43.59 |
| 20.5 | 84.36 |
| 21.7 | 14.13 |
| 22.7 | 26.91 |
| 23.4 | 38.96 |
| 24.1 | 12.59 |
| 24.9 | 16.59 |
| 25.4 | 13.78 |
| 28.5 | 10.67 |
| 29.8 | 3.33 |
| 31.6 | 6.33 |
| 33.0 | 4.40 |

*The relative intensities may change depending on the crystal size and morphology.

Figure 42:
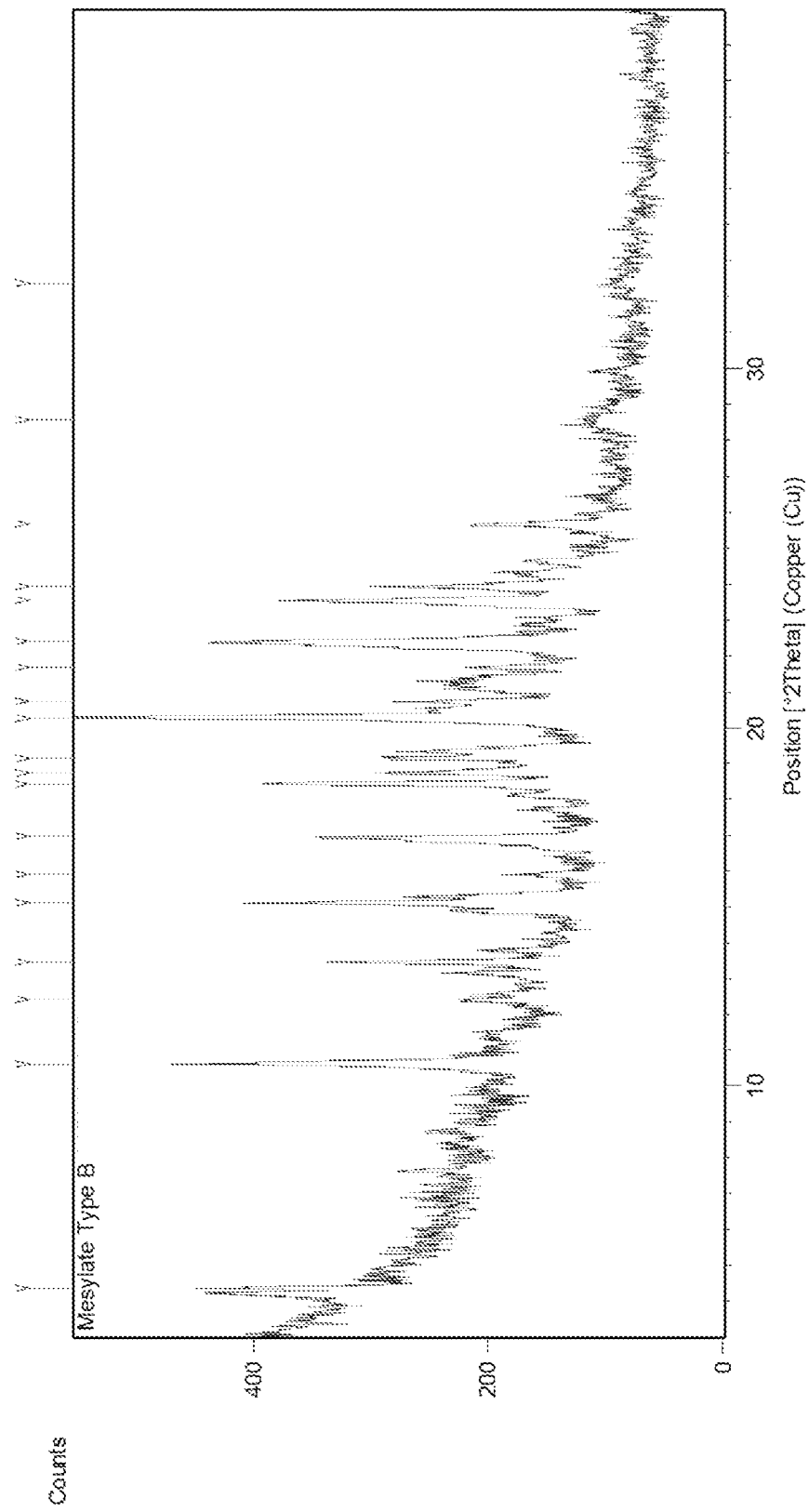
FIG. 42 is a XRPD Pattern of mesylate Type B.
Figure 43:
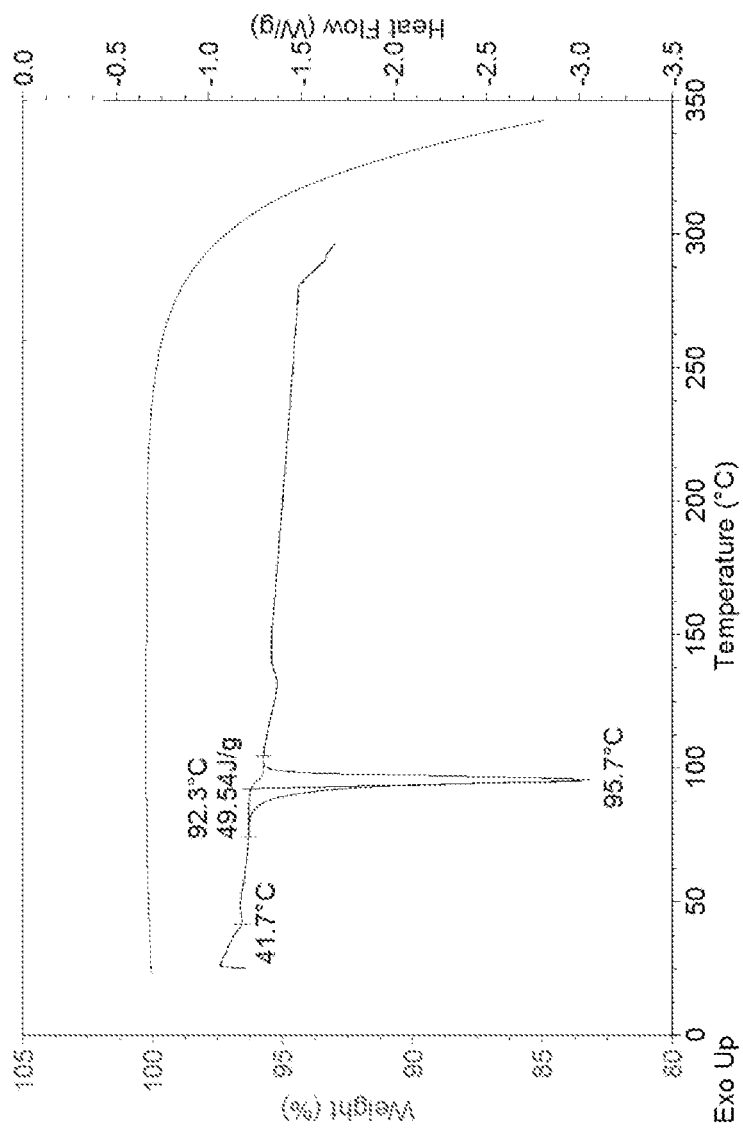
FIG. 43 a DSC profile and a TGA of mesylate Type B.

In one embodiment, the mesylate is crystalline and is characterized by an XRPD pattern having peaks at 2θ angles of 20.3°, 22.4°, and 23.5±0.2°. In one embodiment, the mesylate is crystalline and is characterized by an XRPD pattern having peaks at 2θ angles of 10.6, 15.1, 20.3°, 22.4°, and 23.5±0.2°. In one embodiment, the mesylate is crystalline and is characterized by an XRPD pattern as shown in FIG. 42. In one embodiment, the mesylate is crystalline and is characterized by an endothermic peak at about 96° C. as determined by DSC. In one embodiment, the mesylate is crystalline and is characterized by a DSC profile as shown in FIG. 43. In one embodiment, the mesylate is crystalline and is characterized by a TGA profile as shown in FIG. 43. In one embodiment, the mesylate is crystalline and is characterized by at least two of the following features (I-i)-(I-ii):
- (I-i) an XRPD pattern having peaks at 2θ angles of 20.3°, 22.4°, and 23.5±0.2°;
- (I-i) a DSC profile as shown in FIG. 43; or
- (I-iii) a TGA profile as shown in FIG. 43.

In one embodiment, the mesylate is crystalline and is mesylate Type B.

Mesylate Type B is characterized by the following XRPD pattern expressed in terms of the degree 2θ and relative intensities:

| Angle (Degree 2θ) | Relative Intensity* % |
| --- | --- |
| 4.4 | 27.41 |
| 10.6 | 59.14 |
| 12.4 | 9.81 |
| 13.5 | 36.78 |
| 15.1 | 60.36 |
| 15.9 | 9.61 |
| 17.0 | 38.32 |
| 18.4 | 54.14 |
| 18.7 | 39.11 |
| 19.1 | 37.20 |
| 20.3 | 100.00 |
| 20.7 | 35.76 |
| 21.7 | 23.42 |
| 22.4 | 68.24 |
| 23.5 | 58.81 |
| 23.9 | 40.32 |
| 25.7 | 25.20 |
| 28.6 | 6.24 |
| 32.4 | 3.46 |

*The relative intensities may change depending on the crystal size and morphology.

Figure 66:
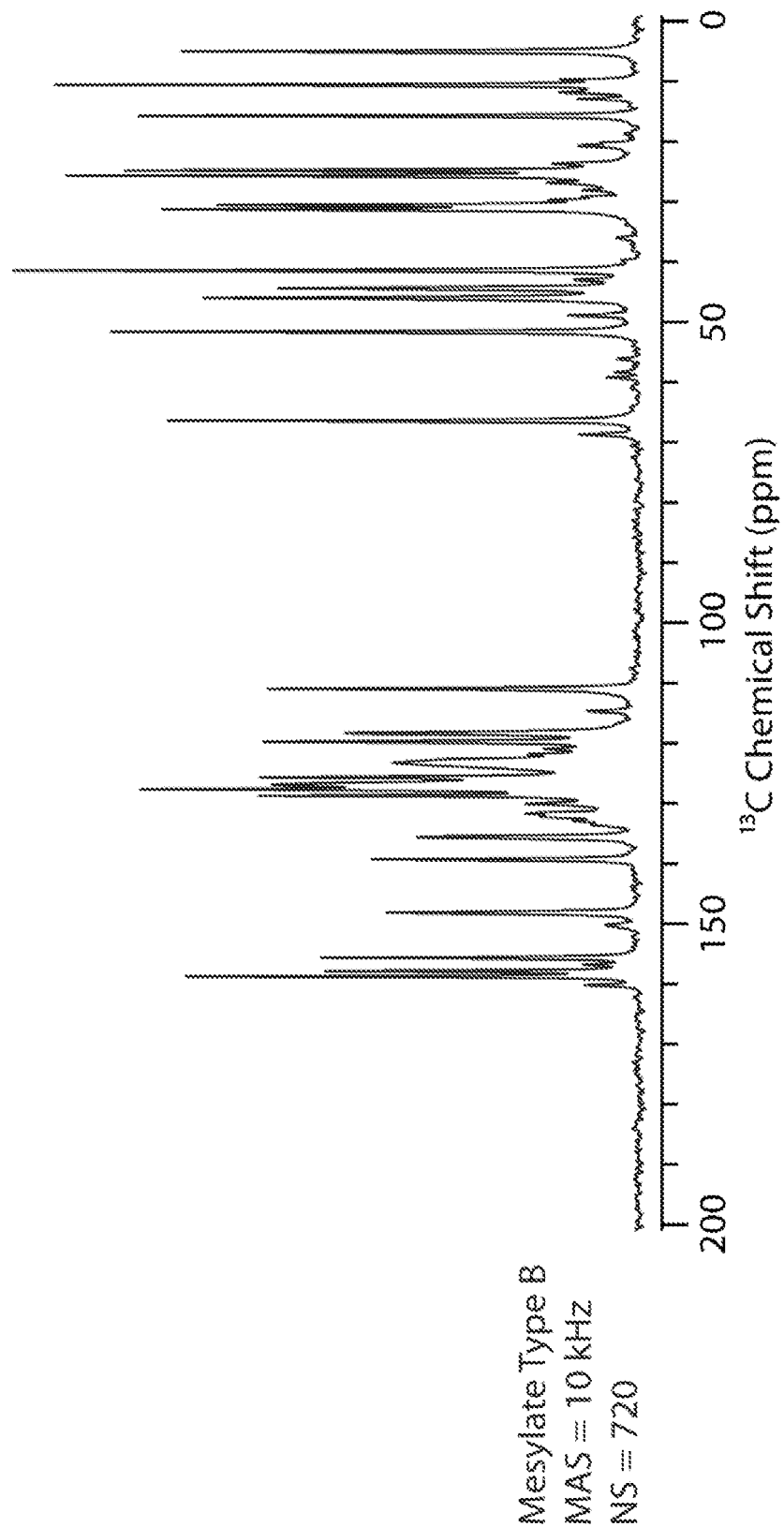
FIG. 66 is a $^{13}$C SSNMR spectrum of mesylate Type B.

In one embodiment, mesylate Type B is characterized by the SSNMR of FIG. 66. In one embodiment, mesylate Type B is characterized by the following $^{13}$C Solid State NMR shifts.

| v(F1) [ppm] | Intensity [abs] |
|---|---|
| 160.15 | 107037188 |
| 158.70 | 928036196 |
| 157.81 | 641379716 |
| 156.74 | 109724892 |
| 155.59 | 650099120 |
| 150.18 | 64150604 |
| 148.10 | 514950388 |
| 139.25 | 545412572 |
| 135.52 | 451822192 |
| 133.48 | 95482268 |
| 132.84 | 132682816 |
| 132.12 | 201350028 |
| 131.61 | 229276820 |
| 130.01 | 229130408 |
| 128.66 | 779295088 |
| 127.58 | 1020018376 |
| 126.84 | 750204424 |
| 125.59 | 775718216 |
| 123.18 | 503212296 |
| 121.81 | 223733560 |
| 120.89 | 192474676 |
| 119.72 | 767372640 |
| 118.28 | 601906948 |
| 114.62 | 103532068 |
| 110.89 | 759529176 |
| 68.62 | 119050900 |
| 66.35 | 964600800 |
| 59.16 | 62432340 |
| 58.26 | 45135492 |
| 56.08 | 40769096 |
| 51.57 | 1080705032 |
| 48.87 | 141496596 |
| 47.90 | 30199116 |
| 45.93 | 890501292 |
| 44.33 | 737220576 |
| 42.92 | 129125384 |
| 41.39 | 1280961344 |
| 39.72 | 33271364 |
| 35.94 | 42099356 |
| 31.21 | 975687332 |
| 30.53 | 861937980 |
| 29.65 | 183059252 |
| 29.13 | 114804932 |
| 28.04 | 111664996 |
| 26.74 | 185659044 |
| 25.61 | 1173610016 |
| 24.72 | 1051998076 |
| 23.65 | 174313008 |
| 20.64 | 121962288 |
| 20.15 | 76511512 |
| 15.66 | 1023449264 |
| 12.85 | 121875572 |
| 11.77 | 161033060 |
| 11.38 | 117958704 |
| 10.53 | 1196114180 |
| 9.67 | 159023624 |
| 4.97 | 937051400 |

Representative $^{13}$C NMR chemical shifts for mesylate Type B are 158.70, 127.58, 51.57, and 41.39 ppm. Representative $^{13}$C NMR chemical shifts for mesylate Type B are also 158.70, and 127.58 ppm.

Hydrobromide

Figure 44:
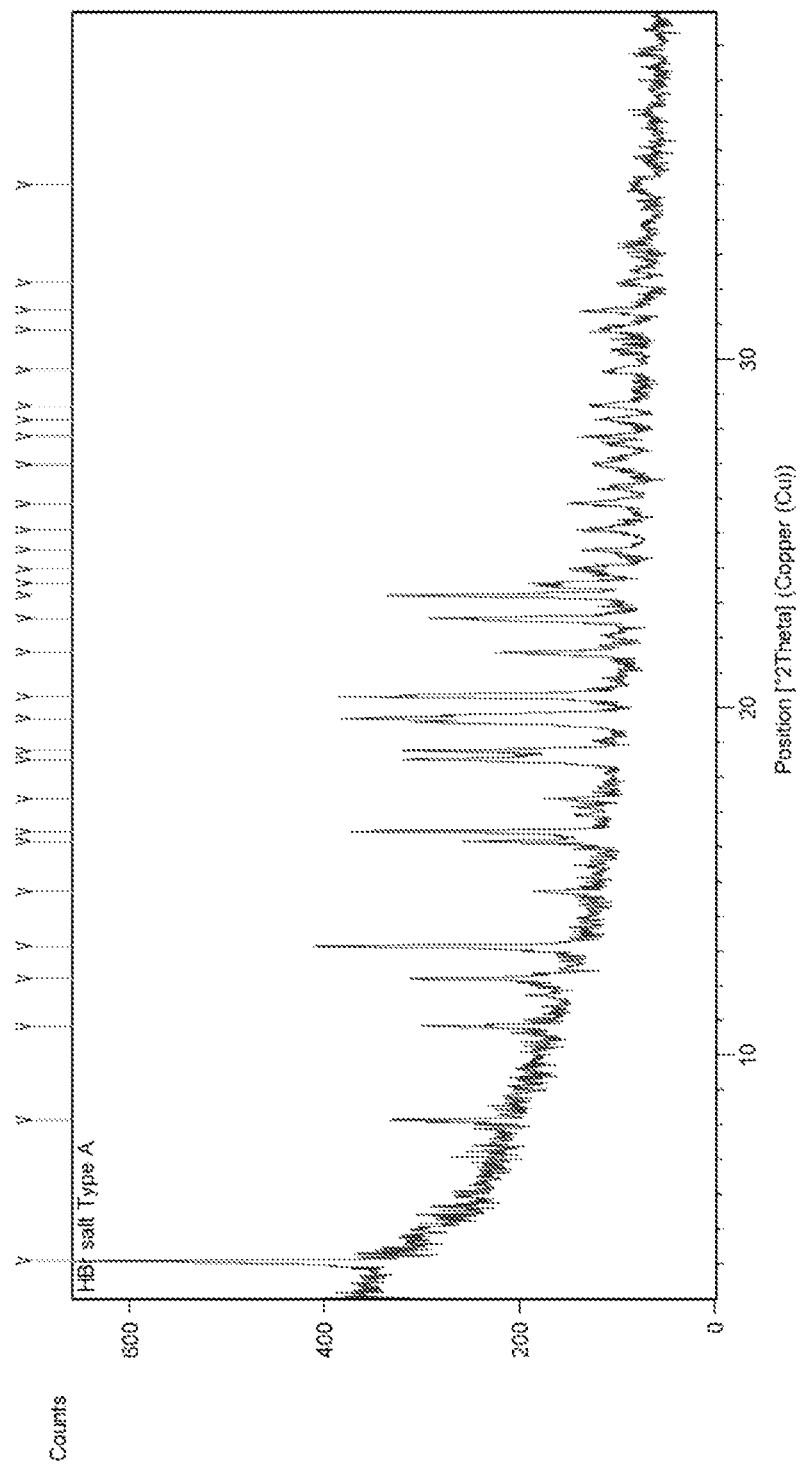
FIG. 44 is a XRPD Pattern of HBr Type A.
Figure 45:
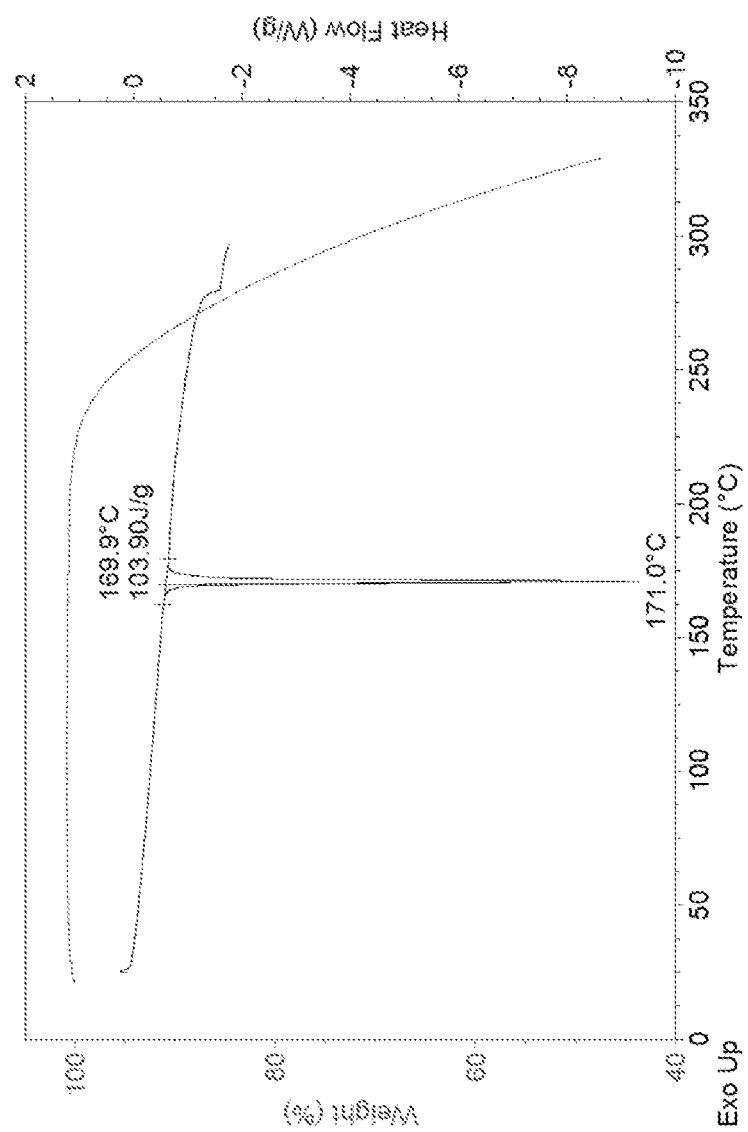
FIG. 45 is a DSC profile and a TGA of HBr Type A.

In one aspect of the invention, the pharmaceutically acceptable salt of COMPOUND I is a hydrobromide. In one embodiment, the pharmaceutically acceptable salt of COMPOUND I is a mono-hydrobromide. In one embodiment, the hydrobromide is crystalline. In one embodiment, the hydrobromide is crystalline and is characterized by an XRPD pattern having peaks at 2θ angles of 4.1°, 13.1°, and 16.4±0.2°. In one embodiment, the hydrobromide is crystalline and is characterized by an XRPD pattern having peaks at 2θ angles of 4.1°, 13.1°, 16.4°, 19.7°, and 20.3±0.2°. In one embodiment, the hydrobromide is crystalline and is characterized by an XRPD pattern as shown in FIG. 44. In one embodiment, the hydrobromide is crystalline and is characterized by an endothermic peak at about 171° C. as determined by DSC. In one embodiment, the hydrobromide is crystalline and is characterized by a DSC profile as shown in FIG. 45. In one embodiment, the hydrobromide is crystalline and is characterized by a TGA profile as shown in FIG. 45. In one embodiment, the hydrobromide is crystalline and is characterized by at least two of the following features (I-i)-(I-ii):

(I-i) an XRPD pattern having peaks at 2θ angles of 4.1°, 13.1°, and 16.4±0.2°;

(I-i) a DSC profile as shown in FIG. 45; or (I-iii) a TGA profile as shown in FIG. 45.

In one embodiment, the hydrobromide is crystalline and is hydrobromide Type A.

Hydrobromide Type A is characterized by the following XRPD pattern expressed in terms of the degree 2θ and relative intensities:

| Angle (Degree 2θ) | Relative Intensity* % |
|---|---|
| 4.1 | 100.00 |
| 8.2 | 32.86 |
| 10.8 | 30.78 |
| 12.2 | 43.93 |
| 13.1 | 74.71 |
| 14.7 | 15.95 |
| 16.1 | 36.66 |
| 16.4 | 68.37 |
| 17.4 | 14.11 |
| 18.5 | 53.47 |
| 18.8 | 58.08 |
| 19.7 | 70.71 |
| 20.3 | 73.09 |
| 21.6 | 31.96 |
| 22.5 | 46.55 |
| 23.2 | 65.50 |
| 23.6 | 22.82 |
| 24.0 | 12.46 |
| 24.5 | 12.31 |
| 25.1 | 12.12 |
| 25.8 | 16.12 |
| 27.0 | 11.85 |
| 27.8 | 14.32 |
| 28.3 | 9.81 |
| 28.7 | 13.23 |
| 29.7 | 9.00 |
| 30.8 | 12.72 |
| 31.4 | 14.67 |
| 32.2 | 6.11 |
| 35.0 | 5.24 |

*The relative intensities may change depending on the crystal size and morphology.

Figure 67:
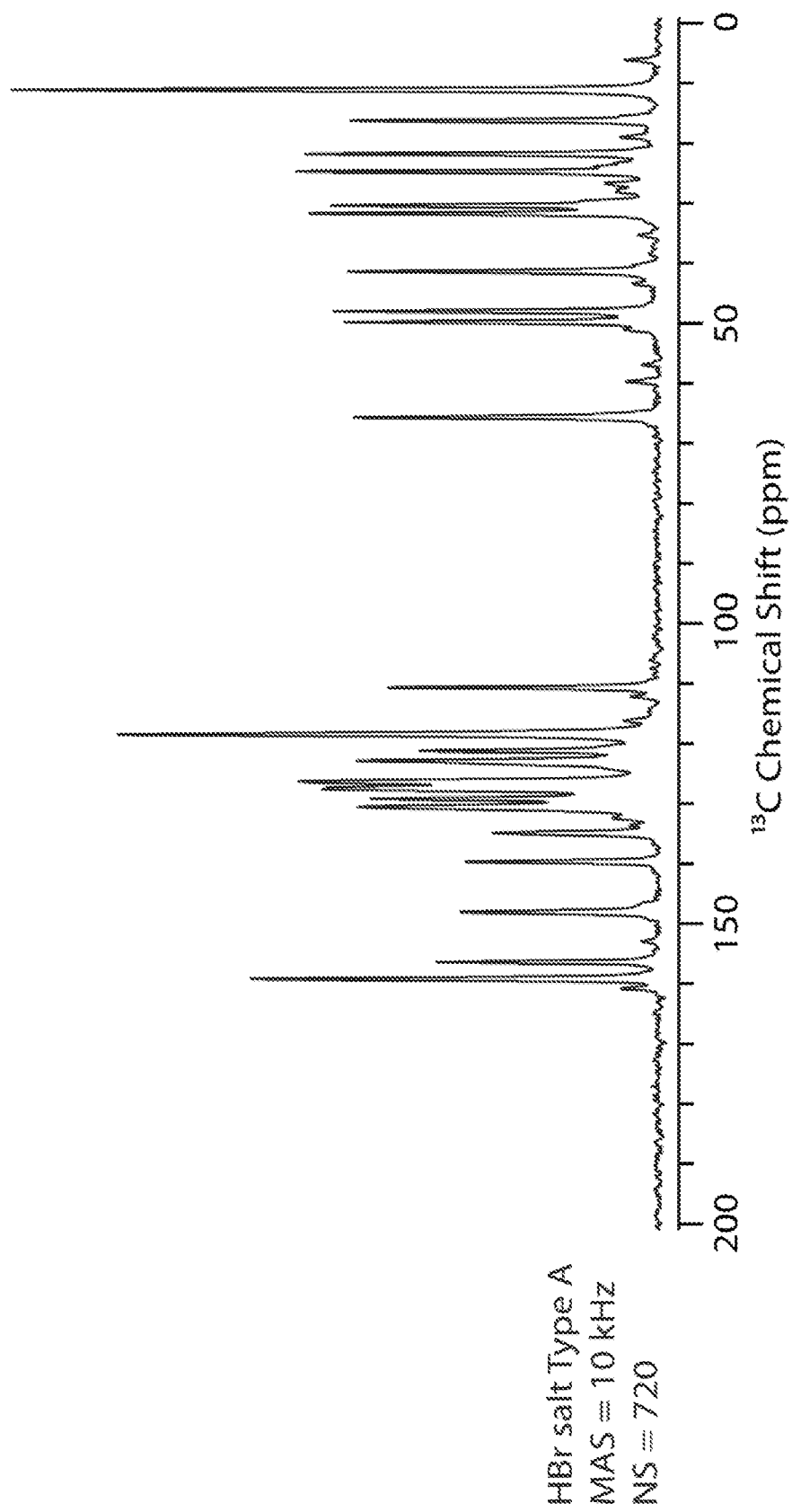
FIG. 67 is a $^{13}$C SSNMR spectrum of HBr salt Type A.

In one embodiment, hydrobromide Type A is characterized by the SSNMR of FIG. 67. In one embodiment, hydrobromide Type A is characterized by the following $^{13}$C Solid State NMR shifts.

| v(F1) [ppm] | Intensity [abs] |
|---|---|
| 160.77 | 78975796 |
| 159.17 | 900820132 |
| 156.39 | 488279680 |
| 152.94 | 35074052 |
| 148.05 | 435855320 |
| 139.67 | 423327252 |
| 134.88 | 362833304 |
| 133.60 | 60722160 |
| 132.32 | 97684752 |
| 130.52 | 662005396 |
| 129.18 | 633877400 |
| 127.58 | 742032000 |

-continued

| v(F1) [ppm] | Intensity [abs] |
|---|---|
| 127.28 | 731963268 |
| 126.26 | 793908276 |
| 122.82 | 664579756 |
| 121.20 | 525539720 |
| 118.47 | 1193583580 |
| 116.21 | 73827648 |
| 112.15 | 58966988 |
| 110.65 | 595114040 |
| 65.63 | 671203092 |
| 59.66 | 68614588 |
| 56.86 | 32545400 |
| 50.95 | 73309356 |
| 49.74 | 692825604 |
| 47.97 | 716472772 |
| 43.38 | 54071676 |
| 41.34 | 684891836 |
| 40.27 | 53097912 |
| 35.29 | 41341848 |
| 31.66 | 769671896 |
| 30.35 | 721082572 |
| 28.09 | 89879756 |
| 27.67 | 88439012 |
| 26.65 | 116394568 |
| 24.66 | 799253396 |
| 23.89 | 140259800 |
| 23.29 | 95686976 |
| 21.75 | 779204728 |
| 18.96 | 80946744 |
| 17.74 | 26855784 |
| 16.18 | 678358048 |
| 11.06 | 1428996012 |
| 6.08 | 71604928 |

Representative $^{13}$C NMR chemical shifts for hydrobromide Type A are 118.47, 65.63, 31.66, and 11.06 ppm. Representative $^{13}$C NMR chemical shifts for hydrobromide Type A are also 159.17 and 118.47 ppm.

Figure 46:
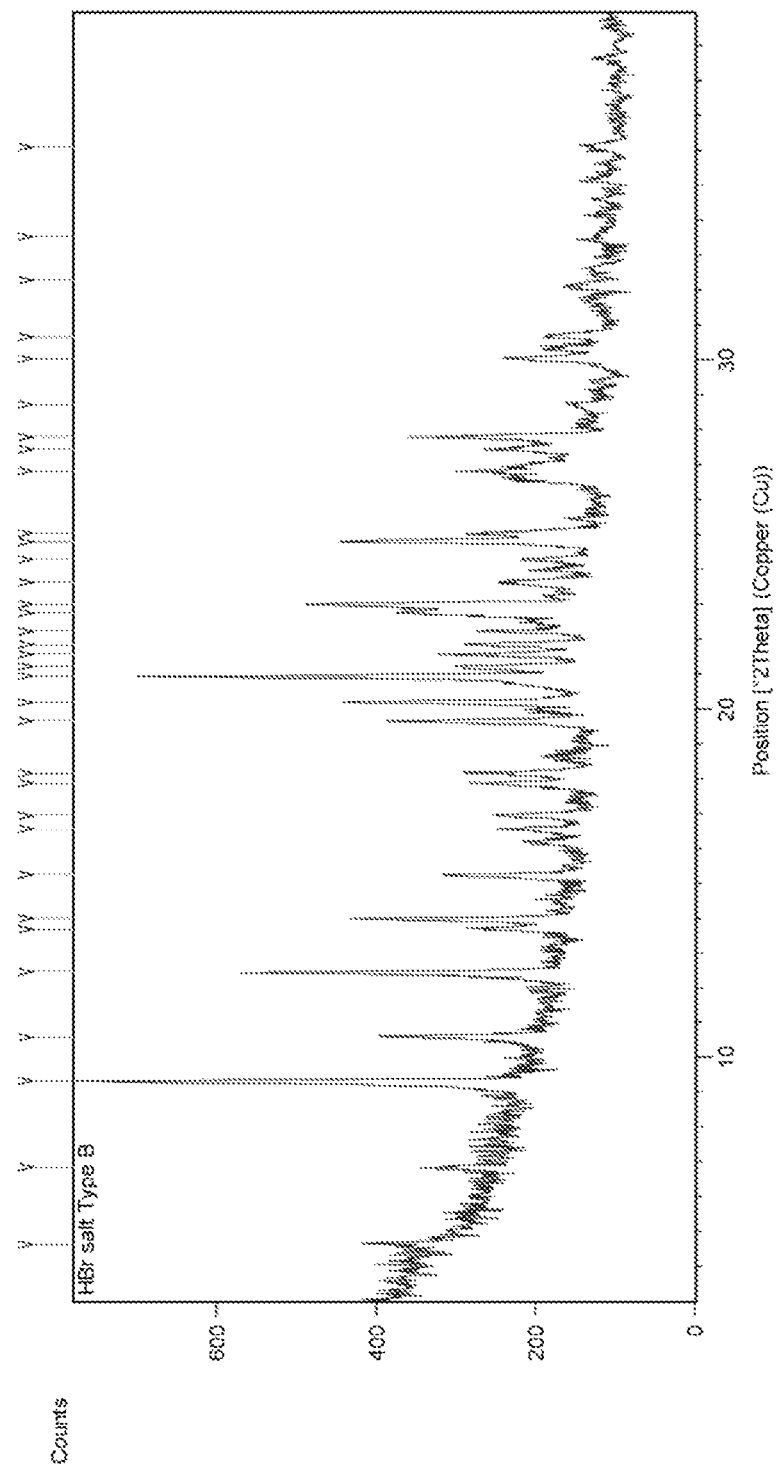
FIG. 46 is a XRPD Pattern of HBr Type B.
Figure 47:
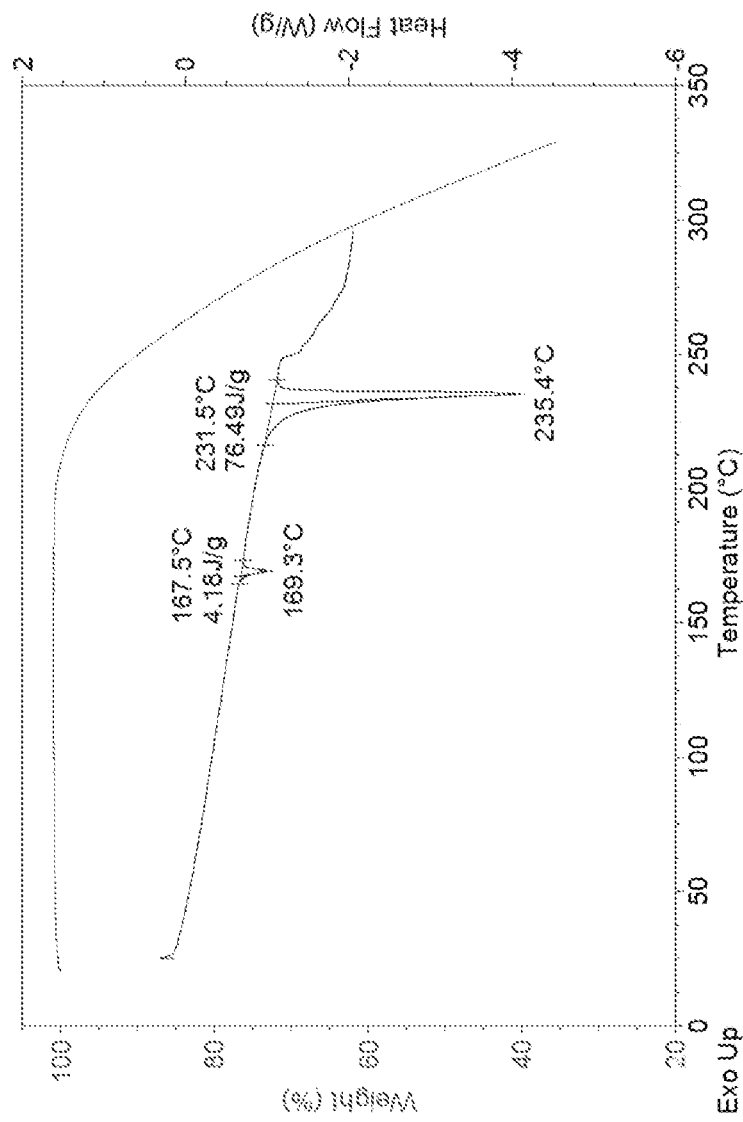
FIG. 47 is a DSC profile and a TGA of HBr Type B.

In one embodiment, the pharmaceutically acceptable salt is a di-hydrobromide. In one embodiment, the hydrobromide is crystalline and is characterized by an XRPD pattern having peaks at 2θ angles of 9.3°, 20.9°, and 23.0±0.2°. In one embodiment, the hydrobromide is crystalline and is characterized by an XRPD pattern having peaks at 2θ angles of 9.3°, 12.4°, 20.2°, 20.9°, and 23.0±0.2°. In one embodiment, the hydrobromide is crystalline and is characterized by an XRPD pattern as shown in FIG. 46. In one embodiment, the hydrobromide is crystalline and is characterized by melting peak at about 231.5° C. (onset temperature) as determined by DSC. In one embodiment, the hydrobromide is crystalline and is characterized by a DSC profile as shown in FIG. 47. In one embodiment, the hydrobromide is crystalline and is characterized by a TGA profile as shown in FIG. 47. In one embodiment, the hydrobromide is crystalline and is characterized by at least two of the following features (I-i)-(I-ii):

(I-i) an XRPD pattern having peaks at 2θ angles of 9.3°, 20.9°, and 23.0±0.2°;

(I-i) a DSC profile as shown in FIG. 47; or (I-iii) a TGA profile as shown in FIG. 47.

In one embodiment, the hydrobromide is crystalline and is hydrobromide Type B.

Hydrobromide Type B is characterized by the following XRPD pattern expressed in terms of the degree 2θ and relative intensities:

| Angle (Degree 2θ) | Relative Intensity* % |
|---|---|
| 4.6 | 11.25 |
| 6.8 | 11.30 |
| 9.3 | 100.00 |
| 10.6 | 35.00 |
| 12.4 | 60.59 |
| 13.7 | 18.68 |
| 14.0 | 45.03 |
| 15.3 | 23.00 |
| 16.6 | 14.85 |
| 16.9 | 19.22 |
| 17.9 | 23.34 |
| 18.2 | 22.62 |
| 19.7 | 34.34 |
| 20.2 | 50.42 |
| 20.9 | 98.99 |
| 21.2 | 28.84 |
| 21.5 | 29.87 |
| 21.9 | 27.19 |
| 22.2 | 20.46 |
| 22.7 | 40.91 |
| 23.0 | 63.42 |
| 23.6 | 19.27 |
| 24.3 | 16.46 |
| 24.8 | 55.90 |
| 25.0 | 25.96 |
| 26.8 | 25.32 |
| 27.4 | 24.14 |
| 27.8 | 41.26 |
| 28.7 | 6.74 |
| 30.0 | 21.02 |
| 30.7 | 13.41 |
| 32.3 | 3.80 |
| 33.5 | 3.90 |
| 36.1 | 6.45 |

*The relative intensities may change depending on the crystal size and morphology.

Figure 68:
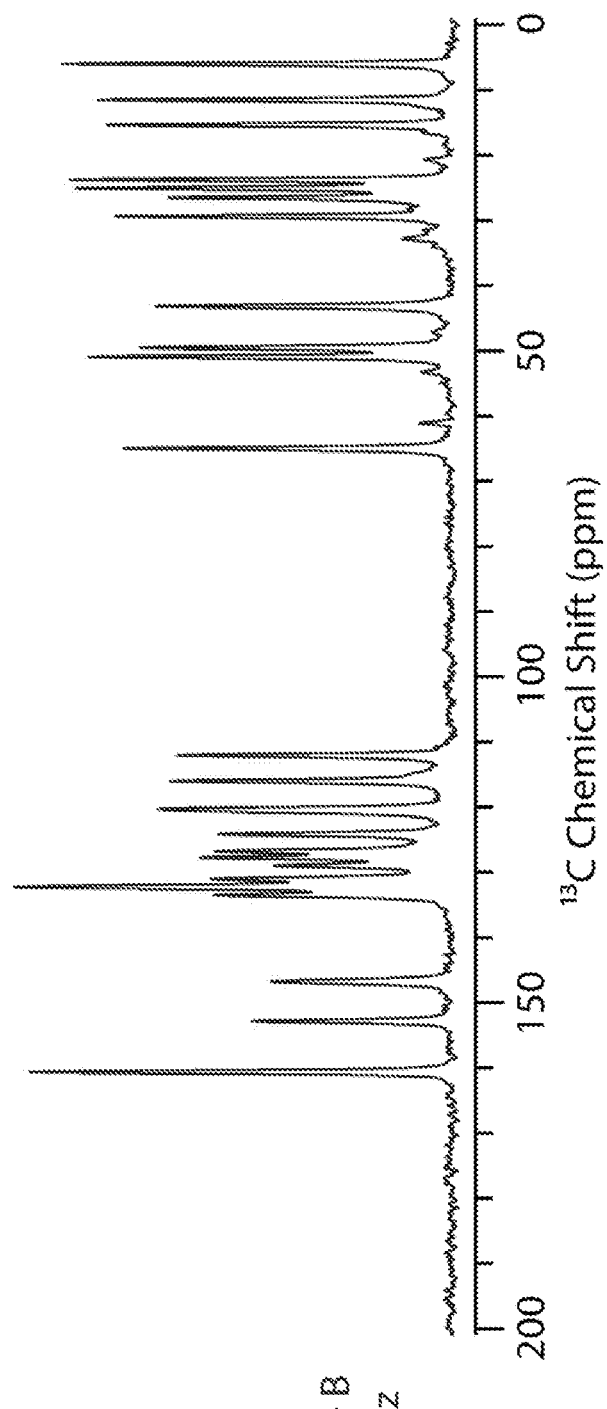
FIG. 68 is a $^{13}$C SSNMR spectrum of HBr salt Type B.

In one embodiment, hydrobromide Type B is characterized by the SSNMR of FIG. 68. In one embodiment, hydrobromide Type B is characterized by the following $^{13}$C Solid State NMR shifts.

| v(F1) [ppm] | Intensity [abs] |
|---|---|
| 160.62 | 796339352 |
| 152.82 | 374900970 |
| 146.73 | 338675372 |
| 133.46 | 446590962 |
| 132.22 | 824821780 |
| 131.00 | 452758588 |
| 128.97 | 332667934 |
| 127.69 | 472774942 |
| 126.76 | 444218690 |
| 124.13 | 437438918 |
| 122.02 | 37808100 |
| 120.28 | 552743840 |
| 118.79 | 29154536 |
| 115.97 | 528876606 |
| 112.03 | 516946528 |
| 110.82 | 30002168 |
| 64.94 | 619338160 |
| 61.10 | 57397878 |
| 53.23 | 53792678 |
| 50.90 | 683256338 |
| 49.50 | 586689026 |
| 47.20 | 33739424 |
| 43.14 | 556673516 |
| 34.03 | 33216196 |
| 32.80 | 89619780 |
| 31.44 | 50091782 |
| 29.34 | 633764372 |
| 28.16 | 79882454 |
| 26.47 | 533027526 |
| 25.02 | 708330536 |
| 23.71 | 719096218 |
| 20.62 | 48647684 |

| v(F1) [ppm] | Intensity [abs] |
|---|---|
| 16.45 | 54451400 |
| 15.30 | 649876544 |
| 13.30 | 21743720 |
| 11.46 | 666391562 |
| 5.95 | 734721304 |

Representative $^{13}$C NMR chemical shifts for hydrobromide Type B are 160.62, 132.22, 29.34, and 23.71 ppm. Representative $^{13}$C NMR chemical shifts for hydrobromide Type B are also 160.62 and 132.22 ppm.

4-Aminosalicylate

Figure 48:
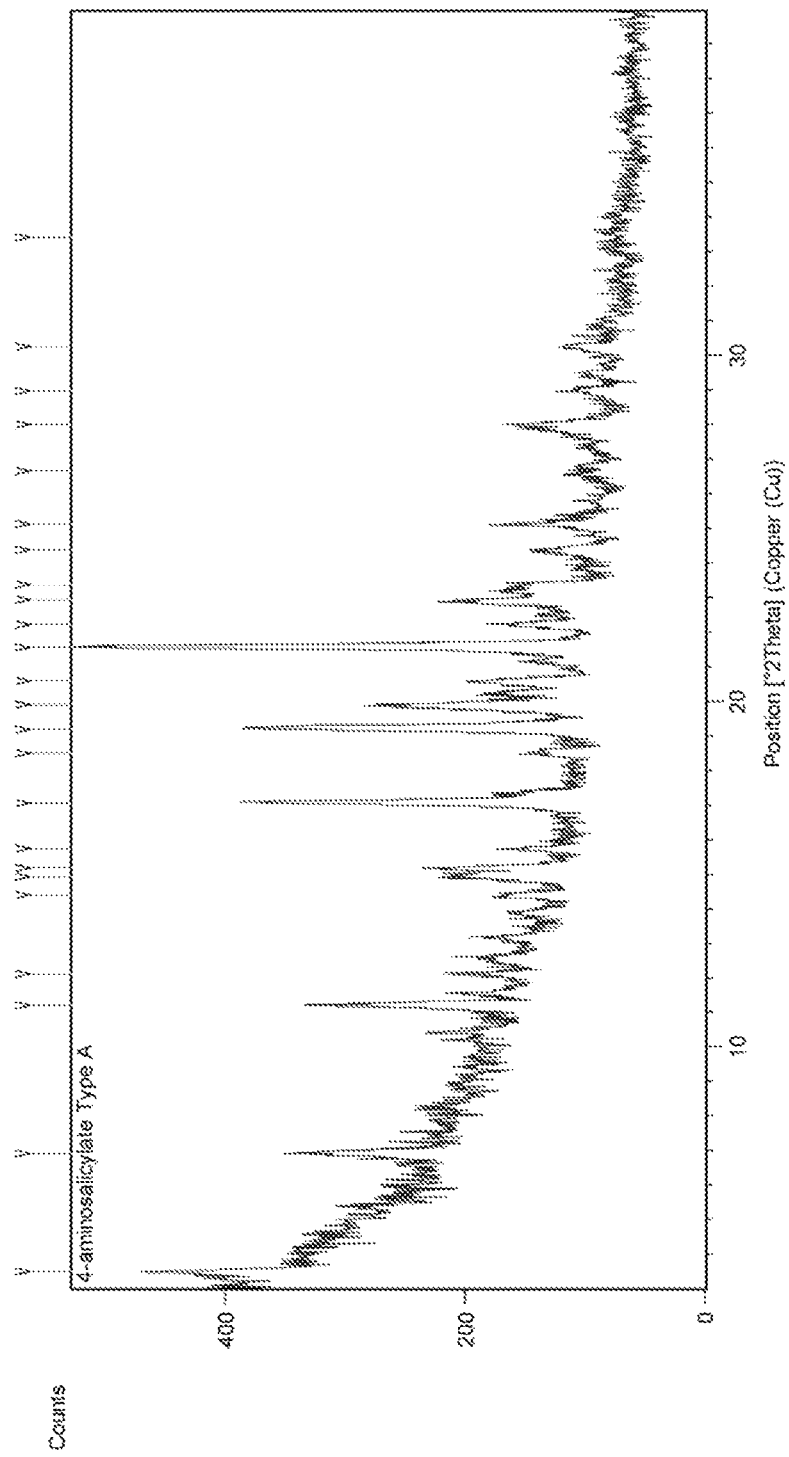
FIG. 48 is a XRPD Pattern of 4-aminosalicylate Type A.
Figure 49:
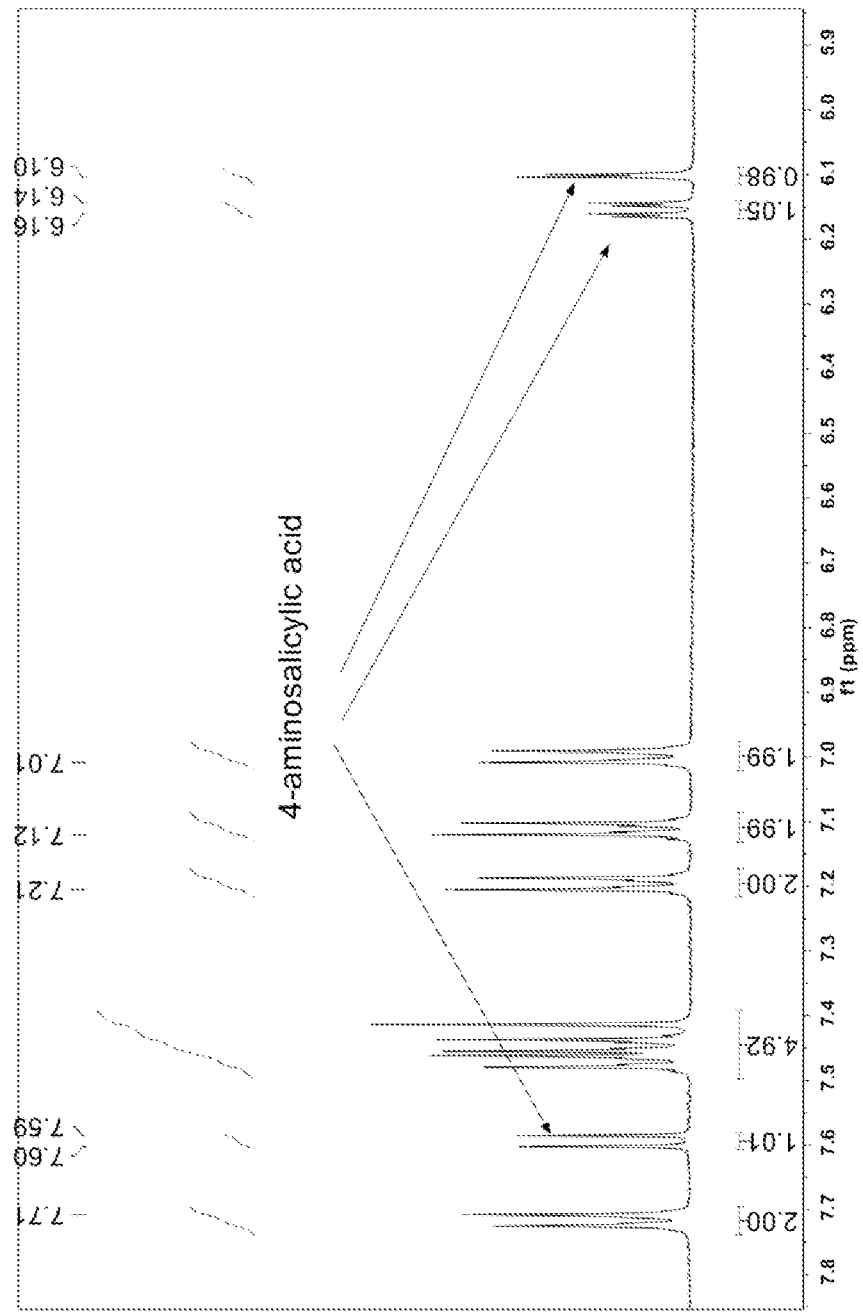
FIG. 49 is a $^1$H NMR spectrum of 4-aminosalicylate Type A.
Figure 50:
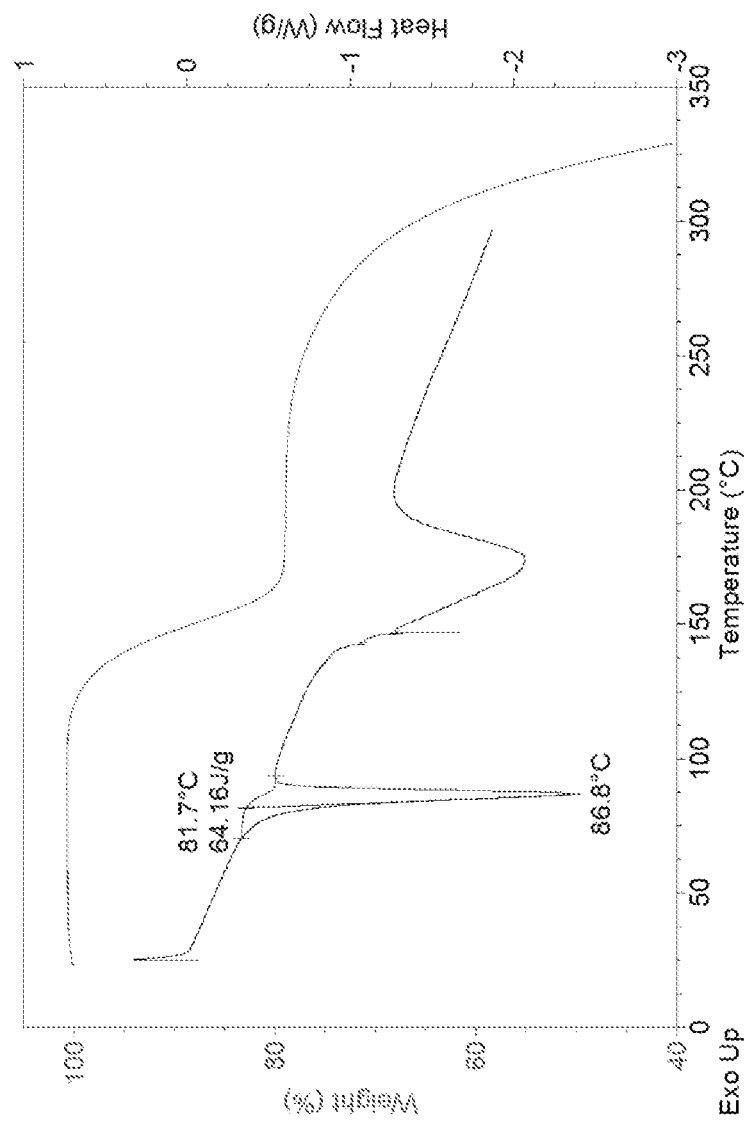
FIG. 50 is a DSC profile and a TGA of 4-aminosalicylate Type A.
Figure 51:
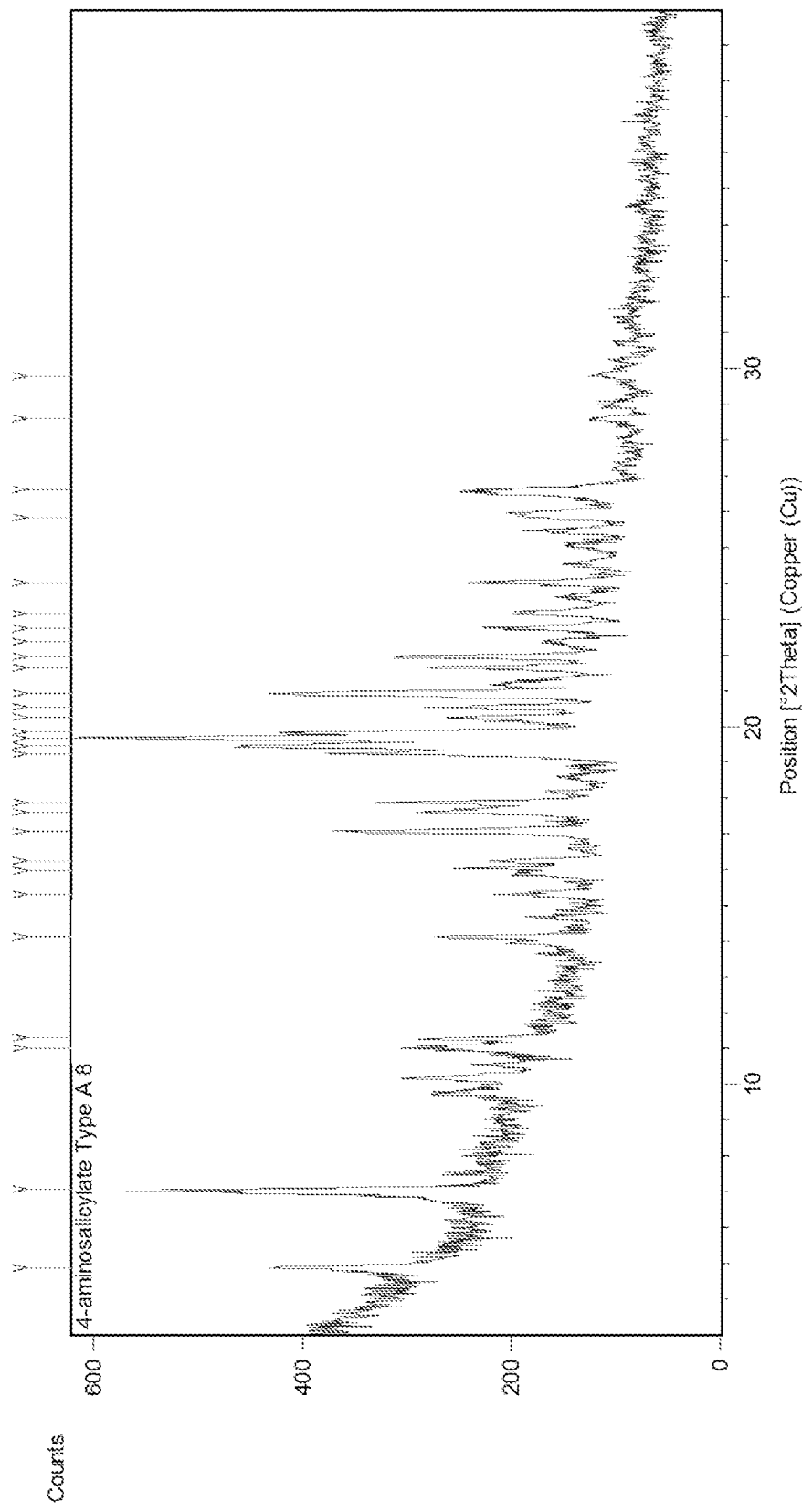
FIG. 51 is a XRPD Pattern of 4-aminosalicylate Type B.

In one aspect of the invention, the pharmaceutically acceptable salt of COMPOUND I is a 4-aminosalicylate. In one embodiment, the pharmaceutically acceptable salt of COMPOUND I is a mono-4-aminosalicylate. In one embodiment, the 4-aminosalicylate is crystalline. In one embodiment, the 4-aminosalicylate is crystalline and is characterized by an XRPD pattern having peaks at 2θ angles of 17.1°, 19.2°, and 21.5±0.2°. In one embodiment, the 4-aminosalicylate is crystalline and is characterized by an XRPD pattern having peaks at 2θ angles of 3.5°, 11.2°, 17.1°, 19.2°, and 21.5±0.2°. In one embodiment, the 4-aminosalicylate is crystalline and is characterized by an XRPD pattern as shown in FIG. 48. In one embodiment, the 4-aminosalicylate is crystalline and is crystalline and is characterized by a $^1$H-NMR substantially similar to FIG. 49. In one embodiment, the 4-aminosalicylate is crystalline and is characterized by an endothermic peak at about 87° C. as determined by DSC. In one embodiment, the 4-aminosalicylate is crystalline and is characterized by a DSC profile as shown in FIG. 50. In one embodiment, the 4-aminosalicylate is crystalline and is characterized by a TGA profile as shown in FIG. 50. In one embodiment, the 4-aminosalicylate is crystalline and is characterized by at least two of the following features (I-i)-(I-iv):

(I-i) an XRPD pattern having peaks at 2θ angles of 17.1°, 19.2°, and 21.5±0.2°;
(I-li) a $^1$H-NMR as shown in FIG. 49;
(I-iii) a DSC profile as shown in FIG. 50; or
(I-iii) a TGA profile as shown in FIG. 51.

In one embodiment, the 4-aminosalicylate is crystalline and is 4-aminosalicylate Type A.

4-Aminosalicylate Type A is characterized by the following XRPD pattern expressed in terms of the degree 2θ and relative intensities:

| Angle (Degree 2θ) | Relative Intensity* % |
|---|---|
| 3.5 | 40.77 |
| 6.9 | 28.96 |
| 11.2 | 39.94 |
| 12.1 | 6.97 |
| 14.4 | 8.10 |
| 14.9 | 21.19 |
| 15.2 | 23.87 |
| 15.7 | 10.55 |
| 17.1 | 63.75 |
| 18.5 | 9.27 |
| 19.2 | 65.81 |
| 19.9 | 41.43 |
| 20.6 | 22.49 |
| 21.5 | 100.00 |
| 22.2 | 17.52 |
| 22.9 | 27.59 |
| 23.4 | 15.67 |
| 24.4 | 11.63 |
| 25.1 | 17.40 |
| 26.6 | 4.43 |
| 28.0 | 17.98 |
| 29.0 | 8.25 |
| 30.2 | 11.35 |
| 33.4 | 0.70 |

*The relative intensities may change depending on the crystal size and morphology.

Figure 52:
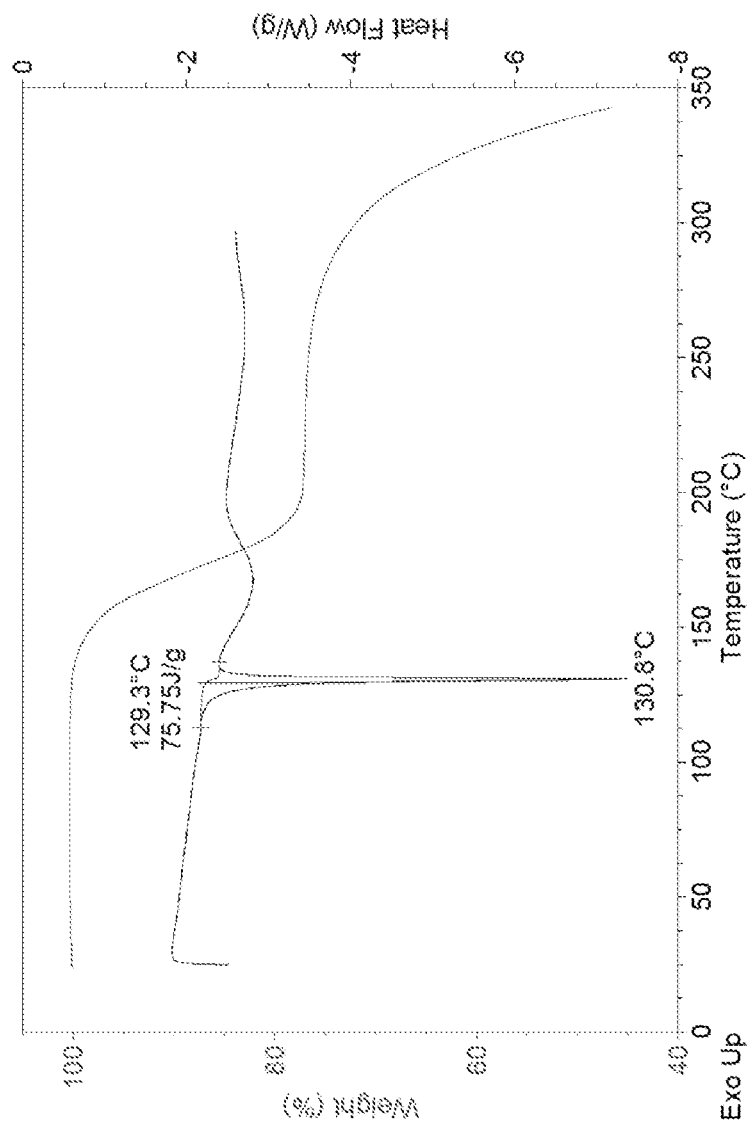
FIG. 52 is a DSC profile and a TGA of 4-aminosalicylate Type B.

In one embodiment, the 4-aminosalicylate is crystalline and is characterized by an XRPD pattern having peaks at 2θ angles of 7.1°, 19.2°, and 20.9±0.2°. In one embodiment, the 4-aminosalicylate is crystalline and is characterized by an XRPD pattern having peaks at 2θ angles of 7.1°, 17.1°, 17.6°, 19.2°, and 20.9±0.2°. In one embodiment, the 4-aminosalicylate is crystalline and is characterized by an XRPD pattern as shown in FIG. 51. In one embodiment, the 4-aminosalicylate is crystalline and is characterized by an endothermic peak at about 131° C. as determined by DSC. In one embodiment, the 4-aminosalicylate is crystalline and is characterized by a DSC profile as shown in FIG. 52. In one embodiment, the 4-aminosalicylate is crystalline and is characterized by a TGA profile as shown in FIG. 52. In one embodiment, the 4-aminosalicylate is crystalline and is characterized by at least two of the following features (I-i)-(I-ii):

(I-i) an XRPD pattern having peaks at 2θ angles of 7.1°, 19.2°, and 20.9±0.2°;
(I-i) a DSC profile as shown in FIG. 52; or
(I-iii) a TGA profile as shown in FIG. 52.

In one embodiment, the 4-aminosalicylate is crystalline and is 4-aminosalicylate Type B.

4-Aminosalicylate Type B is characterized by the following XRPD pattern expressed in terms of the degree 2θ and relative intensities:

| Angle (Degree 2θ) | Relative Intensity* % |
|---|---|
| 4.9 | 25.56 |
| 7.1 | 56.62 |
| 11.0 | 19.65 |
| 11.3 | 19.26 |
| 14.1 | 23.84 |
| 15.3 | 12.80 |
| 15.9 | 11.06 |
| 16.2 | 16.11 |
| 17.1 | 44.78 |
| 17.6 | 31.62 |
| 17.9 | 38.01 |
| 19.2 | 48.39 |
| 19.4 | 68.17 |
| 19.7 | 100.00 |
| 19.9 | 54.95 |
| 20.3 | 26.88 |
| 20.6 | 29.74 |
| 20.9 | 63.04 |
| 21.7 | 33.46 |
| 22.0 | 39.06 |
| 22.4 | 11.40 |
| 22.8 | 23.43 |
| 23.2 | 17.82 |
| 24.0 | 24.83 |
| 25.8 | 16.32 |
| 26.6 | 26.29 |
| 28.6 | 8.07 |
| 29.8 | 5.74 |

*The relative intensities may change depending on the crystal size and morphology.

Figure 69:
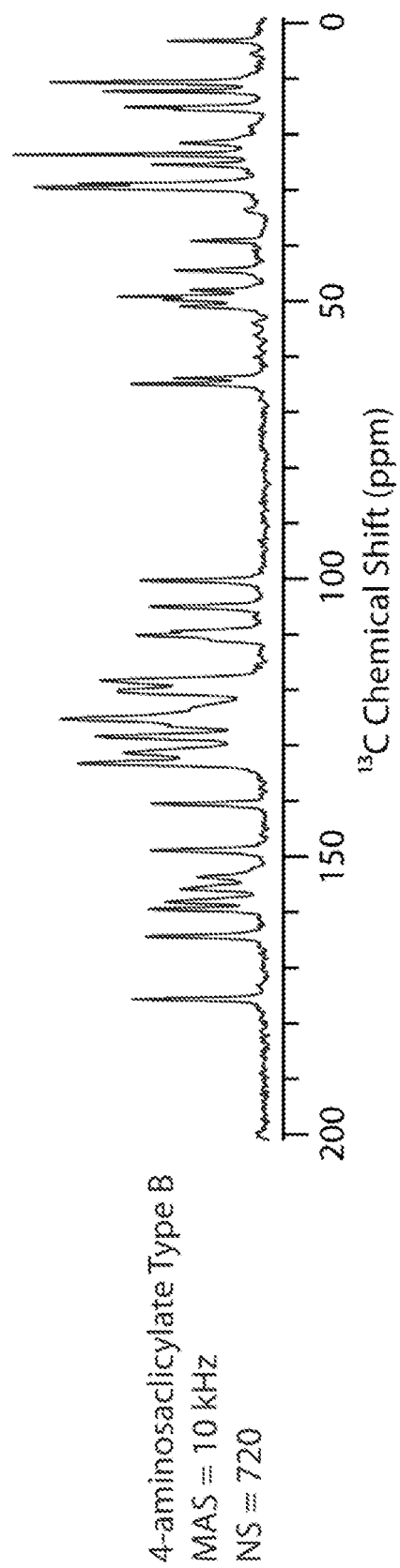
FIG. 69 is a $^{13}$C SSNMR spectrum of 4-aminosalicylate Type B.

In one embodiment, 4-aminosalicylate Type B is characterized by the SSNMR of FIG. 69. In one embodiment, 4-aminosalicylate Type B is characterized by the following $^{13}$C Solid State NMR shifts.

| v(F1) [ppm] | Intensity [abs] |
|---|---|
| 175.64 | 278510206 |
| 164.37 | 251030673 |
| 159.46 | 244999941 |
| 158.19 | 208576957 |
| 155.82 | 176944910 |
| 153.67 | 140602964 |
| 148.86 | 240864993 |
| 140.48 | 240782395 |
| 133.24 | 398260582 |
| 131.34 | 298971870 |
| 128.37 | 359079883 |
| 126.54 | 202963812 |
| 125.24 | 434189316 |
| 123.52 | 159834935 |
| 121.62 | 62054799 |
| 120.31 | 311252320 |
| 118.29 | 349314133 |
| 110.15 | 271111093 |
| 109.47 | 198204011 |
| 105.00 | 242651525 |
| 100.31 | 263138400 |
| 66.04 | 15824943 |
| 64.91 | 281542378 |
| 63.86 | 191084766 |
| 60.09 | 19455038 |
| 56.13 | 20163913 |
| 53.94 | 24890958 |
| 50.95 | 177817081 |
| 49.77 | 213161236 |
| 49.18 | 311176617 |
| 48.03 | 157137406 |
| 44.48 | 189994725 |
| 43.42 | 19169479 |
| 42.34 | 15001136 |
| 41.84 | 16888763 |
| 41.30 | 16289177 |
| 40.89 | 22235755 |
| 40.10 | 19573476 |
| 39.15 | 153613898 |
| 33.49 | 40222513 |
| 32.28 | 17091567 |
| 31.67 | 25115726 |
| 31.20 | 25655700 |
| 29.49 | 493405116 |
| 28.87 | 396829389 |
| 26.88 | 37139669 |
| 25.44 | 238321995 |
| 23.62 | 534604199 |
| 21.53 | 178063112 |
| 19.46 | 27716127 |
| 19.09 | 23987196 |
| 18.53 | 30682617 |
| 15.54 | 190239118 |
| 15.07 | 295558628 |
| 13.71 | 15464629 |
| 13.15 | 15557041 |
| 12.24 | 341668865 |
| 10.55 | 455082213 |
| 8.68 | 15518351 |
| 7.80 | 16526924 |
| 5.46 | 27234201 |
| 3.18 | 202859619 |
| 1.74 | 15911338 |

Representative $^{13}$C NMR chemical shifts for 4-aminosalicylate Type B are 126.54, 118.29, 49.18, and 39.15 ppm. Representative $^{13}$C NMR chemical shifts for 4-aminosalicylate Type B are also 126.54 and 118.29 ppm.

Pharmaceutical Compositions

In another aspect, the present invention provides pharmaceutical compositions comprising one or more pharmaceutically acceptable salts of COMPOUND I. In one embodiment, a pharmaceutical composition comprises a pharmaceutically acceptable salt of COMPOUND I selected from the group consisting of 1-hydroxy-2-naphthate, 4-aminosalicyate, adipate, L-aspartate, benzene sulfonate, benzoate, trans-cinnamate, citrate, fumarate, galactarate, gentisate, gluconate, glutamate, glutarate, hexanoate, hippurate, hydrobromide, hydrochloride, L-lactate, maleate, L-malate, malonate, R-mandelate, methane sulfonate, naphthalene sulfonate, nicotinate, oxalate, palmitate, phosphorate, propionate, saccharinate, salicyclate, stearate, succinate, sulfurate, L-tartarate, vanillate, and vanillin and a pharmaceutically acceptable excipient, diluent, carrier, or mixture thereof. In one embodiment, a pharmaceutical composition comprises a pharmaceutically acceptable salt of COMPOUND I is selected from the group consisting of 4-aminosalicylate, fumarate, galactarate, gentisate, hippurate, hydrobromide, hydrochloride, L-lactate, maleate, L-malate, oxalate, phosphorate, saccharinate, salicyclate, L-tartarate, and vanillinate and a pharmaceutically acceptable excipient, diluent, carrier, or mixture thereof.

In another aspect, the present invention also provides methods of producing a pharmaceutical composition comprising a pharmaceutically acceptable salt of COMPOUND I. In one embodiment, a method of producing a pharmaceutical composition comprises combining a pharmaceutically acceptable salt of COMPOUND I with a pharmaceutically acceptable excipient, diluent, carrier, or a mixture thereof. In one embodiment, a method for producing a pharmaceutical composition comprises a pharmaceutically acceptable salt of COMPOUND I selected from the group consisting of selected from the group consisting of 1-hydroxy-2-naphthate, 4-aminosalicyate, adipate, L-aspartate, benzene sulfonate, benzoate, trans-cinnamate, citrate, fumarate, galactarate, gentisate, gluconate, glutamate, glutarate, hexanoate, hippurate, hydrobromide, hydrochloride, L-lactate, maleate, L-malate, malonate, R-mandelate, methane sulfonate, naphthalene sulfonate, nicotinate, oxalate, palmitate, phosphorate, propionate, saccharinate, salicyclate, stearate, succinate, sulfurate, L-tartarate, vanillate, and vanillin with a pharmaceutically acceptable excipient, diluent, carrier, or a mixture thereof. In one embodiment, a method for producing a pharmaceutical composition comprises combining a pharmaceutically acceptable salt of COMPOUND I is selected from the group consisting of 4-aminosalicylate, fumarate, galactarate, gentisate, hippurate, hydrobromide, hydrochloride, L-lactate, maleate, L-malate, oxalate, phosphorate, saccharinate, salicyclate, L-tartarate, and vanillinate with a pharmaceutically acceptable excipient, diluent, carrier, or a mixture thereof.

Pharmaceutical compositions of the present invention comprising a pharmaceutically acceptable salt of COMPOUND I may be in a form suitable for oral use, for example, as tablets, troches, lozenges, dispersible powders or granules, or hard or soft capsules. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations.

Tablets, troches, lozenges, dispersible powders or granules, or hard or soft capsules may contain a pharmaceutically acceptable salt of COMPOUND I in admixture with non-toxic pharmaceutically-acceptable excipients which are suitable for the manufacture of such tablets, troches, lozenges, dispersible powders or granules, or hard or soft capsules. These excipients may be for example, inert diluents, such as calcium carbonate, sodium carbonate, lactose, microcrystalline cellulose, calcium phosphate or sodium phosphate; granulating and disintegrating agents, for example corn starch, croscarmelose sodium, or alginic acid; binding agents, for example, starch, gelatin or acacia; and lubricating agents or glidants, for example magnesium stearate, stearic acid, colloidal silicon dioxide, or talc. Hard gelatin capsules may include a pharmaceutically acceptable salt of COMPOUND I in combination with an inert solid excipient, diluent, carrier, or mixture thereof.

A "pharmaceutically acceptable carrier, diluent, or excipient" is a medium generally accepted in the art for the delivery of biologically active agents to mammals, e.g., humans. Such carriers are generally formulated according to a number of factors well within the purview of those of ordinary skill in the art to determine and account for. These include, without limitation, the type and nature of the active agent being formulated; the subject to which the agent-containing composition is to be administered; the intended route of administration of the composition; and the therapeutic indication being targeted. Pharmaceutically acceptable carriers and excipients include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., Remington's Pharmaceutical Sciences, 17th ed., Mack Publishing Company, Easton, Pa. 1985, the contents of which are incorporated herein by reference.

Methods of Treatment

In another aspect, the present invention provides pharmaceutical compositions comprising a therapeutically effective amount of a pharmaceutically acceptable salt of COMPOUND I wherein a therapeutically effective amount of COMPOUND I comprises a sufficient amount for the treatment of a RAGE mediated disorder.

In another aspect, the present invention provides a method for treating a RAGE mediated disease comprising administering a pharmaceutically acceptable salt of COMPOUND I to a subject in need thereof. The method may comprise administering a pharmaceutical composition comprising a therapeutically effective amount of a pharmaceutically acceptable salt of COMPOUND I to a subject in need thereof.

A pharmaceutical composition of the present invention may be administered at a dosage level of less than 100 mg of compound per day. In another embodiment, the dosage level of administration is greater than 1 mg of compound per day. The amount of active ingredient that may be combined with the carrier materials to produce a single dosage will vary depending upon the host treated and the particular mode of administration. For example, in one non-limiting embodiment, a dosage unit forms, such as a tablet or capsule, intended for oral administration to humans may contain less than 100 mg of COMPOUND I with an appropriate and convenient amount of carrier material. In another embodiment, the dosage level of administration is greater than 1 mg of compound per day. In another embodiment, the dosage level of administration is 5, 10 or 20 mg of compound per day.

The dosage may be individualized by the clinician based on the specific clinical condition of the subject being treated. Thus, it will be understood that the specific dosage level for any particular subject will depend upon a variety of factors including the activity of the specific compound employed, the age, body weight, general health, sex, diet, time of administration, route of administration, rate of excretion, drug combination and the severity of the particular disease undergoing therapy.

EXAMPLES

Analytical Methods
X-Ray Powder Diffraction (XRPD) Analysis

XRPD analysis was performed with a Panalytical X'Pert[3] Powder XRPD on a Si zero-background holder. The 2θ position was calibrated against Panalytical Si reference standard disc. The XRPD parameters used are listed in Table 1.

TABLE 1

Parameters for XRPD test

| Parameters | Reflection Mode |
|---|---|
| X-Ray wavelength | Cu, kα |
| Kα1 (Å) | 1.540598 |
| Kα2 (Å) | 1.544426 |
| Kα2/Kα1 intensity ratio | 0.50 |
| X-Ray tube setting | 45 kV, 40 mA |
| Divergence slit | Fixed ⅛° |
| Scan mode | Continuous |
| Scan range | (°2TH) 3-40 |
| Scan step time [s] | 18.87 |
| Step size (°2TH) | 0.0131 |
| Test Time | 4 min 15 s |

$^1$H NMR

Solution NMR was collected on Bruker 500M NMR Spectrometer using DMSO-d6 and CD$_3$OD as solvents.

HPLC

Agilent 1100 HPLC was utilized to analyze the purity and stoichiometry, with detailed method listed in below.

| Item | Value | | | |
|---|---|---|---|---|
| Column | Gemini C18 110 A, 250 × 4.6 mm, 5 μm | | | |
| Mobile phase | A: 0.05% TFA in H$_2$O<br>B: 0.05% TFA in H$_2$O acetonitrile | | | |
| | Purity | | Stoichiometry | |
| Gradient table | Time (min) | % B | Time (min) | % B |
| | 0.0 | 25 | 0.0 | 20 |
| | 20.0 | 40 | 6.0 | 95 |
| | 25.0 | 55 | 7.0 | 95 |
| | 35.0 | 95 | 7.1 | 20 |
| | 40.0 | 95 | 10.0 | 20 |
| | 40.1 | 25 | — | — |
| | 50.0 | 25 | — | — |
| Run time | 50.0 min | | 10.0 min | |
| Post time | 0.0 min | | | |
| Flow rate | 1.0 mL/min | | | |
| Injection volume | 5 μL | | | |
| Detector wavelength | UV at 255 nm | | | |
| Column temperature | 40° C. | | | |
| Sampler temperature | RT | | | |
| Diluent | Acetonitrile | | | |

IC

IC method for counter-ion content measurement is listed below.

| Item | Value |
| --- | --- |
| Column | IonPac AS18 Analytical Column (4 × 250 mm) |
| Mobile Phase | 25 mM NaOH |
| Injection volume | 25 μL |
| Flow rate | 1.0 mL/min |
| Cell temperature | 35° C. |
| Column temperature | 35° C. |
| Current | 80 mA |
| Run Time | 6 mins (Cl⁻), 8 mins (Br⁻), 10 mins ($C_2O_4^{2-}$), 14 mins ($PO_4^{3-}$) |

Thermogravimetry Analysis (TGA) and Differential Scanning Calorimetry (DSC)

TGA data were collected using a TA Q500 and Q550 from TA Instruments. DSC was performed using a TA Q2000 from TA Instruments. DSC was calibrated with Indium reference standard and the TGA was calibrated using nickel reference standard. Detailed parameters used are listed in Table 2.

TABLE 2

Parameters for TGA and DSC test

| Parameters | TGA | DSC |
| --- | --- | --- |
| Method | Ramp | Ramp |
| Sample pan | Aluminum, open | Aluminum, crimped |
| Temperature | RT - desired temperature | 25° C. - desired temperature |
| Heating rate | 10° C./min | 10° C./min |
| Purge gas | $N_2$ | $N_2$ |

Solid-state Nuclear Magnetic Resonance (SSNMR)

Experiments were performed on a Bruker NEO spectrometer (Bruker, Billerica, MA) operating at 100.47 MHz for 13C and 399.50 MHz for ¹H. Data acquisition, collection, and processing was preformed using the Bruker Topspin 4.0.1 software package. Each sample was packed into a 4 mm zirconia rotor. Teflon end spacers were used to contain the sample in the central part of the rotor. All experiments were acquired using Cross Polarization/Magic Angle Spinning (CP/MAS). Data was acquired with a magic angle spinning speed of 10 kHz (high quality spectra) and at 9 kHz (quick spectrum) to identify isotropic shifts vs spinning sidebands. A Revolution NMR HX widebore probe (Revolution NMR, Fort Collins, CO) was used, with a 4 mm magic angle spinning module. ¹H decoupling was used, and was applied at 100 kHz (2.5 us H90). Proton decoupling was applied during acquisition.

Chemical shifts were reported relative to TMS via a secondary reference of the methyl peak of 3-methylglutaric acid (MGA) at 18.84 ppm with an accuracy of ±0.2 ppm.

Crystalline Form II of COMPOUND I, described in U.S. Pat. No. 7,884,219, was used as the starting material in each of the following Examples. U.S. Pat. No. 7,884,219, herein incorporated by reference, provides a method for preparing Crystalline Form II of COMPOUND I.

Example 1

A total of 320 salt/co-crystal screening experiments were conducted using 38 acids (two molar ratios for HCl and HBr) and eight solvent systems. Specifically, freebase stock solutions of ~100 mg/mL were first prepared in each solvent system. For each experiment, 0.2 mL stock solution and the corresponding acids were mixed in a molar charge ratio of 1:1 (acid/freebase, 2:1 for HCl/freebase and HBr/freebase as well), and then stirred at RT. After stirring for 3-5 days, if precipitation was observed, the precipitate was isolated. It no precipitation, the clear solutions were first transferred to slurry at 5° C. to introduce precipitation. Solutions without any precipitation were further subjected to anti-solvent addition (for solvents in column B/D, 0.5 mL hexane was added; for solvents in column G/H, 0.5 mL water was added; for solvent in column F, 0.5 mL n-heptane was added). If still no precipitation, the final clear solutions were transferred to evaporation at RT to induce precipitation. All solids isolated were vacuum dried at RT for 2 hrs before XRPD analysis.

As summarized in Table 1, a total of 17 crystalline salt/co-crystal hits were obtained from the screening, namely saccharinate Type A, vanillate Type A, HCl salt Type A, fumarate Type A, maleate Type A, galactarate Type A, phosphate Type A, L-tartrate Type A, hippurate Type A, L-malate Type A, oxalate Type A, gentisate Type A/B, mesylate Type A, HBr salt Type A/B, and 4-aminosalicylate Type A.

TABLE 1

Summary of salt screening experiments

| | | Solvent | | | | | | | |
| --- | --- | --- | --- | --- | --- | --- | --- | --- | --- |
| | Former | Ethanol | Ethyl acetate/ Hexane (1:2, v/v) | THF | Acetone/ Hexane (1:2, v/v) | Toluene | Methyl tertbutyl ether | Methanol/ $H_2O$ (19:1, v/v) | Dioxane/$H_2O$ (9:1, v/v) |
| | | A | B | C | D | E | F | G | H |
| 1 | HCl (1:1) | HCl salt Type A* | HCl salt Type A | HCl salt Type A | HCl salt Type A | HCl salt Type A | HCl salt Type A | HCl salt Type A* | gel* |
| 2 | HCl (2:1) | HCl salt Type A | HCl salt Type A | HCl salt Type A + FB Type A | HCl salt Type A | HCl salt Type A + FB Type A | HCl salt Type A + FB Type A | gel* | low crystallinity* |
| 3 | HBr (1:1) | HBr salt Type A | HBr salt Type A | HBr salt Type A | HBr salt Type A | HBr salt Type A | HBr salt Type A | HBr salt Type A* | gel* |
| 4 | HBr (2:1) | HBr salt Type B | HBr salt Type B | HBr salt Type B | HBr salt Type B | HBr salt Type B | HBr salt Type B | HBr salt Type B* | HBr salt Type B# |
| 5 | $H_2SO_4$ | gel* | gel | gel | gel | amorphous* | amorphous# | gel* | gel* |
| 6 | $H_3PO_4$ | gel* | phosphate Type A | gel* | phosphate Type A | phosphate Type A | phosphate Type A + FB Type B | gel* | gel* |
| 7 | Methane sulfonic acid | gel* | mesylate Type A | gel | gel | gel* | amorphous | gel* | gel* |

TABLE 1-continued

Summary of salt screening experiments

| | Former | Ethanol A | Ethyl acetate/Hexane (1:2, v/v) B | THF C | Acetone/Hexane (1:2, v/v) D | Toluene E | Methyl tertbutyl ether F | Methanol/H₂O (19:1, v/v) G | Dioxane/H₂O (9:1, v/v) H |
|---|---|---|---|---|---|---|---|---|---|
| 8 | Benezene Sulfonic acid | gel* | gel | gel | gel | gel* | amorphous# | gel* | gel* |
| 9 | Nahthalene sulfonic acid | amorphous* | gel* | gel | gel* | gel* | amorphous | amorphous& | amorphous* |
| 10 | Oxalic acid | oxalate Type A | oxalate Type A | oxalate Type A | oxalate Type A | oxalate Type A | oxalate Type A | gel* | oxalate Type A& |
| 11 | L-aspartic acid | L-aspartic acid | L-aspartic acid | L-aspartic acid | L-aspartic acid | L-aspartic acid | L-aspartic acid | L-aspartic acid | L-aspartic acid |
| 12 | Maleic acid | gel* | low crystallinity | gel* | maleate Type A* | gel* | low crystallinity | amorphous* | amorphous* |
| 13 | Glutamic acid | glutamic acid | glutamic acid | glutamic acid | glutamic acid | glutamic acid | glutamic acid | glutamic acid | glutamic acid |
| 14 | Malonic acid | gel* | amorphous* | gel* | amorphous* | gel* | gel* | amorphous* | amorphous* |
| 15 | Gentisic acid | gel* | gentisate Type B | gel* | gentisate Type A + FB Type B& | gentisate Type B | gentisate Type A | genisate Type A& | gentisate Type B& |
| 16 | L-tartaric acid | L-tartrate Type A* | L-tartrate Type A | L-tartrate Type A* | L-tartrate Type A* | L-tartrate Type A* | L-tartrate Type A | amorphous* | L-tartrate Type A* |
| 17 | Fumaric acid | gel* | fumarate Type A | gel* | fumarate Type A | fumarate Type A + FB Type B* | fumarate Type A | amorphous* | amorphous* |
| 18 | Gluconic acid | amorphous* | gel* | amorphous* | amorphous& | gel | amorphous | amorphous* | amorphous* |
| 19 | Benzoic acid | gel* | gel* | gel* | gel* | gel* | amorphous* | amorphous* | amorphous* |
| 20 | Citric acid | gel* | low crystallinity | amorphous# | low crystallinity | amorphous | amorphous | amorphous* | amorphous* |
| 21 | Hippuric acid | gel* | hippurate Type A# | gel* | amorphous* | gel* | hippurate Type A | amorphous* | amorphous* |
| 22 | Succnic acid | gel* | amorphous* | gel* | amorphous* | gel* | FB Type B* | amorphous* | amorphous* |
| 23 | Adipic acid | gel* | amorphous* | gel* | FB Type B* | gel* | amorphous* | amorphous* | amorphous* |
| 24 | Nicotinic acid | gel* | nicotinic acid | gel* | nicotinic acid | nicotinic acid | nicotinic acid | amorphous* | amorphous* |
| 25 | Salicyclic acid | gel* | amorphous* | gel* | amorphous* | gel* | amorphous& | amorphous* | amorphous* |
| 26 | Galactaric acid | galactarate Type A | galactarate Type A | galactarate Type A | galactarate Type A | galactarate Type A | galactarate Type A | galactarate Type A | galactarate Type A |
| 27 | Glutaric acid | gel* | amorphous* | gel* | amorphous* | gel* | amorphous& | amorphous* | amorphous* |
| 28 | Stearic acid | FB Type A + B* | FB Type A + B* | FB Type A + B* | FB Type A + B* | FB Type A + B* | FB Type A* | FB Type A + B& | amorphous& |
| 29 | Palmitic acid | gel* | gel* | gel* | gel* | gel* | gel* | FB Type A& | gel* |
| 30 | Propionic acid | gel* | FB Type A | gel* | gel* | gel* | FB Type B* | FB Type A& | amorphous* |
| 31 | Vanillin | gel* | gel* | gel | gel* | gel | amorphous* | amorphous& | FB Type A& |
| 32 | Saccharin | amorphous* | saccharinate Type A | gel | gel | gel | saccharinate Type A | saccharinate Type A& | amorphous* |
| 33 | trans Cinnamic acid | amorphous | gel | gel | gel | gel | amorphous* | amorphous* | amorphous* |
| 34 | 4-Aminosalicylic acid | gel* | 4-aminosalicylate Type A | gel | gel | gel | 4-aminosalicylate Type A | 4-aminosalicylate Type A + FB Type B& | gel |
| 35 | L-malic acid | amorphous* | L-malate Type A | gel | gel | gel | L-malate Type A | amorphous* | amorphous* |
| 36 | Vanillic acid | amorphous | vanillate Type A | gel | vanillate Type A | gel | vanillate Type A | amorphous* | amorphous* |
| 37 | L-lactic acid | amorphous* | gel* | gel | gel | gel | gel | amorphous* | amorphous* |
| 38 | Hexanoic acid | gel | gel* | gel | gel* | gel | FB Type B& | amorphous* | FB Type A* |
| 39 | R-mandelic acid | amorphous* | gel* | gel | gel | gel | gel | amorphous* | amorphous* |

TABLE 1-continued

Summary of salt screening experiments

| | | Solvent | | | | | | |
|---|---|---|---|---|---|---|---|---|
| Former | Ethanol A | Ethyl acetate/ Hexane (1:2, v/v) B | THF C | Acetone/ Hexane (1:2, v/v) D | Toluene E | Methyl tertbutyl ether F | Methanol/ $H_2O$ (19:1, v/v) G | Dioxane/$H_2O$ (9:1, v/v) H |
| 40 1-hydroxy-2-naphthoic acid | amorphous* | gel* | gel | gel | gel | gel | amorphous* | amorphous* | obtained via 5° C. slurry;
&obtained via anti-solvent addition;
*obtained via evaporation.

Example 2

All hits were further characterized by TGA and DSC, with the stoichiometry determined by $^1$H NMR or HPLC/IC. Based on the characterization data in Table 2 below, most of them were considered to be anhydrates.

TABLE 2

Characterization summary of crystalline hits

| Hit | Safety Class | Sample ID (807943-) | Stoichiometry (acid/base) | TGA Wt. Loss (%) | DSC Endo. (onset, °C.) | Speculated Form |
|---|---|---|---|---|---|---|
| Saccharinate Type A | N/A | 05-B32 | 1.22 | negligible | 120.0 | Anhydrate |
| Vanillate Type A | N/A | 05-B36 | 1.04 | negligible | 99.6 | Anhydrate |
| HCl Salt Type A | I | 05-B2 | 1.33 | negligible | 167.0 | Anhydrate |
| Fumarate Type A | I | 05-D17 | 1.00 | negligible | 115.0 | Anhydrate |
| Maleate Type A | I | 12-A | 0.97 | negligible | 120.2 | Anhydrate |
| Galactarate Type A | I | 05-H26 | 0.98 | 0.6 up to 130° C. | 106.3*, 158.4 | Anhydrate |
| Phosphate Type A | I | 05-D6 | 0.91 | 0.3 up to 100° C. | 105.4, 138.0* | Anhydrate |
| L-Tartrate Type A | I | 05-B16 | 1.00 | 2.1 up to 60° C. | 76.4 | Hydrate |
| Hippurate Type A | I | 05-B21 | 0.98 | negligible | 44.3*, 72.7 | Anhydrate |
| L-Malate Type A | I | 05-B35 | 1.11 | negligible | 67.8 | Anhydrate |
| Oxalate Type A | II | 05-F10 | 1.12 | negligible | 109.5 | Anhydrate |
| Gentisate Type A | II | 05-F15 | 1.01 | 1.8 up to 120° C. | 89.9, 129.2 | Hydrate |
| Type B | | 05-E15 | 1.03 | negligible | 122.9 | Anhydrate |
| Mesylate Type A | II | 05-B7 | + | + | + | Unidentified |
| HBr salt Type A | III | 05-A3 | 1.05 | negligible | 169.9 | Anhydrate |
| Type B | | 05-F4 | 2.07 | negligible | 167.5, 231.5 | Anhydrate |
| 4-Aminosalicylate Type A | III | 05-F34 | 1.01 | negligible | 81.7 | Anhydrate |

*peak temperature
+: sample converted to gel after storage at ambient conditions.

Example 3

Figure 2:
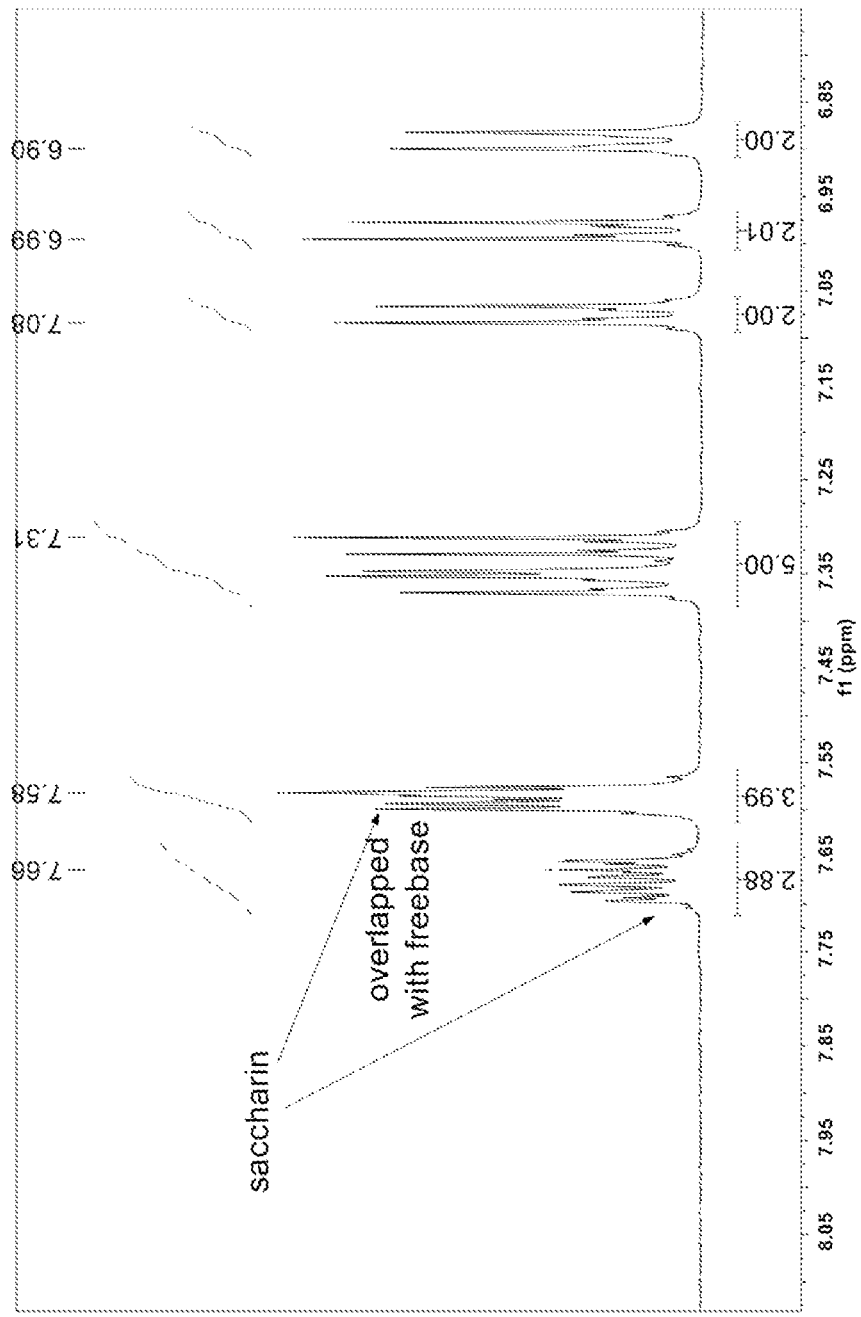
FIG. 2 is a $^1$H NMR spectrum of saccharinate Type A.

One saccharinate crystal form was obtained via screening. Saccharinate Type A was generated via stirring the freebase and saccharin in ethyl acetate/hexane (1:2, v/v) at RT, with a molar charge ratio of 1:1 (acid/freebase). The XRPD pattern was displayed in FIG. 1. Negligible weight loss was observed before decomposition in TGA and DSC data (FIG. 3) showed a single sharp endotherm at 120.0° C. (onset temperature) possibly due to melting. Based on the integration of the phenyl protons (2H) of freebase at ~7.1 ppm and the phenyl protons (4H) of saccharin at ~7.6 ppm, the ratio of saccharin to freebase was determined as 1.22:1 by $^1$H NMR using $CD_3OD$ as shown in FIG. 2. Based on the characterization results, saccharinate Type A was considered to be an anhydrate.

Example 4

One vanillate crystal form was generated via screening. Vanillate Type A was obtained via stirring the freebase and vanillic acid in ethyl acetate/hexane (1:2, v/v) at RT, with a molar charge ratio of 1:1 (acid/freebase). The XRPD pattern was shown in FIG. 4. As per TGA and DSC results in FIG. 6, negligible weight loss was observed before decomposition and DSC result showed a sharp endothermic peak at 99.6° C. (onset temperature) possibly due to melting. Based on the integration of the phenyl protons (2H) of freebase at ~7.1 ppm and the phenyl protons (3H) of vanillic acid at ~6.8/7.5/7.6 ppm, the ratio of counter ion to freebase was determined as 1.04:1 by $^1$H NMR using CD$_3$OD as shown in FIG. 5. Based on the characterization results, Type A was considered to be an anhydrate of mono-vanillate.

Example 5

One HCl salt crystal form was obtained from screening. HCl salt Type A was obtained via reactive crystallization (molar charge of 2:1, acid/freebase) in ethyl acetate/hexane (1:2, v/v) at RT. The XRPD pattern of Type A is displayed in FIG. 7. Negligible weight loss was observed before decomposition in TGA and DSC results (FIG. 8) showed a sharp endothermic peak at 167.0° C. (onset temperature) possibly due to melting. Also, the stoichiometry was determined as 1.33 (acid/base) for the sample by HPLC/IC. Therefore, HCl salt Type A was speculated to be an anhydrate.

Figure 9:
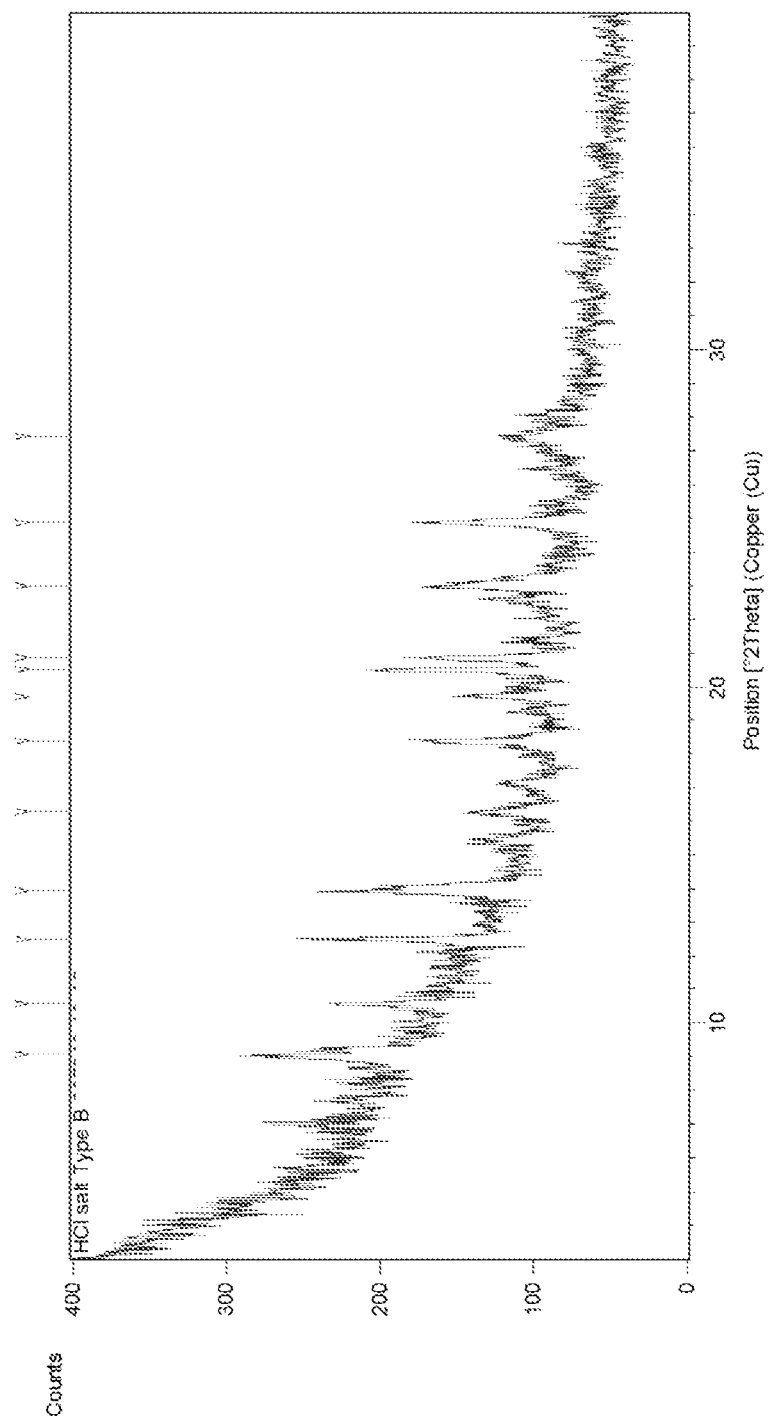
FIG. 9 is a XRPD Pattern of HCl Type B.

A second HCl salt crystal form (Type B) was obtained by stirring free base in ethanol at 5° C. (molar charge ratio of 2:1, acid/freebase). The XRPD of Type B is displayed in FIG. 9. Negligible weight loss was observed before decomposition in TGA and DSC results (FIG. 10) show an endothermic peak at 232.4° C. HCl salt Type B was speculated to be an anhydrate. HCl salt Type B is a di-hydrochloride.

Example 6

One fumarate crystal form was obtained via screening. Fumarate Type A was generated via stirring the freebase with fumaric acid in acetone/hexane (1:2, v/v) at RT, with a molar charge ratio of 1:1 (acid/freebase). The XRPD pattern was shown in FIG. 11. TGA and DSC data in FIG. 13 showed negligible weight loss before decomposition and a sharp endothermic peak at 115.0° C. (onset temperature) possibly due to melting. Based on the integration of the phenyl proton (2H) of freebase at ~7.7 ppm and CH proton (2H) of fumaric acid at ~6.6 ppm, the ratio of counter ion to freebase was determined as 1.00:1 by $^1$H NMR using DMSO-d6 as shown in FIG. 12. Therefore, Type A was speculated to be an anhydrate of mono-fumarate.

Example 7

One maleate crystal form was obtained via screening. Maleate Type A was generated via stirring the freebase with maleic acid in ethyl acetate/hexane (1:2, v/v) at RT, with a molar charge ratio of 1:1 (acid/freebase). The XRPD pattern is displayed in FIG. 14. As per TGA and DSC data shown in FIG. 16, negligible weight loss was observed before decomposition and DSC result showed a sharp melting peak 120.2° C. (onset temperature). Based on the integration of the phenyl proton (2H) of freebase at ~7.7 ppm and CH proton (2H) of maleic acid at ~6.0 ppm, the ratio of counter ion to freebase was determined as 0.97:1 by $^1$H NMR using DMSO-d6 as shown in FIG. 15. Therefore, Type A was speculated to be an anhydrate of mono-maleate.

Example 8

One galactarate crystal form was obtained via screening. Galactarate Type A was generated via stirring the freebase with galactaric acid in dioxane/H2O (9:1, v/v) at RT, with a molar charge ratio of 1:1 (acid/freebase). The XRPD pattern is displayed in FIG. 17. A weight loss of 0.6% was observed up to 130° C. and DSC data (FIG. 19) showed a broad endotherm at 106.3° C. (peak temperature) possibly due to moisture/solvent loss, followed by melting at 158.4° C. (onset temperature). Based on the integration of the phenyl proton (2H) of freebase at ~7.7 ppm and CH proton (4H) of galactaric acid at ~3.7/4.2 ppm, the ratio of counter ion to freebase was determined as 0.98:1 by $^1$H NMR using DMSO-d6 as shown in FIG. 18. Based on with the results, Type A was considered to be an anhydrate of mono-galactarate.

Example 9

One phosphate crystal form was obtained from screening. Phosphate Type A was obtained via reactive crystallization (molar ratio of 1:1) in acetone/hexane (1:2, v/v) at RT, and its XRPD pattern is shown in FIG. 20. TGA and DSC curves (FIG. 21) showed a weight loss of 0.3% up to 100° C. and two sharp endotherms at 107.5° C. and 138.0° C. (peak temperature). Also, the stoichiometry was determined as 0.91 (acid/base) for the sample via HPLC/IC. Therefore, Type A was considered to be an anhydrate of mono-phosphate.

Example 10

One tartrate crystal form was obtained via screening. L-Tartrate Type A was generated via stirring the freebase with L-tartaric acid in ethyl acetate/hexane (1:2, v/v) at RT, with a molar charge ratio of 1:1 (acid/freebase). The XRPD pattern is displayed in FIG. 22. A weight loss of 2.1% was observed up to 60° C., and DSC data (FIG. 24) showed an endotherm at 76.4° C. (onset temperature) before decomposition. Based on the integration of the phenyl proton (2H) of freebase at ~7.7 ppm and CH proton (2H) of L-tartaric acid at ~4.0 ppm, the ratio of counter ion to freebase was determined as 1.00:1 by $^1$H NMR using DMSO-d6 as shown in FIG. 23. Also, no ethyl acetate and limited hexane content was observed by $^1$H NMR. Based on the results, L-tartrate Type A was possibly a hydrate.

Example 11

One hippurate crystal form was obtained via screening. Hippurate Type A was generated via stirring the freebase with hippuric acid in ethyl acetate/hexane (1:2, v/v) at 5° C., with a molar charge ratio of 1:1 (acid/freebase). The XRPD pattern is displayed in FIG. 27. As per TGA and DSC results in FIG. 29, negligible weight loss was observed before decomposition and DSC data showed a minor endotherm at 44.3° C. (peak temperature) before possible melting peak at 72.7° C. (onset temperature). Based on the integration of the phenyl proton (2H) of freebase at ~7.1 ppm and the phenyl proton (5H) of hippuric acid at ~7.5/7.6 ppm, the ratio of counter ion to freebase was determined as 0.98:1 by $^1$H NMR using CD$_3$OD as shown in FIG. 28. Therefore, Type A was considered to be an anhydrate of mono-hippurate.

Example 12

One malate crystal form was obtained via screening. L-Malate Type A was produced via stirring the freebase with L-malic acid in ethyl acetate/hexane (1:2, v/v) at RT, with a molar charge ratio of 1:1 (acid/freebase). The XRPD pattern is displayed in FIG. 30. As per TGA and DSC results in FIG. 32, negligible weight loss was observed before decomposition, and DSC result showed a sharp meting peak at 67.8° C. (onset temperature). Based on the integration of the phenyl proton (2H) of freebase at ~7.1 ppm and the CH2 and CH proton (3H) of L-malic acid at ~2.4/2.6/4.2 ppm, the ratio of counter ion to freebase was determined as 1.11:1 by $^1$H NMR using $CD_3OD$ as shown in FIG. 31. Based on the characterization results, L-malate Type A was speculated to be an anhydrate.

Example 13

One oxalate crystal form was obtained via screening. Oxalate Type A was generated via stirring the freebase with oxalic acid in methyl tert-butyl ether at RT, with a molar charge ratio of 1:1 (acid/freebase). The XRPD pattern was shown in FIG. 33. Negligible weight loss was observed before decomposition in TGA and DSC data (FIG. 34) showed a sharp endotherm at 109.5° C. (onset temperature) possibly due to melting. Also, the stoichiometry was determined as 1.12 (acid/base) for the sample by HPLC/IC. Therefore, Type A was speculated to be an anhydrate of mono-oxalate.

Example 14

A total of two gentisate crystal forms were obtained via screening. Gentisate Type A and Type B were generated via stirring the freebase with gentisic acid in methyl tert-butyl ether and toluene at RT, respectively, with a molar charge ratio of 1:1 (acid/freebase). The XRPD patterns are displayed in FIG. 35 (Type A) and FIG. 38 (Type B).

For gentisate Type A, a weight loss of 1.8% was observed up to 120° C. and DSC data (FIG. 37) showed two endotherms at 89.9° C. and 129.2° C. (onset temperature), with the first due to the dehydration/desolvation and the second due to melting. For gentisate Type B, negligible weight loss was observed before decomposition and DSC result (FIG. 40) showed a sharp endotherm at 122.9° C. (onset temperature). Based on the integration of the phenyl proton (2H) of freebase at ~7.7 ppm and the phenyl proton (3H) of gentisic acid at ~6.7/6.8/7.3 ppm, the ratio of counter ion to freebase was determined as 1.01:1 and 1.03:1 by $^1$H NMR using $CD_3OD$ for gentisate Type A and Type B samples, respectively, with the $^1$H NMR spectra shown in FIG. 36 (Type A) and FIG. 39 (Type B). Also, no methyl tert-butyl ether signal was detected for gentisate Type A sample by $^1$H NMR. Therefore, gentisate Type A was possibly a hydrate and Type B was considered as an anhydrate.

Example 15

One mesylate crystal form was obtained via screening. Mesylate Type A was generated via reactive crystallization (molar ratio of 1:1) in ethyl acetate/hexane (1:2, v/v) at RT. The XRPD pattern is displayed in FIG. 41. No further characterization was performed due to the sample converted to gel after storage at ambient conditions. This suggested the mesylate was most likely highly hygroscopic and unstable under ambient conditions.

Example 16

Two HBr salt crystal forms were obtained via screening. HBr salt Type A was generated via reactive crystallization in ethanol at RT, with a molar charge ratio of 1:1 (acid/freebase). HBr salt Type B was generated via stirring the freebase with the acid solution in methyl tert-butyl ether at RT, with a molar charge ratio of 2:1 (acid/freebase). The XRPD patterns were displayed in FIG. 44 (Type A) and FIG. 46 (Type B).

For HBr salt Type A, negligible weight loss was observed before decomposition and DSC result (FIG. 45) showed a sharp endotherm at 169.9° C. (onset temperature) possibly due to melting. For HBr salt Type B, negligible weight loss was observed before decomposition and DSC result (FIG. 47) showed a minor endotherm at 167.5° C. (onset temperature) possibly due to the presence of small amount of HBr salt Type A or a solid to solid phase transition, followed by a sharp melting peak at 231.5° C. (onset temperature). Also, the stoichiometry of HBr salt Type A and Type B samples were determined as 1.05 and 2.07 (acid/base) by HPLC/IC respectively. Therefore, Type A was considered to be an anhydrate of mono-HBr salt and Type B was speculated to be an anhydrate of di-HBr salt.

Example 17

One 4-aminosalicylate crystal form was obtained via screening. 4-Aminosalicylate Type A was generated via stirring the freebase with 4-aminosalicylic acid in methyl tert-butyl ether at RT, with a molar charge ratio of 1:1 (acid/freebase). The XRPD pattern is displayed in FIG. 48. Negligible weight loss was observed before decomposition in TGA and DSC result showed a sharp endotherm at 81.7° C. (onset temperature) possibly due to melting (FIG. 50). Based on the integration of the phenyl proton (2H) of freebase at ~7.7 ppm and the phenyl proton (3H) of 4-aminosalicylate acid at ~6.1/6.2/7.6 ppm, the ratio of counter ion to freebase was determined as 1.01 by 1H NMR using $CD_3OD$ for the sample, as shown in FIG. 49. Therefore, Type A was considered to be an anhydrate of mono-4-aminosalicylate.

Example 18

Three new forms were obtained during the sample preparation for ssNMR test: L-tartrate Type B, mesylate Type B, and 4-aminosalicylate Type B. All forms were further characterized by TGA and DSC, with the results summarized in the table below and details provided subsequently.

| Hit | Preparation Condition | TGA Wt. Loss (%) | DSC Endo. (peak, ° C.) | Form ID |
|---|---|---|---|---|
| Mesylate Type B | Stir in ethyl acetate/hexane at RT, with equal molar charge ratio of acid/base | Negligible | 41.7, 95.7 | Anhydrate |
| L-Tartrate Type B | Stir in ethyl acetate/hexane at RT, with equal molar charge ratio of acid/base | 0.4 (80° C.) | 74.3, 101.6 | Hydrate/solvate |
| 4-Aminosalicylate Type B | Stir in Methyl tert-butyl ether at RT, with equal molar charge ratio of acid/base | Negligible | 130.8 | Anhydrate |

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the present invention.

Figure 59:
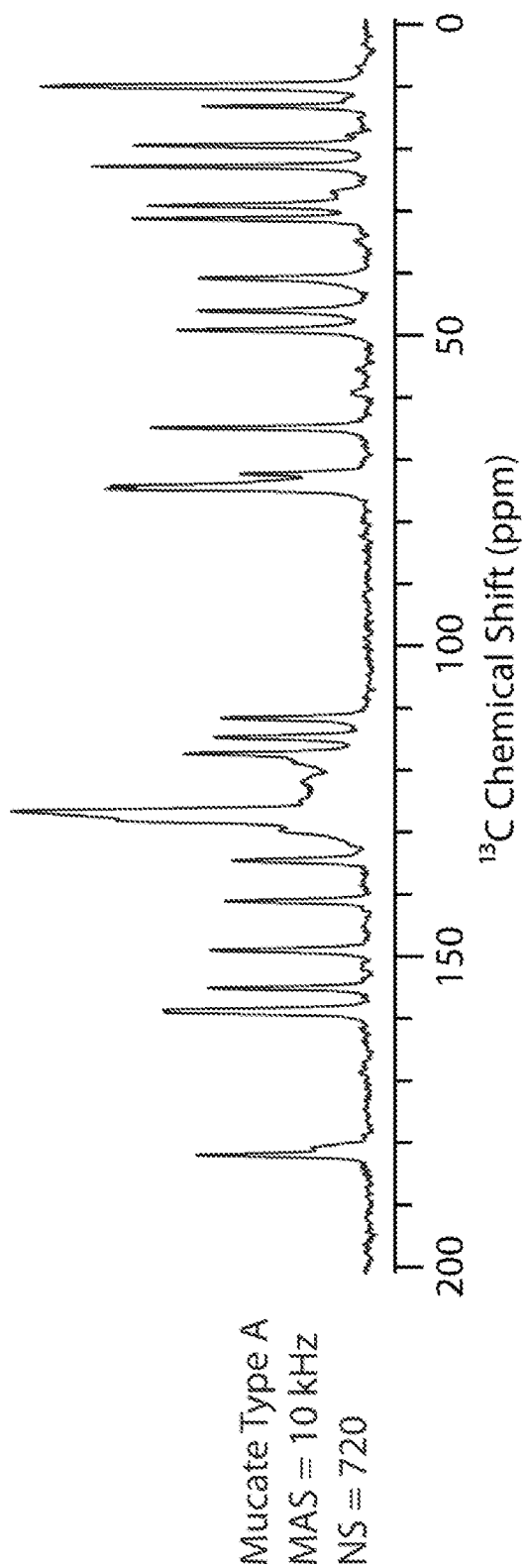
FIG. 59 is a $^{13}$C SSNMR spectrum of galactarate Type A.

What is claimed is:

1. A crystalline form of a saccharinate, vanillate, fumarate, galactarate, hippurate, L-malate, oxalate, or mesylate salt of [3-(4-{2-butyl-1-[4-(4-chlorophenoxy)phenyl]-1H-imidazol-4-yl}phenoxy)-propyl]-diethylamine, wherein: the pharmaceutically acceptable acid is selected from the group consisting of
   a) the crystalline form of the saccharinate salt is characterized by at least two of the following features (I-i)-(I-iv):
      (I-i) an X-ray Powder Diffraction (XRPD) pattern having peaks at 2θ angles of 18.1, 21.1, and 25.7°±0.2°;
      (I-ii) a Differential Scanning Calorimetry (DSC) profile as shown in FIG. 3;
      (I-iii) a TGA profile as shown in FIG. 3; or
      (I-iv) a 13C Solid-state Nuclear Magnetic Resonance (SSNMR) spectrum as shown in FIG. 53;
   b) the crystalline form of the vanillate salt is characterized by at least two of the following features (I-i)-(I-iv):
      (I-i) an XRPD pattern having peaks at 2θ angles of 7.6°, 15.2°, and 18.2°±0.2°;
      (I-ii) a DSC profile as shown in FIG. 6;
      (I-iii) a TGA profile as shown in FIG. 6; or
      (I-iv) a 13C SSNMR spectrum as shown in FIG. 54;
   c) the crystalline form of the fumarate salt is characterized by at least two of the following features (I-i)-(I-iv):
      (I-i) an XRPD pattern having peaks at 2θ angles of 16.6°, 18.0°, and 21.5°±0.2°;
      (I-ii) a DSC profile as shown in FIG. 13;
      (I-iii) a TGA profile as shown in FIG. 13; or
      (I-iv) a 13C SSNMR spectrum as shown in FIG. 57;
   d) the crystalline form of the galactarate salt is characterized by at least two of the following features (I-i)-(I-iv):
      (I-i) an XRPD pattern having peaks at 2θ angles of 8.0°, 14.6°, and 19.7°±0.2°;
      (I-ii) a DSC profile as shown in FIG. 19;
      (I-iii) a TGA profile as shown in FIG. 19; or
      (I-iv) a 13C SSNMR spectrum as shown in FIG. 59;
   e) the crystalline form of the hippurate salt is characterized by at least two of the following features (I-i)-(I-iv):
      (I-i) an XRPD pattern having peaks at 2θ angles of 3.4°, 20.2°, and 20.9°±0.2°;
      (I-ii) a DSC profile as shown in FIG. 29;
      (I-iii) a TGA profile as shown in FIG. 29; or
      (I-iv) a 13C SSNMR spectrum as shown in FIG. 62;
   f) the crystalline form of the L-malate salt is characterized by at least two of the following features (I-i)-(I-iv):
      (I-i) an XRPD pattern having peaks at 2θ angles of 3.7°, 17.2°, and 19.0°±0.2°;
      (I-ii) a DSC profile as shown in FIG. 32;
      (I-iii) a TGA profile as shown in FIG. 32; or
      (I-iv) a 13C SSNMR spectrum as shown in FIG. 63;
   g) the crystalline form of the oxalate salt is characterized by at least two of the following features (I-i)-(I-iv):
      (I-i) an XRPD pattern having peaks at 2θ angles of 16.1°, 17.8°, and 21.9°±0.2°;
      (I-ii) a DSC profile as shown in FIG. 34;
      (I-iii) a TGA profile as shown in FIG. 34; or
      (I-iv) a 13C SSNMR spectrum as shown in FIG. 64;
   h) the crystalline form of the mesylate salt is characterized by at least two of the following features (I-i)-(I-iv):
      (I-i) an XRPD pattern having peaks at 2θ angles of 20.3°, 22.4°, and 23.5°±0.2°;
      (I-ii) a DSC profile as shown in FIG. 43;
      (I-iii) a TGA profile as shown in FIG. 43; or
      (I-iv) a 13C SSNMR spectrum as shown in FIG. 66.

2. A crystalline form of a gentisate salt of [3-(4-{2-butyl-1-[4-(4-chlorophenoxy)phenyl]-1H-imidazol-4-yl}phenoxy)-propyl]-diethylamine, wherein the crystalline form is:
   a) characterized by at least two of the following features (I-i)-(I-iv):
      (I-i) an X-ray Powder Diffraction (XRPD) pattern having peaks at 2θ angles of 7.5°, 21.2°, and 24.7°±0.2°;
      (I-ii) a Differential Scanning calorimetry (DSC) profile as shown in FIG. 37;
      (I-iii) a Thermogravimetry Analysis (TGA) profile as shown in FIG. 37; or
      (I-iv) a 13C Solid-state Nuclear Magnetic Resonance (SSNMR) spectrum as shown in FIG. 65; or
   b) characterized by at least two of the following features (I-i)-(I-iii):
      (I-i) an XRPD pattern having peaks at 2θ angles of 13.3°, 18.4°, and 21.2°±0.2°;
      (I-ii) a DSC profile as shown in FIG. 40; or
      (I-iii) a TGA profile as shown in FIG. 40.

3. A crystalline form of a hydrobromide salt of [3-(4-{2-butyl-1-[4-(4-chlorophenoxy)phenyl]-1H-imidazol-4-yl}phenoxy)-propyl]-diethylamine, wherein the crystalline form is:
   a) characterized by at least two of the following features (I-i)-(I-iv):
      (I-i) an X-ray Powder Diffraction (XRPD) pattern having peaks at 2θ angles of 4.1°, 13.1°, and 16.4°±0.2°;
      (I-i) a Differential Scanning calorimetry (DSC) profile as shown in FIG. 45;
      (I-iii) a Thermogravimetric Analysis (TGA) profile as shown in FIG. 45; or
      (I-iv) a 13C Solid-state Nuclear Magnetic Resonance (SSNMR) spectrum as shown in FIG. 67; or
   b) characterized by at least two of the following features (I-i)-(I-iv):
      (I-i) an XRPD pattern having peaks at 2θ angles of 9.3°, 20.9°, and 23.0°±0.2°;
      (I-ii) a DSC profile as shown in FIG. 47;
      (I-iii) a TGA profile as shown in FIG. 47; or
      (I-iv) a 13C SSNMR spectrum as shown in FIG. 68.

4. A crystalline form of a 4-aminosalicylate salt of [3-(4-{2-butyl-1-[4-(4-chlorophenoxy)phenyl]-1H-imidazol-4-yl}phenoxy)-propyl]-diethylamine, wherein the crystalline form of is:
   a) characterized by at least two of the following features (I-i)-(I-iii):
      (I-i) an X-ray Powder Diffraction (XRPD) pattern having peaks at 2θ angles of 17.1°, 19.2°, and 21.5°±0.2°;
      (I-ii) a Differential Scanning calorimetry (DSC) profile as shown in FIG. 50; or
      (I-iii) a Thermogravimetric Analysis (TGA) profile as shown in FIG. 50; or
   b) characterized by at least two of the following features (I-i)-(I-iii):

(I-i) an XRPD pattern having peaks at 2θ angles of 7.1°, 19.2°, and 20.9°±0.2°;
(I-ii) a DSC profile as shown in FIG. 52;
(I-iii) a TGA profile as shown in FIG. 52; or
(I-iv) a 13C Solid-state Nuclear Magnetic Resonance (SSNMR) spectrum as shown in FIG. 69.

5. A pharmaceutical composition comprising the crystalline form of claim 1 and one or more pharmaceutically acceptable carriers or diluents.

6. A pharmaceutical composition comprising the crystalline form of claim 2 and one or more pharmaceutically acceptable carriers or diluents.

7. A pharmaceutical composition comprising the crystalline form of claim 3 and one or more pharmaceutically acceptable carriers or diluents.

8. A pharmaceutical composition comprising the crystalline form of claim 4 and one or more pharmaceutically acceptable carriers or diluents.

\* \* \* \* \*